United States Patent
Bosanac et al.

(10) Patent No.: US 12,083,114 B2
(45) Date of Patent: Sep. 10, 2024

(54) INHIBITORS OF SARM1 IN COMBINATION WITH NEURO-PROTECTIVE AGENTS

(71) Applicant: Disarm Therapeutics, Inc., Cambridge, MA (US)

(72) Inventors: Todd Bosanac, New Milford, CT (US); Rajesh Devraj, Chesterfield, MO (US); Thomas Engber, Cambridge, MA (US); Robert Owen Hughes, Newtown, CT (US); Raul Eduardo Krauss, Chestnut Hill, MA (US)

(73) Assignee: Disarm Therapeutics, Inc., Cambridge, MA (US)

( * ) Notice: Subject to any disclaimer, the term of this patent is extended or adjusted under 35 U.S.C. 154(b) by 365 days.

(21) Appl. No.: 17/413,689

(22) PCT Filed: Dec. 18, 2019

(86) PCT No.: PCT/US2019/067137
§ 371 (c)(1),
(2) Date: Jun. 14, 2021

(87) PCT Pub. No.: WO2020/132045
PCT Pub. Date: Jun. 25, 2020

(65) Prior Publication Data
US 2022/0008405 A1    Jan. 13, 2022

Related U.S. Application Data

(60) Provisional application No. 62/782,239, filed on Dec. 19, 2018.

(51) Int. Cl.
| | | |
|---|---|---|
| *A61K 31/472* | (2006.01) | |
| *A61K 31/416* | (2006.01) | |
| *A61K 31/425* | (2006.01) | |
| *A61K 31/4355* | (2006.01) | |
| *A61K 31/4365* | (2006.01) | |
| *A61K 31/437* | (2006.01) | |
| *A61K 31/4375* | (2006.01) | |
| *A61K 31/4545* | (2006.01) | |
| *A61K 31/4709* | (2006.01) | |
| *A61K 31/4985* | (2006.01) | |
| *A61K 31/502* | (2006.01) | |
| *A61K 31/5025* | (2006.01) | |
| *A61K 31/519* | (2006.01) | |

(52) U.S. Cl.
CPC .......... *A61K 31/472* (2013.01); *A61K 31/416* (2013.01); *A61K 31/425* (2013.01); *A61K 31/4355* (2013.01); *A61K 31/4365* (2013.01); *A61K 31/437* (2013.01); *A61K 31/4375* (2013.01); *A61K 31/4545* (2013.01); *A61K 31/4709* (2013.01); *A61K 31/4985* (2013.01); *A61K 31/502* (2013.01); *A61K 31/5025* (2013.01); *A61K 31/519* (2013.01)

(58) Field of Classification Search
CPC .................................................... A61K 31/472
See application file for complete search history.

(56) References Cited

U.S. PATENT DOCUMENTS

| | | | |
|---|---|---|---|
| 3,429,882 | A | 2/1969 | Doebel et al. |
| 3,429,887 | A | 2/1969 | Lesher |
| 3,506,668 | A | 4/1970 | Lesher |
| 3,517,014 | A | 6/1970 | Lesher |
| 3,539,567 | A | 11/1970 | Doebel et al. |
| 3,542,777 | A | 11/1970 | Francis |
| 3,624,108 | A | 11/1971 | Doebel et al. |
| 3,629,251 | A | 12/1971 | Francis |
| 3,711,473 | A | 1/1973 | Francis et al. |
| 3,761,493 | A | 9/1973 | Doebel et al. |
| 4,076,534 | A | 2/1978 | Noguchi et al. |
| 4,207,112 | A | 6/1980 | Ikenoue et al. |
| 4,894,371 | A | 1/1990 | Jung et al. |
| 6,420,382 | B2 | 7/2002 | Fraley et al. |
| 6,610,692 | B1 | 8/2003 | Sanderson et al. |
| 6,809,105 | B2 | 10/2004 | Schrimpf et al. |
| 6,849,620 | B2 | 2/2005 | Walker et al. |
| 6,911,543 | B2 | 6/2005 | Walker et al. |
| 7,067,515 | B2 | 6/2006 | Wishka et al. |
| 7,429,609 | B2 | 9/2008 | Ohi et al. |
| 7,491,716 | B2 | 2/2009 | Engler |
| 7,662,832 | B2 | 2/2010 | Kim et al. |
| 7,777,035 | B2 | 8/2010 | Zhang et al. |
| 7,915,410 | B2 | 3/2011 | Johnson et al. |

(Continued)

FOREIGN PATENT DOCUMENTS

| | | |
|---|---|---|
| CN | 102532027 A | 7/2012 |
| CN | 102675310 A | 12/2014 |

(Continued)

OTHER PUBLICATIONS

Patel et al., "Discovery of Dual Leucine Zipper Kinase (DLK, MAP3K12) Inhibitors with Activity in Neurodegeneration Models", Journal of Medicinal Chemistry, Oct. 23, 2014, vol. 58, pp. 401-418 (Year: 2014).*

(Continued)

*Primary Examiner* — Andrew D Kosar
*Assistant Examiner* — Gillian A Hutter
(74) *Attorney, Agent, or Firm* — Nicholas M. Kunz

(57) ABSTRACT

The present disclosure relates to methods of treating neurodegeneration and neurodegenerative diseases comprising administering to a subject in need thereof a combination of a SARM1 inhibitor and a neuroprotective agent.

9 Claims, 8 Drawing Sheets
Specification includes a Sequence Listing.

(56) References Cited

U.S. PATENT DOCUMENTS

| | | |
|---|---|---|
| 7,932,389 B2 | 4/2011 | Swinnen et al. |
| 8,008,320 B2 | 8/2011 | Dannhardt et al. |
| 8,022,065 B2 | 9/2011 | Engler et al. |
| 8,058,425 B2 | 11/2011 | Engler et al. |
| 8,067,452 B2 | 11/2011 | Wu et al. |
| 8,119,635 B2 | 2/2012 | Schrimpf et al. |
| 8,173,655 B2 | 5/2012 | Bell et al. |
| 8,178,131 B2 | 5/2012 | Le Huerou et al. |
| 8,188,114 B2 | 5/2012 | Kim et al. |
| 8,193,359 B2 | 6/2012 | Fyfe et al. |
| 8,242,271 B2 | 8/2012 | Singh et al. |
| 8,258,130 B2 | 9/2012 | Aldous et al. |
| 8,263,767 B2 | 9/2012 | Yuan et al. |
| 8,309,550 B2 | 11/2012 | Luo et al. |
| 8,338,447 B2 | 12/2012 | Hung et al. |
| 8,357,809 B2 | 1/2013 | Johnson et al. |
| 8,436,012 B2 | 5/2013 | Ohtsuka et al. |
| 8,461,176 B2 | 6/2013 | Soll et al. |
| 8,530,468 B2 | 9/2013 | Collins et al. |
| 8,536,339 B2 | 9/2013 | Yuan et al. |
| 8,545,897 B2 | 10/2013 | Le Huerou et al. |
| 8,586,600 B2 | 11/2013 | Singh et al. |
| 8,754,060 B2 | 6/2014 | DiAntonio et al. |
| 8,785,438 B2 | 7/2014 | Ohtsuka et al. |
| 8,785,489 B2 | 7/2014 | Abeywardane et al. |
| 8,846,698 B2 | 9/2014 | Andrews et al. |
| 8,921,353 B2 | 12/2014 | Crawford et al. |
| 8,933,224 B2 | 1/2015 | Chappie et al. |
| 8,981,085 B2 | 3/2015 | Le Huerou et al. |
| 9,051,317 B2 | 6/2015 | Cooymans et al. |
| 9,067,929 B2 | 6/2015 | Singh et al. |
| 9,085,555 B2 | 7/2015 | Altmann et al. |
| 9,108,983 B2 | 8/2015 | Le Tiran et al. |
| 9,127,003 B2 | 9/2015 | Atkinson et al. |
| 9,145,427 B2 | 9/2015 | Chappie et al. |
| 9,181,277 B2 | 11/2015 | Zhang et al. |
| 9,238,655 B2 | 1/2016 | Crawford et al. |
| 9,260,429 B2 | 2/2016 | Hung et al. |
| 9,273,028 B2 | 3/2016 | Hopkins et al. |
| 9,296,761 B2 | 3/2016 | Chappie et al. |
| 9,321,764 B2 | 4/2016 | Wang et al. |
| 9,339,494 B2 | 5/2016 | Cooymans et al. |
| 9,353,086 B2 | 5/2016 | Savory et al. |
| 9,365,568 B2 | 6/2016 | Le Huerou et al. |
| 9,365,583 B2 | 6/2016 | Siu et al. |
| 9,388,199 B2 | 7/2016 | Altmann et al. |
| 9,464,081 B2 | 10/2016 | Flohr et al. |
| 9,469,641 B2 | 10/2016 | Hung et al. |
| 9,486,521 B2 | 11/2016 | Freeman et al. |
| 9,518,054 B2 | 12/2016 | Atkinson et al. |
| 9,550,755 B2 | 1/2017 | Hommel et al. |
| 9,598,427 B2 | 3/2017 | Le Tiran et al. |
| 9,643,964 B2 | 5/2017 | Hynd et al. |
| 9,708,323 B2 | 7/2017 | McDonald et al. |
| 9,796,713 B2 | 10/2017 | McDonald et al. |
| 9,808,542 B2 | 11/2017 | Walji et al. |
| 9,809,607 B2 | 11/2017 | Toutov et al. |
| 9,833,449 B2 | 12/2017 | Atkinson et al. |
| 9,856,264 B2 | 1/2018 | Wu et al. |
| 9,884,048 B2 | 2/2018 | Siliphaivanh et al. |
| 9,896,459 B2 | 2/2018 | Cooymans et al. |
| 9,938,276 B2 | 4/2018 | Kim et al. |
| 9,969,727 B2 | 5/2018 | Le Huerou et al. |
| 9,988,397 B2 | 6/2018 | Siliphaivanh et al. |
| 10,022,461 B2 | 7/2018 | Walji et al. |
| 10,028,954 B2 | 7/2018 | Estrada et al. |
| 10,039,755 B2 | 8/2018 | Atkinson et al. |
| 10,045,983 B2 | 8/2018 | Crawford et al. |
| 10,125,153 B2 | 11/2018 | Toutov et al. |
| 10,155,761 B2 | 12/2018 | Savory et al. |
| 10,265,323 B2 | 4/2019 | Le Tiran et al. |
| 10,508,113 B2 | 12/2019 | Argiriadi et al. |
| 10,729,680 B2 | 8/2020 | LüCking et al. |
| 10,995,091 B2 | 5/2021 | Savory et al. |
| 11,447,505 B1 | 9/2022 | Pugliese et al. |
| 2004/0039037 A1 | 2/2004 | Zhang et al. |
| 2004/0106646 A1 | 6/2004 | Takayama et al. |
| 2004/0147522 A1 | 7/2004 | Wong et al. |
| 2004/0147574 A1 | 7/2004 | Munchhof |
| 2005/0107425 A1 | 5/2005 | Rogers et al. |
| 2005/0245504 A1 | 11/2005 | Corbett et al. |
| 2006/0019984 A1 | 1/2006 | Groppi et al. |
| 2006/0194802 A1 | 8/2006 | Abdellaoui et al. |
| 2006/0217390 A1 | 9/2006 | Gunic et al. |
| 2007/0010524 A1 | 1/2007 | Zhang et al. |
| 2007/0185079 A1 | 8/2007 | Evertsson et al. |
| 2007/0219230 A1 | 9/2007 | Kim et al. |
| 2008/0300268 A1 | 12/2008 | Singh et al. |
| 2010/0004244 A1 | 1/2010 | Galve-Roperh et al. |
| 2011/0183975 A1 | 7/2011 | Goto et al. |
| 2012/0328629 A1 | 12/2012 | Freeman et al. |
| 2015/0336948 A1 | 11/2015 | Altman et al. |
| 2016/0318876 A1 | 11/2016 | Buchstaller et al. |
| 2017/0037004 A1 | 2/2017 | Crew et al. |
| 2017/0056428 A1 | 3/2017 | Wiles et al. |
| 2017/0066783 A1 | 3/2017 | Wiles et al. |
| 2017/0334906 A1 | 11/2017 | Hynd et al. |
| 2017/0334915 A1 | 11/2017 | Hynd et al. |
| 2017/0355708 A1 | 12/2017 | Jefson et al. |
| 2018/0057507 A1 | 3/2018 | Soth et al. |
| 2018/0072720 A1 | 3/2018 | Vechorkin et al. |
| 2018/0127411 A1 | 5/2018 | Siu et al. |
| 2018/0148429 A1 | 5/2018 | Fabritius et al. |
| 2018/0201580 A1 | 7/2018 | Wiles et al. |
| 2018/0222918 A1 | 8/2018 | Cremonesi et al. |
| 2018/0325992 A1 | 11/2018 | Watts et al. |
| 2018/0370972 A1 | 12/2018 | Mainolfi et al. |
| 2019/0023689 A1 | 1/2019 | Song et al. |
| 2019/0142802 A1 | 5/2019 | Kotian et al. |
| 2019/0276462 A1 | 9/2019 | Van Roosbroeck et al. |
| 2019/0300547 A1 | 10/2019 | Burgdorf et al. |
| 2019/0319199 A1 | 10/2019 | Beers |
| 2020/0131129 A1 | 4/2020 | Smith et al. |
| 2020/0131134 A1 | 4/2020 | Smith et al. |
| 2020/0131142 A1 | 4/2020 | Smith et al. |
| 2020/0339569 A1 | 10/2020 | Carceller González et al. |
| 2020/0399268 A1 | 12/2020 | Heer et al. |
| 2021/0002272 A1 | 1/2021 | Thatcher et al. |
| 2021/0024503 A1 | 1/2021 | Belema et al. |
| 2021/0024525 A1 | 1/2021 | Sydorenko et al. |
| 2021/0253569 A1 | 8/2021 | Jang et al. |
| 2021/0261537 A1 | 8/2021 | Hughes et al. |
| 2021/0261540 A1 | 8/2021 | Hughes et al. |
| 2021/0323975 A1 | 10/2021 | Guerin et al. |

FOREIGN PATENT DOCUMENTS

| | | |
|---|---|---|
| CN | 109172562 A | 1/2019 |
| CN | 109180642 A | 1/2019 |
| CN | 109223787 A | 1/2019 |
| CN | 109276571 A | 1/2019 |
| CN | 109293635 A | 2/2019 |
| CN | 109331018 A | 2/2019 |
| CN | 109336863 A | 2/2019 |
| CN | 109394766 A | 3/2019 |
| CN | 109481441 A | 3/2019 |
| CN | 109485636 A | 3/2019 |
| ES | 493457 | 7/1981 |
| GB | 1022214 A | 3/1966 |
| GB | 1476875 A | 6/1977 |
| IN | 1999DE00823 A | 1/2009 |
| JP | 2011178779 A | 9/2011 |
| JP | 2019182784 A | 10/2019 |
| WO | 1999/62890 A1 | 12/1999 |
| WO | 2003/105857 A1 | 12/2003 |
| WO | 2004039366 A1 | 5/2004 |
| WO | 2005021729 A2 | 3/2005 |
| WO | 2005/081997 A2 | 9/2005 |
| WO | 2005/082001 A2 | 9/2005 |
| WO | 2006/133417 | 12/2006 |
| WO | 2007001139 A1 | 1/2007 |
| WO | 2007082470 A1 | 7/2007 |
| WO | 2008/118626 A2 | 10/2008 |
| WO | 2008116816 A1 | 10/2008 |

(56) References Cited

FOREIGN PATENT DOCUMENTS

| | | |
|---|---|---|
| WO | 2009011546 A2 | 1/2009 |
| WO | 2010046780 A2 | 4/2010 |
| WO | 2011/019678 A1 | 2/2011 |
| WO | 2011050192 A1 | 4/2011 |
| WO | 2011071535 A2 | 6/2011 |
| WO | 2011096490 A1 | 8/2011 |
| WO | 2012065062 A1 | 5/2012 |
| WO | 2012114252 A1 | 8/2012 |
| WO | 2012/178022 A2 | 12/2012 |
| WO | 2013134766 A2 | 9/2013 |
| WO | 2013174780 A1 | 11/2013 |
| WO | 2013177367 A2 | 11/2013 |
| WO | 2014111496 A1 | 7/2014 |
| WO | 2014134349 A1 | 9/2014 |
| WO | 2014177060 A1 | 11/2014 |
| WO | 2014177524 A1 | 11/2014 |
| WO | 2015091889 A1 | 6/2015 |
| WO | 2016142310 A1 | 9/2016 |
| WO | 2018/035204 A1 | 2/2018 |
| WO | 2018044808 A1 | 3/2018 |
| WO | 2018057989 A1 | 3/2018 |
| WO | 2018107072 A1 | 6/2018 |
| WO | 2018149986 A1 | 8/2018 |
| WO | 20184210229 A1 | 11/2018 |
| WO | WO-2018198123 A1 * 11/2018 ........... A61K 31/165 | |
| WO | 2019106087 A1 | 6/2019 |
| WO | 2019/236879 A1 | 12/2019 |
| WO | 2019/236884 A1 | 12/2019 |
| WO | 2019/236890 A1 | 12/2019 |
| WO | 2020/247701 A2 | 12/2020 |
| WO | 2020252229 A2 | 12/2020 |
| WO | 2021050913 A1 | 3/2021 |
| WO | 2021142006 A1 | 7/2021 |
| WO | 2021207302 A1 | 10/2021 |
| WO | 2021207308 A1 | 10/2021 |
| WO | 2022046606 A1 | 3/2022 |
| WO | 2022125377 A1 | 6/2022 |

OTHER PUBLICATIONS

"Clinical Trial: Genentech is Now Enrolling Phase 1 Study to Test DLK Inhibitor", ALS Association, Jun. 22, 2017 (Year: 2017).*
Gerdts et al., "Sarm1-Mediated Axon Degeneration Requires Both SAM and TIR interactions", The Journal of Neuroscience, Aug. 14, 2013, vol. 33 pp. 13569-13580 (Year: 2013).*
Fischer et al., "Amyotrophic Lateral sclerosis is a distal axonopathy: evidence in mice and man", Experimental Neurology, (2004), vol. 185, pp. 232-240 (Year: 2004).*
Di Stefano, M., et al., A rise in NAD precursor nicotinamide mononucleotide (NMN) after injury promotes axon degeneration. Cell Death and Differentiation. Apr. 2015. Epub Oct. 17, 2014. vol. 22, No. 5, pp. 731-742.
Gerdts, J., e al., Sarm1-Mediated Axon Degeneration Requires Both SAM and TIR Interactions. The Journal of Neuroscience. Aug. 14, 2013. vol. 33, No. 33, pp. 13569-13580.
Summers, D.W., et al., Palmitoylation enables MAPK-dependent proteostasis of axon survival factors. Proceedings of the National Academy of Science of the United States of America, Sep. 11, 2018. ePub Aug. 27, 2018. vol. 115, No. 37, pp. E8746-E8754.
Francis et al., Pyridazino[3,4,5-de]phthalazines. II. Synthesis of nitrogen-substituted derivatives, Canadian Journal of Chemistry (1982), 60(10), 1214-32.
Francis et al., Pyridazino [3,4,5-de] phthalazines. I. Synthesis of the heterocyclic system and key intermediates, Canadian Journal of Chemistry (1979), 57(24), 3320-31.
Guzei et al., Single-crystal X-ray studies of five alkali metal salts of luminol, Journal of Coordination Chemistry (2013), 66(21), 3722-3739.
Sato et al., Chemistry of isoindoles. Novel synthesis of various functionalized isoindoles from 2,3-dicyanobenzaldehyde, Bulletin of the Chemical Society of Japan (1990), 63(4), 1160-7.

Thomas et al., Vilsmeier-Haack reaction of tertiary alcohols: formation of functionalised pyridines and naphthyridines, Journal of the Chemical Society, Perkin Transactions 1 (2001), (20), 2583-2587.
Compounds from Alchem Pharmtech Product List Catalog, Published in CAS Catalog Aug. 12, 2009, CAS registry No. 1174044-71-3, 62781-93-5, 194032-18-3, 20666-12-0, 3682-15-3, 521-31-3 (retrieved Jun. 12, 2023).
CAS RN 89898-95-3P, CAS RN 129221-92-7 (2004) retrieved Jun. 12, 2023.
CAS RN 89898-95-3P (1964) retrieved Jun. 12, 2023.
CAS RN 89898-95-3 (1967) retrieved Jun. 12, 2023.
CAS RN 404338-68-7P (2005) retrieved Jun. 12, 2023.
CAS RN 24037-01-2 (1969) retrieved Jun. 12, 2023.
CAS RN 149155-02-2 (1992) retrieved Jun. 12, 2023.
International Search Report and Written Opinion of PCT/US2019/035833 (filed on Jun. 6, 2019, by Applicant Disarm Therapeutics, Inc.); search completed on Sep. 23, 2019, mailed on Oct. 16 by the US Receiving Office; 11 pages.
Basheer. Journal of Organic Chemistry (2008), 73(4), 1386-1396.
Bhattacharyya et al. International Journal of Life Science and Pharma Research (2016), 6(1), L23-L33.
Caldwell et al. Journal of Medicinal Chemistry (2011), 54(2), 580-590.
Carlessi et al. Molecular Cancer Therapeutics (2007), 6(3), 935-944.
Chen et al. Journal of Life Sciences (2011), 5(6), 434-442.
El Abdellaoui et al. Bioorganic & Medicinal Chemistry Letters (2006), 16(21), 5561-5566.
Goerdeler et al. Chemische Berichte (1964), 97(11), 3106-17.
Gorakh et al. World Journal of Pharmaceutical Research (2014), 3(3), 3945-3974.
Hilton et al. Bioorganic & Medicinal Chemistry (2010), 18(12), 4591.
Hilton et al. Bioorganic & Medicinal Chemistry (2010), 18(2), 707-718.
Ke, Journal of Heterocyclic Chemistry (2017), 54(3), 1957-1962.
Larson et al. Bioorganic & Medicinal Chemistry Letters (2007), 17(1), 172-175.
Liu et al., Bioorganic & Medicinal Chemistry (2019), 27(4), 589-603, Synthesis and biological evaluation of 3-aryl-4-indolyl-maleimides as potent mutant isocitrate dehydrogenase-1 inhibitors.
Makida et al., Angewandte Chemie, International Edition (2016), 55(39), 11859-11862, Asymmetric Hydrogenation of Azaindoles: Chemo- and Enantioselective Reduction of Fused Aromatic Ring Systems Consisting of Two Heteroarenes.
Marcelis et al., Journal of Heterocyclic Chemistry (1987), 24(3), 545-8, Cycloaddition reactions of cyclic ketene N,S-acetals with 1,2,3,5-tetrazines.
CAS RN 88129-32-2 (1983) (retrieved Jun. 9, 2023).
Mormino et al., Organic Letters (2014), 16(6), 1744-1747, Copper-Mediated Perfluoroalkylation of Heteroaryl Bromides with (phen)CuRF.
Nechayev et al., Synthesis (2013), 45(7), 919-924, An efficient synthesis of 1-methyl-4,5,6,7- tetrahydro-1H-pyrrolo[2,3-c]pyridine and its N6-substituted analogues.
Nechayev et al., Tetrahedron (2015), 71(8), 1311-1321, Microwave-assisted acid-catalyzed nucleophilic heteroaromatic substitution: the synthesis of 7-amino-6-azaindoles.
Schwarz et al., Helvetica Chimica Acta (1951), 34, 629-41, Constitution of natural and synthetic quaternary β-carbolines, their absorption spectra, and the elucidation of the constitution of their hydrogenation products.
Semenov et al., Magnetic Resonance in Chemistry (2019), 57(7), 346-358, DFT computational schemes for 15N NMR chemical shifts of the condensed nitrogen-containing heterocycles.
Silva Junior,et al., RSC Advances (2016), 6(27), 22777-22780, Synthesis of two 'heteroaromatic rings of the future' for applications in medicinal chemistry.
Storozhenko et al., Beilstein Journal of Organic Chemistry (2018), 14, 3078-3087, Mn-mediated sequential three-component domino Knoevenagel/cyclization/Michael addition/oxidative cyclization reaction towards annulated imidazo[1,2-a]pyridines.

(56) References Cited

OTHER PUBLICATIONS

Tsuchiya et al., Chemical & Pharmaceutical Bulletin (1981), 29(6), 1539-47, Studies on diazepines. XIV. Photolysis of thieno-, furo-, and pyrrolo-[c]pyridine N-imides: formation of novel fused 1H-1,3- and 3H-2,3-diazepines.
Voskressensky et al., Tetrahedron Letters (2015), 56(46), 6475-6477, A novel domino condensation-intramolecular nucleophilic cyclization approach toward annulated imidazo-pyrrolopyridines.
Zhang et al., Synthesis (2012), 44(5), 723-730, Carbocyclic 4-deazaformycins.
Zhou et al., ChemRxiv (2019) 1-8, 2019, S(IV)-mediated unsymmetrical heterocycle cross-couplings.
Zhu et al., Bioorganic & Medicinal Chemistry (2007), 15(6), 2441-2452, Design and synthesis of pyridine-pyrazolopyridine-based inhibitors of protein kinase B/Akt.
Zhu et al., Journal of Medicinal Chemistry (2007), 50(13), 2990-3003, Syntheses of Potent, Selective, and Orally Bioavailable Indazole-Pyridine Series of Protein Kinase B/Akt Inhibitors with Reduced Hypotension.
Compounds from Alchem Pharmtech Product List Catalog, published Dec. 17, 2009; CAS Registry Nos. 76606-04-7; 52090-67-2; 1198096-55-7; 370880-82-3; and 1198096-55-7 (retrieved Jun. 9, 2023).
CAS RN 52090-67-2 (1973) (retrieved Jun. 9, 2023).
CAS RN 67058-75-7P (1978) (retrieved Jun. 9, 2023).
CAS RN 88129-32-2P (1984) (retrieved Jun. 9, 2023).
CAS RN 860297-49-0, CAS RN 1656300-54-7 (2015) (retrieved Jun. 9, 2023).
CAS RN 1580464-59-0, CAS RN 860297-49-0 (2016) (retrieved Jun. 9, 2023).
CAS RN 1621671-32-6P (2013) (retrieved Jun. 9, 2023).
CAS RN 19880-38-7, CAS RN 19880-43-4 (1967) (retrieved Jun. 9, 2023).
Foster, Hylton E. and Hurst, Jim, Journal of the Chemical Society—Perkin Transactions 1 (1973), 2901-2907, Pyrazolopyridines, Part III, Preparation and Reactions of Pyrazolo[4,3-b]pyridines.
Patel, et al., Journal of Medicinal Chemistry, Discovery of Dual Leucine Zipper Kinase (DLK, MAP3K12) Inhibitors with Activity in Neurodegeneration Models, Special Issue: New Frontiers in Kinases, rec'd Sep. 10, 2014, pp. A-R.
Siu, et al., Journal of Medicinal Chemistry, Dual Leucine Zipper Kinase Inhibitors for the Treatment of Neurodegeneration, Miniperspective, pp. A-J.
Melagraki et al. Chemical Biology & Drug Design (2010), 76(5), 397-406.
Nguyen et al. ACS Chemical Biology (2012), 7(1), 172-184.
Pasha et al. Chemical Biology & Drug Design (2009), 73(3), 292-300.
Reddy et al. Chemical Biology & Drug Design (2012), 79(1), 84-91.
Shishoo et al. Journal of Heterocyclic Chemistry (1988), 25(3), 759-65.
Silva-Santisteban et al. PLoS One (2013), 8(6), e65689.
Therese et al. Journal of Chemical Information and Modeling (2014), 54(2), 539-552.
Varaprasad et al. Bioorganic & Medicinal Chemistry Letters (2006), 16(15), 3975-3980.
Varshney et al. Medicinal Chemistry (2012), 8(3), 491-504.
Wang et al. Bioorganic & Medicinal Chemistry Letters (2013), 23(23), 6286-6291.
Yan et al. Bioorganic & Medicinal Chemistry Letters (2007), 17(1), 28-33.
CAS Registry Entries, "Chemical Catalog," Mar. 9, 2016.
CAS Registry Entries, "GVK BIO Catalog," Mar. 3, 2016.
CAS Registry Entry 1222845-17-1, European Bioinformatics Institute, May 13, 2010.
CAS Registry Entry 771583-07-4, Rare Chemicals GmbH, Oct. 29, 2004.
CAS Registry Entry 959658-93-6, National Institute of Allergy and Infectious Diseases, Dec. 28, 2007.
Pubchem, Substance Record for SID 348596632, Available Date: Dec. 18, 2017 [retrieved on Aug. 14, 2019]. Retrieved from the Internet: <URL: https://pubchem.ncbi.nlm.nih.gov/substance/348596632>.
International Search Report mailed Sep. 17, 2019, for PCT/US2019/035846, filed on Jun. 6, 2019.
Walker Lauren J et al.: "MAPK signaling promotes axonal degeneration by speeding the turnover of the axonal maintenance factor NMNAT2", ELIFE, vol. 6, Jan. 17, 2017.
Adger et al., Journal of the Chemical Society, Perkin Transactions 1: Organic and Bio- Organic Chemistry (1972-1999) (1975), (1), 31-40, 1,2,3-Benzotriazines.
Andaloussi et al., Tetrahedron Letters (2007), 48(47), 8392-8395, A convenient synthesis of linear pyridinoimidazo[1,2-a]pyridine and pyrroloimidazo[1,2-a]pyridine cores.
Andreev et al., Molecules (2019), 24(12), 2331, Design, synthesis and biological evaluation of 7-chloro-9H-pyrimido[4,5-b]lindole-based glycogen synthase kinase-3β inhibitors.
Arikawa et al., Chemical & Pharmaceutical Bulletin (2014), 62(4), 336-342, Molecular modeling, design, synthesis, and biological activity of 1H-pyrrolo[2,3-c]pyridine-7-amine derivatives as potassium-competitive acid blockers.
CAS RN 88129-32-2 (1987) (retrieved Jun. 9, 2023).
Blaszykowski et al., Journal of Organic Chemistry (2008). 73(5), 1888-1897, A palladium-catalyzed alkylation/direct arylation synthesis of nitrogen-containing heterocycles.
Bordi et al., Organic Letters (2017), 19(9), 2290-2293, Hydropyridylation of Olefins by Intramolecular Minisci Reaction.
Carbone et al., Marine Drugs (2015), 13(1), 460-492, 33 pp. CODEN: MDARE6; ISSN: 1660-3397, Synthesis and antiproliferative activity of thiazolyl-bis-pyrrolo[2,3-b]pyridines and indolyl-thiazolyl-pyrrolo[2,3-c]pyridines, nortopsentin analogues.
Chapman et al., Journal of the Chemical Society, Perkin Transactions 1: Organic and Bio-Organic Chemistry (1972-1999) (1980), (11), 2398-404, Pyrazolopyridines. Part 5. Preparation and reactions of pyrazolo[3,4-c]pyridines.
Chung et al., Journal of the American Chemical Society (2017), 139(18), 6396-6402, The Excited-State Triple Proton Transfer Reaction of 2,6-Diazaindoles and 2,6-Diazatryptophan in Aqueous Solution.
Colley et al., Journal of Medicinal Chemistry (2015), 58(23), 9309-9333, An Orally Bioavailable, Indole-3-glyoxylamide Based Series of Tubulin Polymerization Inhibitors Showing Tumor Growth Inhibition in a Mouse Xenograft Model of Head and Neck Cancer.
Duflos et al., Journal of Heterocyclic Chemistry (1973), 10(6), 1083-4, Synthesis of 1-methyl-2,3-diformylpyrrole, 1-methylpyrrolo[2,3-d]pyridazine, and 1-methyl-6-oxo-6H-cycloheptatrieno[b]pyrrole.
Georgsson et al., Journal of Medicinal Chemistry (2014), 57(14), 5935-5948, GPR103 Antagonists Demonstrating Anorexigenic Activity in Vivo: Design and Development of Pyrrolo[2,3-c]pyridines That Mimic the C-Terminal Arg-Phe Motif of QRFP26.
Gunosewoyo et al., Journal of Medicinal Chemistry (2013), 56(12), 5115-5129. Characterization of maleimide-based glycogen synthase kinase-3 (GSK-3) inhibitors as stimulators of steroidogenesis.
Henn et al., Journal of the Chemical Society, Perkin Transactions 1: Organic and Bio-Organic Chemistry (1972-1999), Formation of indoles, isoquinolines, and other fused pyridines from azidoacrylates, 1984, pp. 2189-2196.
Herz et al., Journal of the American Chemical Society (1955), 77, 6355-7, The Pomeranz-Fritsch reaction in the pyrrole series. The synthesis of apoharmine.
Hird et al., Bioorganic & Medicinal Chemistry Letters (2014), 24(7), 1820-1824, Structure-based design and synthesis of tricyclic IAP (Inhibitors of Apoptosis Proteins) inhibitors.
Hornberger et al., Bioorganic & Medicinal Chemistry Letters (2013), 23(16), 4517-4522. Discovery and optimization of 7-aminofuro[2,3-c]pyridine inhibitors of TAK1.
Huestis et al., Organic Letters (2009), 11(6), 1357-1360, Site-Selective Azaindole Arylation at the Azine and Azole Rings via N-Oxide Activation.

(56) References Cited

OTHER PUBLICATIONS

Kaji et al., Journal of Heterocyclic Chemistry (1984), 21(5), 1249-55, The synthesis of pyrazolo[3,4-d]pyridazines. Photochemical cyclization to pyrazolo[3,4-d]pyridazin-4(5H)-ones with subsequent functionalization.
Kerr et al., ACS Catalysis (2017), 7(10), 7182-7186, Site-Selective Deuteration of N-Heterocycles via Iridium-Catalyzed Hydrogen Isotope Exchange.
Kim et al., Angewandte Chemie, International Edition (2019), 58(23), 7762-7766, Regio- and Enantioselective Iridium-Catalyzed N-Allylation of Indoles and Related Azoles with Racemic Branched Alkyl-Substituted Allylic Acetates.
Kourafalos et al., Tetrahedron (2006), 62(51), 11987-11993, Synthesis and tautomerism study of 7-substituted pyrazolo[3,4-c]pyridines.
Lee et al., Bioorganic & Medicinal Chemistry Letters (2016), 26(15), 3518-3524, Synthesis and evaluation of a series of 4-azaindole-containing p21-activated kinase-1 inhibitors.
Li et al., European Journal of Medicinal Chemistry (2013), 66, 531-539, Design and synthesis of pyrido[3,2-α]carbazole derivatives and their analogues as potent antitumour agents.

* cited by examiner

INHIBITORS OF SARM1 IN COMBINATION WITH NEURO-PROTECTIVE AGENTS

CROSS REFERENCE TO RELATED APPLICATIONS

This application claims the benefit of U.S. Provisional Application No. 62/782,239, filed Dec. 19, 2018, which is herein incorporated by reference in its entirety.

SEQUENCE LISTING

The instant application contains a Sequence Listing, which has been submitted electronically in ASCII format and is hereby incorporated by reference in its entirety. The ASCII copy, created Dec. 18, 2019, is named 2012800-0029_SL.txt, and is 2,514 bytes in size.

BACKGROUND

Axonal degeneration is a hallmark of several neurological disorders including peripheral neuropathy, traumatic brain injury, and neurodegenerative diseases (Gerdts et al., SARM1 activation triggers axon degeneration locally via nicotinamide adenine dinucleotide (NAD+) destruction. Science 348 2015, pp. 453-457, hereby incorporated by reference in its entirety). Neurodegenerative diseases and injuries are devastating to both patients and caregivers. Costs associated with these diseases currently exceed several hundred billion dollars annually in the Unites States alone. Since the incidence of many of these diseases and disorders increases with age, their incidence is rapidly increasing as demographics change.

SUMMARY

Axonal degeneration after an injury is characterized by the sequential depletion of nicotinamide mononucleotide adenylyltransferase (NMNAT), NAD+ and adenosine triphosphate (ATP), followed by neurofilament proteolysis and axonal fragmentation occurring approximately 8 to 24 hours after the original injury (Gerdts, J., et al., Neuron, 2016, 89, 449-460, hereby incorporated by reference in its entirety). Following axonal damage, Sterile Alpha and TIR motif-containing 1 (SARM1) serves as the central executioner in the axonal degeneration pathway. Activated SARM1 is a highly effective NADase that depletes local axonal NAD+ reserves within minutes to a few hours after activation, leading to a local bioenergetic crisis, followed by rapid axonal degeneration. The present disclosure shows the surprising discovery that the combination of a neuroprotective agent, specifically a Dual Leucine Zipper Kinase (DLK) inhibitor or a NAMPT inhibitor, and a SARM1 inhibitor provides vastly superior and longer lasting axonal protection over the effect of either agent alone. In some embodiments, such combination provides a safe and effective approach to treat patients with axonopathies.

Accordingly, in some embodiments, the present disclosure encompasses the recognition that a combination of a DLK inhibitor and a SARM1 inhibitor maintains higher intracellular NAD+ levels, thereby preventing, ameliorating and/or decreasing the progression of axonal degeneration and cell death. In some embodiments, such combination substantially delays the pathological SARM1-mediated decrease in intracellular NAD+ that occurs as a result of SARM1 activation.

In some embodiments, the present disclosure encompasses the recognition that a combination of a NAMPT inhibitor and a SARM1 inhibitor provides greater neuroprotection than providing either treatment alone. In some embodiments, such combination inhibits the production of nicotinamide mononucleotide (NMN). In some embodiments, such combination inhibits the production of cyclic adenosine diphosphoribose (cADPR).

In some embodiments, the present disclosure provides a method for treating, preventing, and/or ameliorating a neurodegenerative disease, disorder or condition comprising administering a SARM1 inhibitor in combination with a DLK Inhibitor or a NAMPT inhibitor.

In some embodiments, a neurodegenerative disease, disorder, or condition is associated with axonal degeneration (e.g., axonal fragmentation or degradation). Accordingly, in some embodiments, the present disclosure provides a method of treating, preventing, and/or ameliorating axonal degeneration comprising administering to a subject in need thereof a SARM1 inhibitor in combination with a DLK inhibitor or a NAMPT inhibitor. In some embodiments, the axonal degeneration results from reduction or depletion of NAD+. In some embodiments, the axonal degeneration results from the accumulation of NMN. In some embodiments axonal degeneration results from the accumulation of cADPR.

In some embodiments, provided methods prevent or slow the progression of degeneration of the axon distal to an axonal injury. In some embodiments, provided methods treat or prevent secondary conditions associated with neurodegenerative disorders. Such secondary conditions include, but are not limited to, muscle impairments, respiratory impairments, anxiety, depression, speech impairments, pulmonary embolisms, cardiac arrhythmias, and/or pneumonia.

In some embodiments, the present disclosure relates to a method of treating, preventing, and/or ameliorating a neurodegenerative disease, disorder or condition comprising i) providing a) a subject diagnosed with, at risk for, or exhibiting symptoms of, a neurodegenerative disease, disorder, or condition and b) a combination comprising a SARM1 inhibitor and a DLK inhibitor or a NAMPT inhibitor; and ii) administering said combination to said subject under conditions such that said neurodegenerative disease, disorder, or condition is reduced.

In some embodiments, the present disclosure relates to a method of treating, preventing, and/or ameliorating a neurodegenerative disease, disorder or condition comprising i) providing a) a subject diagnosed with, at risk for, or exhibiting symptoms of, a neurodegenerative disease, disorder, or condition and b) a SARM1 inhibitor; and ii) administering the SARM1 inhibitor to a subject who is or has been exposed to a DLK inhibitor or a NAMPT inhibitor under conditions such that said neurodegenerative disease, disorder, or condition is reduced.

In some embodiments, the present disclosure provides a combination therapy comprising a SARM1 inhibitor and a DLK inhibitor or a NAMPT inhibitor. In some embodiments, provided combination therapies comprise a SARM1 inhibitor, a DLK inhibitor, and one or more additional therapeutic agents. In some embodiments, provided combination therapies comprise a SARM1 inhibitor, a NAMPT inhibitor, and one or more additional therapeutic agents. In some embodiments, provided combination therapies comprise a SARM1 inhibitor, a DLK inhibitor, a NAMPT inhibitor and one or more additional therapeutic agents.

In some embodiments, provided combination therapies are useful for treating, preventing, and/or ameliorating neurodegenerative diseases, disorders or conditions. In some embodiments, provided combination therapies are useful for treating, preventing, and/or ameliorating axonal degeneration. In some embodiments, provided combination therapies are useful for preventing or slowing the progression of degeneration of the axon distal to an axonal injury. In some embodiments, provided combination therapies are useful for maintaining the function of an axon including, but not limited to, metabolism, axonal integrity, intracellular transport, and axon potential propagation.

In some embodiments, a neurodegenerative disease, disorder or condition is characterized by axons that are susceptible to disruption, degeneration or pathological stress. In some embodiments, such diseases, disorders or conditions include, but are not limited to, cancer, diabetes, neurodegenerative diseases, cardiovascular disease, blood clotting, inflammation, flushing, obesity, aging, or stress.

In some embodiments, a neurodegenerative disease, disorder or condition is selected from the group consisting neuropathies or axonopathies. In some embodiments, a neuropathy or axonopathy is associated with axonal degeneration.

In some embodiments, a neuropathy associated with axonal degeneration is a hereditary or congenital neuropathy or axonopathy. In some embodiments, a neuropathy associated with axonal degeneration results from a de novo or somatic mutation. In some embodiments, a neuropathy associated with axonal degeneration results from idiopathic conditions.

In some embodiments, a neuropathy or axonopathy associated with axonal degeneration, includes, but is not limited to, Parkinson's disease, Alzheimer's disease, Herpes infection, diabetes, amyotrophic lateral sclerosis (ALS), multiple sclerosis, a demyelinating disease, ischemia or stroke, traumatic brain injury, chemical injury, thermal injury, and AIDS.

In some embodiments, a neurodegenerative disease, disorder or condition may be or comprises a traumatic neuronal injury. In some embodiments, a traumatic neuronal injury is a blunt-force trauma, a closed-head injury, an open-head injury, exposure to a concussive and/or explosive force, a penetrating injury in or to the brain cavity or innervated region of the body. In some embodiments, a traumatic neuronal injury is a force which causes axons to deform, stretch, crush or sheer.

In some embodiments, subjects to which a combination therapy as described herein is administered are suffering from or susceptible to a neurodegenerative disease, disorder or condition. In some embodiments, the subject is at risk of developing a neurodegenerative disease, disorder or condition. In some embodiments, the subject is elderly. In some embodiments, the subject has genetic risk factors for neurodegeneration.

In some embodiments, the subject is at risk of developing a disease, disorder, or condition characterized by axonal degeneration. In some embodiments, the subject has a disease, disorder, or condition characterized by axonal degeneration. In some embodiments, the subject has been diagnosed with a disease, disorder, or condition characterized by axonal degeneration. In some embodiments, the subject has not been diagnosed with a disease, disorder, or condition characterized by axonal degeneration.

In some embodiments, provided methods comprise administering a combination therapy as described herein to a subject population in need thereof. In some embodiments, the subject population is elderly. In some embodiments, the subject population has genetic risk factors for neurodegeneration.

In some embodiments, the subject population is drawn from individuals who engage in activities where the potential for traumatic neuronal injury is high. In some embodiments, the subject population is drawn from athletes who engage in contact sports or other high-risk activities.

In certain embodiments, a combination comprising a SARM1 inhibitor and a DLK inhibitor or a NAMPT inhibitor is useful, for example, as an analytical tool, as a probe in biological assays, or as a therapeutic agent in accordance with the present disclosure.

Such combinations provided by this disclosure are also useful for the study of SARM1 NADase function in biological and pathological phenomena and the comparative evaluation of new SARM1 activity inhibitors in vitro or in vivo. In some embodiments, a combination comprising a SARM1 inhibitor and a DLK inhibitor or a NAMPT inhibitor is useful for studying axonal integrity. In some embodiments, such combinations are useful for studying apoptosis.

In some embodiments, the present disclosure provides a method for inhibiting the degeneration of neurons derived from a subject comprising administering to the subject a SARM1 inhibitor in combination with a DLK inhibitor or a NAMPT inhibitor.

In some embodiments, provided combinations are useful for inhibiting the degeneration of a neuron, or a portion thereof. In some embodiments, provided combinations are useful to treat neurons whose axons are injured. In some embodiments, provided combinations are useful for inhibiting the degeneration of a neuron, or a portion thereof, in vivo. In some embodiments, provided combinations are useful as stabilizing agents to promote in vitro neuronal survival.

In some embodiments, the present disclosure relates to a method of increasing intracellular concentrations of NAD+ comprising: contacting a cell with a SARM1 inhibitor and a DLK inhibitor or a NAMPT inhibitor. In some embodiments, the present disclosure relates to a method of preventing an increase in intracellular cADPR comprising: contacting a cell with a SARM1 inhibitor and a DLK inhibitor or a NAMPT inhibitor.

In some embodiments, provided SARM1 inhibitors reduce or inhibit binding of NAD+ by SARM1. In some embodiments, provided SARM1 inhibitors bind to SARM1 within a pocket comprising one or more catalytic residues (e.g., a catalytic cleft of SARM1). In some embodiments, provided SARM1 inhibitors bind to non-catalytic residues. In some such embodiments, provided SARM1 inhibitors are allosteric modulators of SARM1 activity. Accordingly, in some embodiments, the present disclosure provides a method of reducing or inhibiting binding of SARM1 by NAD+ comprising administering to a subject in need thereof a combination of a SARM1 inhibitor and a DLK inhibitor or a NAMPT inhibitor. In some embodiments, such SARM1 inhibitor binds to one or more catalytic residues in the binding pocket of SARM1.

In some embodiments, SARM1 inhibitors and DLK inhibitors are co-administered to a subject. In some embodiments, a subject is first administered a SARM1 inhibitor followed by administration of a DLK inhibitor. In some embodiments, a DLK inhibitor is administered prior to the SARM1 inhibitor. In some embodiments, a SARM1 inhibitor is administered to a subject exposed to a DLK inhibitor.

In some embodiments, SARM1 inhibitors and NAMPT inhibitors are co-administered to a subject. In some embodiments, a subject is first administered a SARM1 inhibitor followed by administration of a NAMPT inhibitor. In some embodiments, a NAMPT inhibitor is administered prior to the SARM1 inhibitor. In some embodiments, a SARM1 inhibitor is administered to a subject exposed to a NAMPT inhibitor.

In some embodiments, provided methods and/or combination therapies inhibit activity of SARM1. Alternatively or additionally, in some embodiments, provided methods and/or combination therapies alleviate one or more attributes of neurodegeneration. In some embodiments, the present disclosure provides methods of treating, preventing, and/or ameliorating a neurodegenerative disease, disorder or condition associated with axonal degeneration.

In some embodiments, the SARM1 inhibitor is a small molecule, a polypeptide, a peptide fragment, a nucleic acid (e.g., a siRNA, an antisense oligonucleotide, a micro-RNA, or an aptamer), an antibody, a dominant-negative inhibitor, or a ribozyme.

In some embodiments, the SARM1 inhibitor is a small molecule. In some embodiments, the SARM1 inhibitor is a siRNA. In some embodiments, the SARM1 inhibitor is an antisense oligonucleotide. In some embodiments, the SARM1 inhibitor is a polypeptide. In some embodiments, a SARM1 inhibitor is a peptide fragment. In some embodiments, a SARM1 inhibitor is a nucleic acid. In some embodiments, a SARM1 inhibitor is an antisense oligonucleotide.

In some embodiments, the DLK inhibitor is a small molecule, a polypeptide, a peptide fragment, a nucleic acid (e.g., a siRNA, an antisense oligonucleotide, a micro-RNA, or an aptamer), an antibody, a dominant-negative inhibitor, or a ribozyme.

In some embodiments, the DLK inhibitor is a small molecule. In some embodiments, the DLK inhibitor is a siRNA. In some embodiments, the DLK inhibitor is an antisense oligonucleotide. In some embodiments, the DLK inhibitor is a polypeptide. In some embodiments, a DLK inhibitor is a peptide fragment. In some embodiments, a DLK inhibitor is a nucleic acid. In some embodiments, a DLK inhibitor is an antisense oligonucleotide.

In some embodiments, the NAMPT inhibitor is a small molecule, a polypeptide, a peptide fragment, a nucleic acid (e.g., a siRNA, an antisense oligonucleotide, a micro-RNA, or an aptamer), an antibody, a dominant-negative inhibitor, or a ribozyme.

In some embodiments, the NAMPT inhibitor is a small molecule. In some embodiments, the NAMPT inhibitor is a siRNA. In some embodiments, the NAMPT inhibitor is an antisense oligonucleotide. In some embodiments, the NAMPT inhibitor is a polypeptide. In some embodiments, a NAMPT inhibitor is a peptide fragment. In some embodiments, a NAMPT inhibitor is a nucleic acid. In some embodiments, a NAMPT inhibitor is an antisense oligonucleotide.

In some embodiments, a NAMPT inhibitor prevents the formation of nicotinamide mononucleotide (NMN). In some embodiments, inhibition of NAMPT inhibits the mammalian NAD+ salvage pathway.

In some embodiments, the present disclosure provides compositions that comprise and/or deliver a SARM1 inhibitor (e.g., in a form as described herein), a prodrug or active metabolite thereof. In certain embodiments, a composition comprising a SARM1 inhibitor is formulated for use in administering to a subject in combination with a DLK inhibitor or a NAMPT inhibitor.

In some embodiments, the present disclosure provides compositions comprising a SARM1 inhibitor for use in combination with a DLK inhibitor or a NAMPT inhibitor. In some embodiments, such compositions are pharmaceutical compositions that include at least one pharmaceutically acceptable carrier, diluent or excipient.

In some embodiments, the SARM1 inhibitors can be identified according to, e.g., the assays described in WO 2018/057989, published on Mar. 29, 2018, which is hereby incorporated by reference in its entirety.

BRIEF DESCRIPTION OF THE DRAWING

FIGS. 1A and 1B show the degeneration index of DRG axons at 16 hours post-axotomy. In FIG. 1A, 100 nM DLK inhibitor provided no axonal protection, whereas compound I-26 demonstrated axonal protection over all tested concentrations. The addition of 100 nM DLK inhibitor to the concentration of compound I-26 being tested provided a further, though not significant, reduction in axonal degeneration. The degeneration index of uncut axons (■), untreated cut axons (☐), axons treated with 100 nM DLK inhibitor (▨), 1.1, 3.3, 10 or 30 µM compound I-26 alone (▨), and 1.1, 3.3, 10, or 30 µM compound I-26+100 nM DLK inhibitor (▨) are indicated. In FIG. 1B, 300 nM DLK inhibitor alone and 1.1 µM alone of compound I-26 alone each provided a modest level of protection Surprisingly, the combination of 1.1 µM compound I-26+300 nM DLK inhibitor provided robust and statistically significant protection that was indistinguishable from the control uninjured axons. Furthermore, the magnitude of the combined effect of 1.1 µM compound I-26 and 300 nM DLK inhibitor was greater than the sum of the individual effects of either agent alone, indicating that the effect of combining these agents is not simply additive but in fact synergistic and could not have been predicted from the individual effect of each agent in isolation. The degeneration index of uncut axons (■), untreated cut axons (☐), axons treated with 300 nM DLK inhibitor (▨), 1.1 µM compound I-26 alone (▨), and 1.1 µM compound I-26+300 nM DLK inhibitor (▨) are indicated. Statistical significance is indicated by *($p<0.05$); ($p<0.01$); *($p<0.001$); and ****($p<0.0001$).

FIGS. 2A and 2B show the degeneration index of DRG axons at 16 hours post-axotomy. In FIG. 2A, 100 nM DLK inhibitor provided no axonal protection, whereas at 1.1 µM, compound I-86 demonstrated a small, but statistically significant amount of axonal protection. Surprisingly, the combination of 1.1 µM compound I-86+100 nM DLK inhibitor provided robust and statistically significant axonal protection that was greater than the sum of the individual effects of either agent alone. The degeneration index of uncut axons (■), untreated cut axons (□), axons treated with 100 nM DLK inhibitor (▨), 1.1 µM compound I-86 alone (▧), and 1.1 µM compound I-86+100 nM DLK inhibitor (▦) are indicated. Statistical significance is indicated by *(p<0.05); (p<0.01); *(p<0.001); and ****(p<0.0001). In FIG. 2B, 300 nM DLK inhibitor alone or 1.1 µM of compound I-86 alone provided a modest level of axonal protection. Surprisingly, the combination of 1.1 µM compound I-86+300 nM DLK inhibitor provided robust and statistically significant axonal protection. Furthermore, the magnitude of the combined effect of 1.1 µM compound I-86 and 300 nM DLK inhibitor is greater than the sum of the individual effects of either agent alone, indicating that the effect of combining these agents is not simply additive but in fact synergistic and could not have been predicted from the individual effect of each agent in isolation. The degeneration index of uncut axons (■), untreated cut axons (□), axons treated with 300 nM DLK inhibitor (▨), 1.1 µM compound I-86 alone (▧), and 1.1 µM compound I-86+300 nM DLK inhibitor (▦) are indicated. Statistical significance is indicated by *(p<0.05); (p<0.01); *(p<0.001); and ****(p<0.0001).

FIGS. 3A and 3B show the degeneration index of DRG axons at 16 hours post-axotomy. In FIG. 3A, 100 nM DLK inhibitor provided no axonal protection, whereas 1.1 or 3.3 µM compound II-6 demonstrated modest, but statistically significant axonal protection. Surprisingly, the combination of 3.3 µM compound II-6+100 nM DLK inhibitor provided robust and statistically significant protection. Furthermore, the magnitude of the combined effect of 3.3 µM compound II-6 and 100 nM DLK inhibitor is greater than the sum of the individual effects of either agent alone, and shows almost complete protection from injury, indicating that the effect of combining these agents is not simply additive but in fact synergistic and could not have been predicted from the individual effect of each agent in isolation. The degeneration index of uncut axons (■), untreated cut axons (□), axons treated with 100 nM DLK inhibitor (▨), 1.1 or 3.3 µM compound II-6 alone (▧), and 1.1 or 3.3 µM compound II-6+100 nM DLK inhibitor (▦) are indicated. Statistical significance is indicated by *(p<0.05); (p<0.01); *(p<0.001); and ****(p<0.0001). In FIG. 3B, 300 nM DLK inhibitor alone or 3.3 µM of compound II-6 alone provided a modest level of protection. The combination of 3.3 µM of compound II-6+300 nM DLK inhibitor provided robust and statistically significant protection as compared to 300 nM DLK inhibitor alone. Furthermore, the magnitude of the combined effect of 3.3 µM compound II-6 and 300 nM DLK inhibitor is greater than the sum of the individual effects of either agent alone, and shows complete protection from injury, indicating that the effect of combining these agents is not simply additive but in fact synergistic and could not have been predicted from the individual effect of each agent in isolation. The degeneration index of uncut axons (■), untreated cut axons (□), axons treated with 300 nM DLK inhibitor (▨), 1.1 or 3.3 µM compound II-6 alone (▧), and 1.1 or 3.3 µM compound II-6+300 nM DLK inhibitor (▦) are indicated. Statistical significance is indicated by *(p<0.05); (p<0.01); *(p<0.001); and ****(p<0.0001).

FIGS. 4A and 4B show the degeneration index of DRG axons at 16 hours post-axotomy. In FIG. 4A, 100 nM DLK inhibitor provided no axonal protection, whereas 0.11, 0.33 or 1.1 µM compound II-32 demonstrated a modest but not statistically significant axonal protection at these concentrations. The combination of 0.11, 0.33 or 1.1 µM compound II-32+100 nM DLK inhibitor provided greater protection than either agent alone, reaching statistical significance at 1.1 µM of compound II-32. Furthermore, the magnitude of the combined effect of 1.1 µM compound II-32 and 100 nM DLK inhibitor is greater than the sum of the individual effects of either agent alone, indicating that the effect of combining these agents is not simply additive but in fact synergistic and could not have been predicted from the individual effect of each agent in isolation. The degeneration index of uncut axons (■), untreated cut axons (□), axons treated with 100 nM DLK inhibitor (▨), 0.11, 0.33 or 1.1 µM compound II-32 alone (▧), and 0.11, 0.33 or 1.1 µM compound II-32+100 nM DLK inhibitor (▦) are indicated. Statistical significance is indicated by *(p<0.05); (p<0.01); *(p<0.001); and ****(p<0.0001). In FIG. 4B, 300 nM DLK inhibitor alone provided a modest but statistically significant level of axonal protection, whereas 0.11, 0.33 or 1.1 µM compound II-32 alone provided only slight and not statistically significant protection at these concentrations. However, the combination of 0.33 or 1.1 µM compound II-32+300 nM DLK inhibitor provided robust and statistically significant protection as compared to 300 nM DLK inhibitor alone. Furthermore, the magnitude of the combined effect of 0.33 or 1.1 µM compound II-32 and 300 nM DLK inhibitor is greater than the sum of the individual effects of either agent alone, indicating that the effect of combining these agents is not simply additive but in fact synergistic and could not have been predicted from the individual effect of each agent in isolation. The degeneration index of uncut axons (■), untreated cut axons (□), axons treated with 300 nM DLK inhibitor (▨), 0.11, 0.33 or 3.3 µM compound II-32 alone (▧), and 0.11, 0.33 or 1.1 µM compound II-32+300 nM DLK inhibitor (▦) are indicated. Statistical significance is indicated by *(p<0.05); (p<0.01); *(p<0.001); and ****(p<0.0001).

DEFINITIONS

Figure 1A:
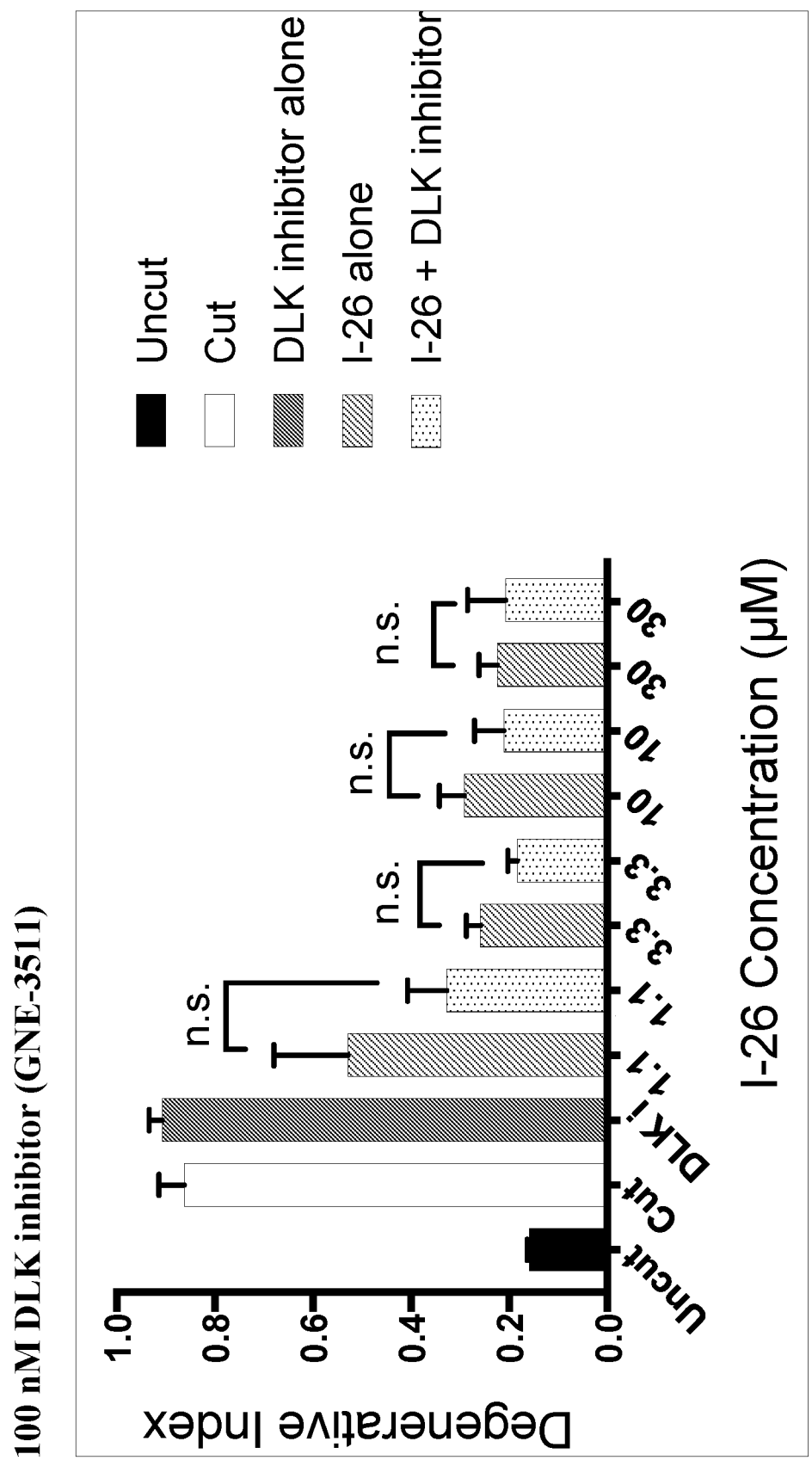
FIG. 1A and FIG. 1B illustrate that the combination of compound I-26, a SARM1 inhibitor, with the DLK inhibitor GNE-3511 increases neuroprotection post-axotomy as compared to single agent therapy. For each concentration of compound I-26 tested, the extent of axonal protection of a combination of compound I-26+DLK inhibitor was compared to the amount of protection produced by the agent in that combination that, individually, had the greater protective effect.

Binding: It will be understood that the term "binding", as used herein, typically refers to an association (e.g., a non-covalent or covalent association) between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example, nucleic acids or proteins extracted from a sample or obtained by subjecting a primary sample to techniques such as amplification or reverse transcription of mRNA, isolation and/or purification of certain components, etc.

Biomarker: The term "biomarker" is used herein to refer to a to an entity, event, or characteristic whose presence, level, degree, type, and/or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. Thus, in some embodiments, a biomarker is predictive, in some embodiments, a biomarker is prognostic, and in some embodiments, a biomarker is diagnostic, of the relevant biological event or state of interest. A biomarker may be or comprise an entity of any chemical class, and may be or comprise a combination of entities. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is detected outside of cells (e.g., is secreted or is otherwise generated or present outside of cells, e.g., in a body fluid such as blood, urine, tears, saliva, cerebrospinal fluid, etc. In some embodiments, a biomarker may be or comprise a genetic or epigenetic signature. In some embodiments, a biomarker may be or comprise a gene expression signature.

In some embodiments, a biomarker may be or comprise a marker for neurodegeneration, or for likelihood that a neurodegenerative disease, disorder or condition may develop, occur, or reoccur. In some embodiments, a biomarker may be or comprise a marker of neurodegeneration a therapeutic outcome, or likelihood thereof. Thus, in some embodiments, a biomarker is predictive, in some embodiments, a biomarker is prognostic, and in some embodiments, a biomarker is diagnostic, of a neurodegenerative disease, disorder or condition. In some embodiments changes in biomarker levels can be detected via cerebral spinal fluid (CSF), plasma and/or serum. In some embodiments a biomarker can be a detectable signal produced by medical imaging techniques including, but not limited to, magnetic resonance imaging (MRI), positron emission-tomography (PET), and/or computed tomography (CT). In some embodiments, a biomarker can be a detectable change in electrophysiological properties.

In some embodiments, neurodegeneration may be assessed, for example, by detecting an increase and/or decrease in the concentration of neurofilament light chain protein (NF-L) and/or neurofilament heavy chain protein (NF-H) contained in bodily fluids from a subject including, but not limited to, cerebral spinal fluid, blood, serum and/or plasma. In some embodiments, the incidence and/or progression of neurodegeneration can be assessed via positron emission tomography (PET) with a synaptic vesicle glycoprotein 2a (SV2A) ligand. In some embodiments, a detectable change in constitutive NAD+ and/or cADPR levels in neurons can be used to assess neurodegeneration.

In some embodiments, a detectable change in one or more neurodegeneration associated proteins in a subject, relative to a healthy reference population can be used as a biomarker of neurodegeneration. Such proteins include, but are not limited to, albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, and/or total-tau. In some embodiments, an increase in cytokines and/or chemokines, including, but not limited to, Ccl2, Ccl7, Ccl12, Csf1, and/or Il6, can be used as a biomarker of neurodegeneration.

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Combination: The terms "combination therapy" or "in combination with", as used herein, refer to those situations in which two or more different pharmaceutical agents for the treatment of disease are administered in overlapping regimens so that the subject is simultaneously exposed to at least two agents. In some embodiments, the different agents are administered simultaneously. In some embodiments, the administration of one agent overlaps the administration of at least one other agent. In some embodiments, the different agents are administered sequentially (e.g., all "doses" of a first regimen are administered prior to administration of any doses of a second regimen) such that the agents have simultaneous biologically activity within a subject. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Composition: Those skilled in the art will appreciate that the term "composition" may be used to refer to a discrete physical entity that comprises one or more specified components. In general, unless otherwise specified, a composition may be of any form e.g., gas, gel, liquid, solid, etc.

Dual Leucine Zipper Kinase (DLK) Inhibitor: The term "dual leucine zipper kinase inhibitor" or "DLK inhibitor" as used herein, refers to a compound that binds to and/or inhibits the activity of DLK. DLK, also referred to as MAP3K12, is a member of the mixed lineage kinase (MLK) family that contains an N-terminal kinase domain followed by two leucine zipper domains and a glycine/serine/proline rich C-terminal domain. In some embodiments, inhibition of DLK results in a downstream decrease in JNK phosphorylation (e.g., a decrease in JNK2 and/or JNK3 phosphorylation), JNK activity (e.g., a decrease in JNK2 and/or JNK3 activity), and/or JNK expression (e.g., a decrease in JNK2 and/or JNK3 expression). Accordingly, the inhibition of DLK can have an effect on the activity of kinase targets downstream of the DLK signaling cascade, e.g., (i) a decrease in JNK phosphorylation, INK activity, and/or INK expression, (ii) a decrease in cJun phosphorylation, cJun activity, and/or cJun expression, and/or (iii) a decrease in p38 phosphorylation, p38 activity, and/or p38 expression.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or therapeutic regimen: Those skilled in the art will appreciate that the terms "dosing regimen" and "therapeutic regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: as used herein, refers to a non-therapeutic agent that may be included in a pharmaceutical composition, for example, to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Inhibitory agent: As used herein, the term "inhibitory agent" refers to an entity, condition, or event whose presence, level, or degree correlates with decreased level or activity of a target. In some embodiments, an inhibitory agent may act directly (in which case it exerts its influence directly upon its target, for example, by binding to the target); in some embodiments, an inhibitory agent may act indirectly (in which case it exerts its influence by interacting with and/or otherwise altering a regulator of the target, so that level and/or activity of the target is reduced). In some embodiments, an inhibitory agent is one whose presence or level correlates with a target level or activity that is reduced relative to a particular reference level or activity (e.g., that observed under appropriate reference conditions, such as presence of a known inhibitory agent, or absence of the inhibitory agent in question, etc.).

Neurodegeneration: As used herein, the term "neurodegeneration" refers to a reduction in one or more features, structures, or characteristics of a neuron or neuronal tissue. In some embodiments, neurodegeneration is observed as a pathological reduction in an organism. Those skilled in the art will appreciate that neurodegeneration is associated with certain diseases, disorders and conditions, including those that affect humans. In some embodiments, neurodegeneration may be transient (e.g., as sometimes occurs in association with certain infections and/or chemical or mechanical disruptions); in some embodiments, neurodegeneration may be chronic and/or progressive (e.g., as is often associated with certain diseases, disorders or conditions such as, but not limited to, Parkinson's disease, amyotrophic lateral sclerosis, multiple sclerosis, Huntington's disease, or Alzheimer's disease). In some embodiments, neurodegeneration may be assessed, for example, by detecting in a subject an increase in a biomarker associated with neurodegeneration. In some embodiments, neurodegeneration may be assessed, for example, by detecting in a subject a decrease in a biomarker associated with neurodegeneration. Alternatively or additionally, in some embodiments, neurodegeneration may be assessed by magnetic resonance imaging (MRI), biomarkers containing cerebral spinal fluid, or other biomarkers observed in subjects. In some embodiments, neurodegeneration is defined as a score below 24 on the mini-mental state examination. In some embodiments, neurodegeneration refers to loss of synapses. In some embodiments, neurodegeneration refers to a reduction in neural tissue relating to a traumatic injury (e.g. exposure to an external force which disrupts the integrity of the neural tissue). In some embodiments, neurodegeneration refers to a reduction in peripheral neural tissue. In some embodiments, neurodegeneration refers to a reduction in central nervous tissue.

Nicotinamide phosphoribosyltransferase (NAMPT) Inhibitor: The term "Nicotinamide phosphoribosyltransferase inhibitor" or "NAMPT inhibitor" as used herein, refers to a compound that binds to and/or inhibits the activity of NAMPT. NAMPT is the rate-limiting enzyme in the Nicotinamide adenine dinucleotide (NAD+) salvage pathway that converts nicotinamide (NAM) to nicotinamide mononucleotide (NMN) in mammals. In some embodiments, inhibition of NAMPT results in a decrease of NMN. In some embodiments, a NAMPT inhibitor prevents the synthesis of NMN. In some embodiments, inhibition of NAMPT inhibits the NAMPT-dependent NAD+ salvage pathway.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intra-arterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, the active agent is present in unit dose amount appropriate for administration in a therapeutic or dosing regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prevent or prevention: As used herein, the terms "prevent" or "prevention", when used in connection with the occurrence of a disease, disorder, and/or condition, refer to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Specific: The term "specific", when used herein with reference to an agent having an activity, is understood by those skilled in the art to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments, specificity is evaluated relative to that of a reference non-specific binding agent. In some embodiments, the agent or entity does not detectably bind to the competing alternative target under conditions of binding to its target entity. In some embodiments, a binding agent binds with higher on-rate, lower off-rate, increased affinity, decreased dissociation, and/or increased stability to its target entity as compared with the competing alternative target(s).

Subject: As used herein, the term "subject" refers to an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Treat: As used herein, the terms "treat," "treatment," or "treating" refer to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example, for the purpose of decreasing the risk of developing pathology associated with the disease, disorder, and/or condition. In some embodiments, treatment may be administered to a subject to prevent the risk of developing pathology associated with or resulting from a medical procedure and/or treatment.

DETAILED DESCRIPTION OF CERTAIN EMBODIMENTS

Programmed Axonal Degeneration

Axonal degeneration is a major pathological feature of neurological diseases such as, but not limited to, Alzheimer's disease, Parkinson's disease, ALS, multiple sclerosis, diabetic peripheral neuropathy, chemotherapy-induced peripheral neuropathy, inherited neuropathy, traumatic brain injury, and/or glaucoma. Damaged or unhealthy axons are eliminated via an intrinsic self-destruction program known as Wallerian degeneration that is distinct from traditional cellular death pathways like apoptosis (Gerdts, J., et al., *Neuron*, 2016, 89, 449-460; Whitmore, A. et al., *Cell Death Differ.*, 2003, 10, 260-261, each of which is hereby incorporated by reference in its entirety). During Wallerian degeneration, a nerve undergoes selective breakdown of the axon segment distal to an injury, whereas the proximal axon segment and cell body remain intact. Axonal degeneration following an injury is characterized by the sequential depletion of NMNAT2, NAD+ and ATP, followed by neurofilament proteolysis and axonal fragmentation occurring approximately 8 to 24 hours after the original injury (Gerdts, J., et al., *Neuron,* 2016, 89, 449-460, hereby incorporated by reference in its entirety).

The discovery of the Wallerian degeneration slow (Wlds) protein, which dramatically delays axon degeneration after injury, raised hopes that blocking Wallerian degeneration would be useful in the treatment of neurological disorders (Conforti et al., *Nat Rev Neurosci.* 2014, 15(6), 394-409; Mack et al., *Nat Neurosci.* 2001, 4(12), 1199-1206, each of which is hereby incorporated by reference in its entirety). The Wlds protein blocks axon degeneration by mislocalizing the nuclear nicotinamide adenine dinucleotide (NAD+) biosynthetic enzyme NMNAT1 into axons, thereby substituting for the loss of the labile axon maintenance factor NMNAT2 and preventing the NAD+ degradation following an injury (Araki et al., *Science.* 2004, 305(5686), 1010-1013; Babetto et al., *J Neurosci.,* 2010, 30(40), 13291-13304; Gilley et al., *PLoS Biol.* 2010, 8(1), e1000300; Sasaki et al., *J Biol Chem.,* 2010, 285(53), 41211-41215, each of which is hereby incorporated by reference in its entirety). These results highlighted the importance of NAD+ in the maintenance of axonal integrity.

NAD+ is a natural coenzyme that functions as an intermediary in cellular oxidation and reduction reactions as well as an ADP-ribosyltransferase substrate. NAD+ has critical roles in energy metabolism, ATP synthesis and cellular signaling (Belenkey et al., *Trends Biochem.,* 2007, 32, 12-19; Chiarugi et al., *Nat. Rev. Cancer,* 2012, 12, 741-752, each of which is hereby incorporated by reference in its entirety). Increasing intracellular NAD+ levels can improve the health of a cell. Furthermore, the homeostatic regulation of NAD+ levels is responsible for maintaining axonal stability and integrity. Accordingly, manipulations that increase axonal localization of NMNAT, the nicotinamide adenine dinucleotide (NAD+) biosynthetic enzyme, confer axonal protection (Babetto et al., *Cell Rep.,* 2010, 3, 1422-1429; Sasaki et al., *J. Neurosci.,* 2009, each of which is hereby incorporated by reference in its entirety). Exogenous application of the NAD+ precursors that are the substrates of these enzymes, including nicotinic acid mononucleotide, nicotinamide mononucleotide, and nicotinamide riboside (NR), can also delay axonal degeneration (Sasaki et al., *J. Neurosci,* 2006, 26(33):8481-8491, which is hereby incorporated by reference in its entirety).

In most instances, the application of NAD+ or a NAD+ precursor has been found to be beneficial to a neuron following an injury. However, some studies now indicate that an aberrant increase in one direct precursor of NAD+, nicotinamide mononucleotide (NMN), rather than loss of NAD+ is responsible for mediating neurodegeneration following an injury. In fact, one study found that administering nicotinic acid riboside (NAR), a precursor of NMN, in combination with FK866, an inhibitor of the enzyme nicotinamide phosphoribosyltransferase (NAMPT) that produces NMN, protects dorsal root ganglion (DRG) axons from vincristine-induced degeneration (Lie et al., *Pro. Nat. Acad. Sci. USA.,* 2018, 115(42): 10654-10659, which is hereby incorporated by reference in its entirety). This study observed that elevation of NMN alone was not sufficient to cause degeneration, however; depressing levels of NMN confers axon protection even in the face of lower NAD+ levels. Whereas blocking NMN formation with a NAMPT inhibitor blocks the synthesis of NAD+ via the NAMPT-dependent salvage pathway, the other NAD+ synthesis pathways capable of producing NAD+ remain open. Thus, blocking NMN formation can be used to prevent axonal degeneration as well as to complement neuroprotective agents following an injury.

Pharmacological inhibition or genetic deletion of DLK is also sufficient to attenuate the neuronal injury response and can result in potent protection of neurons from degeneration in response to a range of neuronal insults (Ghosh et al., *Cell Biol.* 2011, 194, 751-764, which is hereby incorporated by reference in its entirety). Activation of DLK in neurons induces stress-specific JNK signaling via MKK4/7 and increases PERK signaling. The induction of these pathways generates a broad transcriptional injury response in neurons through the regulation of transcription factors including c-Jun and ATF4 which leads to apoptosis and axon degeneration. Thus blocking DLK activity can attenuate neuronal damage following an injury. Furthermore, it has been demonstrated that loss of DLK signaling protects neurons from excitotoxicity induced degeneration in vitro and in vivo, indicating that DLK function is not limited to axonal injury and is instead involved in the response to a range of neuronal insults (Pozniak et al., *J. Exp. Med.,* 2013, 210, 2553-2567). Thus, DLK has emerged as a druggable target for a variety of neurodegenerative disorders and diseases. It has also been recently discovered that knocking-down or eliminating the expression of SARM1 leads to long-lasting protection of sensory neurons against injury-induced axonal degeneration (Gerdts et al., *J. Neurosci,* 2013, 33, 13569-13580, which is hereby incorporated by reference in its entirety).

Activated SARM1 is a highly effective NADase that depletes local axonal NAD+ reserves within minutes to a few hours after activation, leading to a local bioenergetic crisis, followed by rapid axonal degeneration. SARM1 belongs to the myeloid differentiation primary response 88 (MYD88)-cytosolic adaptor protein family. However, SARM1 is unique among this family because it is the most evolutionary ancient adaptor, paradoxically inhibits TLR signaling, and has been identified as the central executioner of the injury-induced axon death pathway (O'Neill, L. A. & Bowie, A. G., *Nat. Rev. Immunol.,* 2007, 7, 353-364; Osterloh, J. M., et al., *Science,* 2012, 337, 481-484; Gerdts, J., et al., *J. Neurosci.* 33, 2013, 13569-13580, each of which is hereby incorporated by reference in its entirety). Activation of SARM1 via axonal injury or forced dimerization of SARM1-TIR domains promotes rapid and catastrophic depletion of Nicotinamide Adenine Dinucleotide (NAD+), followed soon after by axonal degeneration, thus highlighting the central role of NAD+ homeostasis in axonal integrity (Gerdts, J., et al., *Science,* 2015, 348, 453-457). SARM1 is required for this injury-induced NAD+ depletion both in vitro and in vivo and SARM1 activation triggers axon degeneration locally via NAD+ destruction (Gerdts et al., et al., *Science,* 2015 348, 452-457; Sasaki et al., *J. Biol. Chem.* 2015, 290, 17228-17238, each of which is hereby incorporated by reference in its entirety).

Genetic loss-of-function studies indicate that SARM1 serves as the central executioner of the axonal degeneration pathway following an injury. Genetic deletion or knockout of SARM1 allows for preservation of axons for up to 14 days after nerve transection (Osterloh, J. M., et al., *Science,* 2012, 337, 481-484; Gerdts, J., et al. *J. Neurosci.,* 2013, 33, 13569-13580, each of which is hereby incorporated by reference in its entirety) and also improves functional outcomes in mice after traumatic brain injury (Henninger, N. et al., *Brain,* 139, 2016, 1094-1105, which is hereby incorporated by reference in its entirety). In addition to the direct role SARM1 has in axonal injury, SARM1 is also required for the axonal degeneration observed in chemotherapy-induced peripheral neuropathy (CIPN). Loss of SARM1 blocks CIPN, both inhibiting axonal degeneration and heightened pain sensitivity that develops after chemotherapeutic vincristine treatment (Geisler et al, *Brain,* 2016, 139, 3092-3108, which is hereby incorporated by reference in its entirety). SARM1 contains multiple conserved motifs including SAM domains, ARM/HEAT motifs and a TIR domain that mediate oligomerization and protein-protein interactions (O'Neill, L. A. & Bowie, A. G., *Nat. Rev. Immunol.,* 2007, 7, 353-364; Tewari, R., et al., *Trends Cell Biol.,* 2010, 20, 470-481; Qiao, F. & Bowie, J. U., *Sci. STKE* 2005, re7, 2005, each of which is hereby incorporated by reference in its entirety). TIR domains are commonly found in signaling proteins functioning in innate immunity pathways where they serve as scaffolds for protein complexes (O'Neill, L. A. & Bowie, A. G., *Nat. Rev. Immunol.,* 2007, 7, 353-364, which is hereby incorporated by reference in its entirety). Interestingly, dimerization of SARM1-TIR domains is sufficient to induce axonal degeneration and to rapidly trigger degradation of NAD+ by acting as the NAD+ cleaving enzyme (Milbrandt et al., WO 2018/057989; Gerdts, J., et al., *Science,* 2015, 348, 453-457, each of which is hereby incorporated by reference in its entirety). Given the central role of SARM1 in the axonal-degeneration pathway and its identified NADase activity, efforts have been undertaken to identify agents that can regulate SARM1, and potentially act as useful therapeutic agents, for example, to protect against neurodegenerative diseases including peripheral neuropathy, traumatic brain injury, and/or neurodegenerative diseases. SARM1-dependent NAD+ consumption is the central biochemical event in the axonal degeneration program. Among other things, the present disclosure provides methods for inhibiting SARM1. Among other things, the present disclosure provides a combination of a SARM1 inhibitor and a DLK inhibitor or a NAMPT inhibitor for use in stabilizing neurons whose axons have been injured. In some embodiments, such combinations allow the axons to be repaired rather than degenerate.

Methods of Treating Neurodegeneration

DLK is a member of the mixed lineage kinase (MLK) family that contains an N-terminal kinase domain followed by two leucine zipper domains and a glycine/serine/proline rich C-terminal domain. Palmitoylation of DLK is required for proper function in neurons. Activation of DLK in neurons induces stress-specific JNK signaling via MKK4/7 and increases PERK signaling. In some embodiments, a DLK inhibitor is a dominant-negative inhibitor of DLK.

NAMPT is the rate-limiting enzyme in the Nicotinamide adenine dinucleotide (NAD+) salvage pathway that converts nicotinamide (NAM) to nicotinamide mononucleotide (NMN) in mammals. In some embodiments, inhibition of NAMPT results in a decrease of NMN. In some embodiments, a NAMPT inhibitor prevents the synthesis of NMN. In some embodiments a NAMPT inhibitor is a dominant negative inhibitor of NAMPT. In some embodiments, inhibition of NAMPT inhibits the NAMPT-dependent NAD+ salvage pathway. In some embodiments the present disclosure provides compounds that inhibit NAMPT.

In some embodiments, the present disclosure provides a method for treating subjects suffering from one or more diseases, disorders, or conditions. In some embodiments, the one or more diseases, disorders, or conditions are mediated by SARM1.

In some embodiments, the one or more diseases, disorders, or conditions is/are acute. In some embodiments, the one or more diseases, disorders, or conditions is/are chronic.

In some embodiments, the one or more diseases, disorders, or conditions is/are characterized by axonal degeneration in the central nervous system, the peripheral nervous system, the optic nerve, the cranial nerves, or a combination thereof.

In some embodiments, provided combination therapies and methods promote the increase of intracellular levels of nicotinamide adenine dinucleotide (NAD+) in cells and tissues for improving cell and tissue survival. In some embodiments, provided combination therapies methods increase NAD+ levels in cells and tissues. In some embodiments, provided combination therapies and methods improve cell and tissue survival. In some embodiments, provided combination therapies and methods stabilize the neurons and/or cells until the external environment stabilizes following an acute event.

In some embodiments, the present disclosure provides a method for treating, preventing, and/or ameliorating a neurodegenerative disease, disorder or condition comprising administering a SARM1 inhibitor and a DLK inhibitor or a NAMPT inhibitor. In some embodiments, a neurodegenerative disease, disorder or condition is associated with axonal degeneration. Accordingly, in some embodiments, the present disclosure provides a method of for treating, preventing, and/or ameliorating axonal degeneration comprising administering to a subject in need thereof a SARM1 inhibitor in combination with a DLK inhibitor or a NAMPT inhibitor.

In some embodiments, provided combination therapies and/or methods prevent or slow the degeneration of a neuron, a part of an intact neuron, or a cellular fragment derived from a neuron. In some embodiments, provided combinations and/or methods prevent or slow the progression of degeneration of the portion of the axon distal to an axonal injury. In some embodiments, provided methods and/or combinations, as described herein, are useful as stabilizing agents to promote neuronal survival. In some embodiments, provided combination therapies are useful for maintaining the function of an axon including, but not limited to, metabolism, axonal integrity, intracellular transport, and action potential propagation.

In some embodiments, provided methods treat or prevent secondary conditions associated with neurodegenerative disorders. Such secondary conditions include, but not limited to, muscle impairments, respiratory impairments, anxiety, depression, speech impairments, pulmonary embolisms, cardiac arrhythmias, and/or pneumonia.

In some embodiments, the present disclosure relates to a method of treating, preventing, and/or ameliorating a neurodegenerative disease, disorder or condition comprising i) providing a) a subject diagnosed with, at risk for, or exhibiting symptoms of, a neurodegenerative disease, disorder or condition and b) a combination comprising a SARM1 inhibitor and a DLK inhibitor or a NAMPT inhibitor; and ii) administering said combination to said subject under conditions such that said neurodegenerative disease, disorder or condition is reduced.

In some embodiments, the present disclosure provides a combination therapy comprising a SARM1 inhibitor and a DLK inhibitor or a NAMPT inhibitor. In some embodiments, provided combination therapies comprise a SARM1 inhibitor, a DLK inhibitor or a NAMPT inhibitor and one or more additional therapeutic agents.

In some embodiments, a provided combination therapy comprises a SARM1 inhibitor, a DLK inhibitor or a NAMPT inhibitor and one or more additional therapeutic agents. In some embodiments, the one or more additional therapeutic agents is/are selected from acetylcholine esterase inhibitors, NMDA agonists, Donepezil, Galantamine, Memantine, Rivastigmine, rilzuole, edaravone, levodopa, carbidopa, anticholinergics, bromocriptine, pramipexole, ropinirole, and/or amantadine. In some embodiments, the one or more additional therapeutic agents is/are selected from immunosuppressive drugs such as prednisone, cyclosporine, or azathioprine, and nonsteroidal anti-inflammatory drugs (NSAIDs). In some embodiments, the one or more additional therapeutic agents include antidepressants, anticonvulsants, antiarrythmics (e.g., mexiletine), and narcotic agents, tricyclic antidepressants such as amitriptyline or newer serotonin-norepinephrine reuptake inhibitors such as duloxetine hydrochloride or venlafaxine. In some embodiments anticonvulsants are one of the following: gabapentin, pregabalin, topiramate, and carbamazepine. In some embodiments, the one or more additional therapeutic agents combined with the present disclosure include anti-epileptic treatments. In some embodiments, the one or more additional therapeutic agents is intravenous immuonoglobin (IV Ig). In some embodiments, the one or more additional therapeutic agents is/are selected from multiple sclerosis disease-modifying therapeutics (DMTs) including, but not limited to, interferon beta-1a, interferon beta-lb, glatiramer acetate, daclizumab, teriflunomide, fingolimod, dimethyl fumarate, alemtuzumab, mitoxantrone, ocrelizumab, and natalizumab.

In some embodiments, such combination therapies are useful for treating, preventing, and/or ameliorating a neurodegenerative disease, disorder or condition. In some embodiments, provided combination therapies are useful for treating, preventing, and/or ameliorating axonal degeneration. In some embodiments, provided combination therapies are useful for preventing or slowing the progression of degeneration of the axon distal to an axonal injury.

In some embodiments, a neurodegenerative disease, disorder or condition is characterized by axons that are susceptible to disruption or pathologic stress. Such diseases or conditions include, but are not limited to, cancer, diabetes, neurodegenerative diseases, cardiovascular disease, blood clotting, inflammation, flushing, obesity, aging, or stress.

In some embodiments, a neurodegenerative disease, disorder or condition is selected from the group consisting of a neuropathy or an axonopathy. In some embodiments, an axonopathy or a neuropathy is any disease, disorder or condition involving neurons and/or supporting cells, such as for example, glia, muscle cells or fibroblasts, and, in particular, those diseases or conditions involving axonal damage. Axonal damage can be caused by traumatic injury or by non-mechanical injury due to diseases, conditions, or exposure to toxic molecules or drugs. The result of such damage can be degeneration or dysfunction of the axon and loss of functional neuronal activity. Disease and conditions producing or associated with such axonal damage are among a large number of neuropathic diseases and conditions. Such neuropathies can include peripheral neuropathies, central neuropathies, and combinations thereof. Furthermore, peripheral neuropathic manifestations can be produced by diseases focused primarily in the central nervous systems and central nervous system manifestations can be produced by essentially peripheral or systemic diseases.

In some embodiments, a neurodegenerative disease, disorder or condition may be a traumatic neuronal injury. In some embodiments, injury to the spinal cord and/or traumatic brain injury. In some embodiments, a traumatic neuronal injury is blunt force trauma, a closed-head injury, an open head injury, exposure to a concussive and/or explosive force, a penetrating injury in or to the brain cavity or innervated region of the body. In some embodiments, a traumatic neuronal injury is a force which causes axons to deform, stretch, crush or sheer. In some embodiments, a neurodegenerative disease, disorder or condition is an acute injury to the central nervous system. In some embodiments, the condition is or comprises a chronic injury to the central nervous system, e.g., injury to the spinal cord, traumatic brain injury, and/or traumatic axonal injury. In some embodiments, the condition is or comprises chronic traumatic encephalopathy (CTE). In some embodiments, a traumatic neuronal injury results from increased intraocular pressure.

In some embodiments, the neurodegenerative or neurological disease, disorder or condition is associated with axonal degeneration, axonal damage, axonopathy, a demyelinating disease, a central pontine myelinolysis, a nerve injury disease, disorder or condition, a metabolic disease, a mitochondrial disease, metabolic axonal degeneration, axonal damage resulting from a leukoencephalopathy or a leukodystrophy.

In some embodiments, a neuropathy or axonopathy is associated with axonal degeneration. In some embodiments, a neuropathy associated with axonal degeneration is a hereditary or congenital neuropathy or axonopathy. In some embodiments, a neuropathy associated with axonal degeneration results from a de novo or somatic mutation. In some embodiments, a neuropathy associated with axonal degeneration results from idiopathic conditions.

In some embodiments, provided methods as described herein are useful, for example for inhibiting or preventing degeneration of a central nervous system (neuron) or a portion thereof. In some embodiments, the present disclosure provides a combination therapy comprising a SARM1 inhibitor and a DLK inhibitor or a NAMPT inhibitor that is useful, for example as a method for inhibiting the degeneration of a peripheral nervous system neuron or a portion thereof.

In some embodiments, a peripheral neuropathy can involve damage to the peripheral nerves, and/or can be caused by diseases of the nerves or as the result of systemic illnesses. Some such diseases can include diabetes, uremia, infectious diseases such as AIDS or leprosy, nutritional deficiencies, vascular or collagen disorders such as atherosclerosis, and autoimmune diseases such as systemic lupus erythematosus, scleroderma, sarcoidosis, rheumatoid arthritis, and polyarteritis *nodosa*. In some embodiments, peripheral nerve degeneration results from traumatic (mechanical) damage to nerves as well as chemical or thermal damage to nerves. Such conditions that injure peripheral nerves include compression or entrapment injuries such as carpal tunnel syndrome, direct trauma, penetrating injuries, contusions, fracture or dislocated bones; pressure involving superficial nerves (ulna, radial, or peroneal) which can result from prolonged use of crutches or staying in one position for too long, or from a tumor; intraneural hemorrhage; ischemia; exposure to cold or radiation or certain medicines or toxic substances such as herbicides or pesticides. In particular, the nerve damage can result from chemical injury due to a cytotoxic anticancer agent such as, for example, taxol, cisplatinin, a proteasome inhibitor, or a vinca alkaloid such as vincristine. Typical symptoms of such peripheral neuropathies include weakness, numbness, paresthesia (abnormal sensations such as burning, tickling, pricking or tingling) and pain in the arms, hands, legs and/or feet. In some embodiments, a neuropathy is associated with mitochondrial dysfunction. Such neuropathies can exhibit decreased energy levels, i.e., decreased levels of NAD+ and ATP.

In some embodiments neurodegenerative diseases, disorders, or conditions that are associated with neuropathy or axonopathy in the central nervous system include diseases involving progressive dementia such as, for example, Alzheimer's disease, senile dementia, Pick's disease, and Huntington's disease; central nervous system diseases affecting muscle function such as, for example, Parkinson's disease, motor neuron, progressive ataxias, and amyotrophic lateral sclerosis; demyelinating diseases such as, for example multiple sclerosis. Mechanical injuries or traumatic injuries to the head and spine can also cause nerve injury and degeneration in the brain and spinal cord. In some embodiments, ischemia and/or stroke as well as conditions such as nutritional deficiency and chemical toxicity such as with chemotherapeutic agents can cause central nervous system neuropathies.

In some embodiments, a neuropathy or axonopathy associated with axonal degeneration, includes, but is not limited to, Parkinson's disease, Alzheimer's disease, Huntington's disease, Herpes infection, diabetes, amyotrophic lateral sclerosis (ALS), a demyelinating disease, ischemia or stroke, frontotemporal dementia, ataxias, Charcot Marie Tooth, neuromyelitis optica, traumatic brain injury, chemical injury, thermal injury, and AIDS.

In some embodiments, subjects to which a combination therapy as described herein is administered are subjects suffering from or susceptible to a neurodegenerative disease, disorder or condition. In some embodiments, the subject is at risk of developing a neurodegenerative disease, disorder or condition. In some embodiments, the present disclosure provides a method comprising administering to a subject at risk for developing a neurodegenerative disease, disorder or condition a SARM1 inhibitor in combination with a DLK inhibitor or a NAMPT inhibitor. In some embodiments, the neurodegenerative disease, disorder or condition is characterized by axonal degeneration In some embodiments, the neurodegenerative or neurological disease, disorder or condition is selected from the group consisting of spinal cord injury, stroke, multiple sclerosis, progressive multifocal leukoencephalopathy, congenital hypomyelination, encephalomyelitis, acute disseminated encephalomyelitis, central pontine myelolysis, osmotic hyponatremia, hypoxic demyelination, ischemic demyelination, adrenoleukodystrophy, Alexander's disease, Niemann-Pick disease, Pelizaeus Merzbacher disease, periventricular leukomalacia, globoid cell leukodystrophy (Krabbe's disease), Wallerian degeneration, optic neuritis, transverse myelitis, amyotrophic lateral sclerosis (ALS, Lou Gehrig's disease), Huntington's disease, Alzheimer's disease, Parkinson's disease, Tay-Sachs disease, Gaucher's disease, Hurler Syndrome, traumatic brain injury, post radiation injury, neurologic complications of chemotherapy (chemotherapy induced neuropathy; CIPN), neuropathy, acute ischemic optic neuropathy, vitamin B12 deficiency, isolated vitamin E deficiency syndrome, Bassen-Kornzweig syndrome, Glaucoma, Leber's hereditary optic atrophy (neuropathy), Leber congenital amaurosis, neuromyelitis optica, metachromatic leukodystrophy, acute hemorrhagic leukoencephalitis, trigeminal neuralgia, Bell's palsy, cerebral ischemia, multiple system atrophy, traumatic glaucoma, tropical spastic paraparesis human T-lymphotropic virus 1 (HTLV-1) associated myelopathy, west Nile virus encephalopathy, La Crosse virus encephalitis, Bunyavirus encephalitis, pediatric viral encephalitis, essential tremor, Charcot-Marie-Tooth disease, motor neuron disease, spinal muscular atrophy (SMA), hereditary sensory and autonomic neuropathy (HSAN), adrenomyeloneuropathy, progressive supra nuclear palsy (PSP), Friedrich's ataxia, hereditary ataxias, noise induced hearing loss, congenital hearing loss, age related hearing loss, Lewy Body Dementia, frontotemporal dementia, amyloidosis, diabetic neuropathy, HIV neuropathy, enteric neuropathies and axonopathies, Guillain-Barre syndrome, severe acute motor axonal neuropathy (AMAN), Creutzfeldt-Jakob disease, transmissible spongiform encephalopathy, spinocerebellar ataxias, pre-eclampsia, hereditary spastic paraplegias, spastic paraparesis, familial spastic paraplegia, French settlement disease, Strumpell-Lorrain disease, and non-alcoholic steatohepatitis (NASH).

In some embodiments, a neurodegenerative disease, disorder or condition includes conditions producing or associated with neuronal or axonal damage. Such neurodegenerative diseases, disorders or conditions can include a peripheral neuropathy, a central neuropathy, or a combination thereof. In some embodiments, a peripheral neuropathy can be produced by a disease focused primarily in the central nervous systems and a central nervous system neuropathy can be produced by essentially peripheral or systemic diseases.

In some embodiments, the neurodegenerative disease, disorder or condition is an acute peripheral neuropathy. In some embodiments an acute peripheral neuropathy is a chemotherapy-induced peripheral neuropathy (CIPN). CIPN can be induced by various drugs, such as, but not limited to, thalidomide, epothilones (e.g., ixabepilone), taxanes (e.g., paclitaxel and docetaxel), vinca alkaloids (e.g., vinblastine, vinorelbine, vincristine, and vindesine), proteasome inhibitors (e.g., bortezomib), platinum-based drugs (e.g., cisplatin, oxaliplatin, and carboplatin) and auristatins (e.g., conjugated monomethyl auristatin E).

In some embodiments, the present disclosure provides methods of treating, preventing, and/or ameliorating neurodegenerative or neurological diseases or conditions related to axonal degeneration, axonal damage, axonopathies, demyelinating diseases, central pontine myelinolysis, nerve injury diseases or disorders, metabolic diseases, mitochondrial diseases, metabolic axonal degeneration, axonal damage resulting from a leukoencephalopathy or a leukodystrophy. In some embodiments, the axonal degeneration results from reduction or depletion of NAD+.

In some embodiments, a neurodegenerative disease, disorder or condition is a central nervous system disease or disorder, a peripheral neuropathy or disorder, a disorder of the optic nerve, a metabolic disorder, a traumatic injury, viral encephalitides, exposure to toxic molecules or drugs, a neuropathy associated with pain. In some embodiments, viral encephalitides include those caused by enteroviruses, arboviruses, herpes simplex virus. In some embodiments viral encephalitides include West Nile virus encephalitis, La Crosse virus encephalitis, Bunyavirus encephalitis, pediatric viral encephalitis, and AIDS dementia complex (also known as HIV dementia, HIV encephalopathy, and HIV-associated dementia).

In some embodiments, a neurodegenerative disease, disorder or condition is associated with conditions that produce pain. Pain neuropathies that can be treated according to the methods of the disclosure include those associated with the following conditions: chronic pain, fibromyalgia, spinal pain, carpal tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, torn ligament, and diabetes.

In some embodiments, a neurodegenerative disease, disorder or condition affects the central nervous system. In some embodiments a neurodegenerative disease, disorder or condition includes, but is not limited to, Alzheimer's disease, Parkinson's disease, amyotrophic lateral sclerosis (ALS, Lou Gehrig's disease), multiple sclerosis, Huntington's disease, senile dementia, Pick's disease, Tay-Sachs disease, motor neuron disease, ataxia, spinal muscular atrophy (SMA), Bassen-Kornzweig syndrome, Charcot-Marie-Tooth disease, motor neuron disease, hereditary sensory and autonomic neuropathy (HSAN), adrenomyeloneuropathy, progressive supra nuclear palsy (PSP), and/or Friedrich's ataxia.

In some embodiments, a neurodegenerative disease, disorder or condition affects the peripheral nervous system. In some embodiments, a peripheral neuropathy can involve damage to the peripheral nerves, and/or can be caused by diseases of the nerves or as the result of systemic illnesses. In some embodiments, a peripheral neuropathy is selected from diabetes, uremia, infectious diseases such as AIDS or leprosy, nutritional deficiencies, vascular or collagen disorders such as atherosclerosis, and autoimmune diseases such as systemic lupus erythematosus, scleroderma, sarcoidosis, rheumatoid arthritis, and polyarteritis nodosa.

In some embodiments, a neurodegenerative disease, disorder or condition affects the optic nerve. In some embodiments, the condition is an acute condition affecting the optic nerve, for example, but not limited to, acute optic neuropathy (AON) or acute angle closure glaucoma. In some embodiments, the condition is a genetic or idiopathic retinal condition. In some embodiments, the condition increases intraocular pressure, such as, for example, increased intraocular pressure leading to glaucoma. In some embodiments, a neurodegenerative disease, disorder or condition is a genetic or idiopathic retinal condition, such as that resulting in axonal degeneration of, e.g., the optic nerve, resulting in loss of vision. In some embodiments, the condition is a chronic condition affecting the optic nerve, for example, but not limited to, Leber's congenital amaurosis, Leber's hereditary optic neuropathy, primary open angle glaucoma, and autosomal dominant optic atrophy.

In some embodiments, optic nerve neuropathies include, but are not limited to, glaucoma; retinal ganglion degeneration such as those associated with retinitis pigmentosa and outer retinal neuropathies; optic nerve neuritis and/or degeneration including that associated with multiple sclerosis. In some embodiments an optic neuropathy neurotraumatic injury to the optic nerve which can include, for example, injury during tumor removal. In some embodiments, an optic nerve neuropathy is a hereditary optic neuropathies such as Kjer's disease and Leber's hereditary optic neuropathy; ischemic optic neuropathies, such as those secondary to giant cell arteritis; metabolic optic neuropathies such as neurodegenerative diseases including Leber's neuropathy, nutritional deficiencies such as deficiencies in vitamins B12 or folic acid, and toxicities such as due to ethambutol or cyanide; neuropathies caused by adverse drug reactions and neuropathies caused by vitamin deficiency. Ischemic optic neuropathies also include non-arteritic anterior ischemic optic neuropathy.

In some embodiments, a neurodegenerative disease, disorder or condition is a peripheral neuropathy or peripheral nervous system disorder. In some embodiments, peripheral neuropathy is a metabolic and endocrine neuropathy which includes a wide spectrum of peripheral nerve disorders associated with systemic diseases of metabolic origin. Such diseases and disorders include, for example, diabetes mellitus, hypoglycemia, uremia, hypothyroidism, hepatic failure, polycythemia, amyloidosis, acromegaly, porphyria, disorders of lipid/glycolipid metabolism, nutritional/vitamin deficiencies, and mitochondrial disorders, among others. In some embodiments these peripheral nerve disorders can be identified by the involvement of peripheral nerves by alteration of the structure or function of myelin and axons due to metabolic pathway dysregulation.

In some embodiments, the subject is at risk of developing a condition characterized by axonal degeneration. In some embodiments, the subject is identified as being at risk of axonal degeneration, e.g., based on the subject's genotype, a diagnosis of a condition associated with axonal degeneration, and/or exposure to an agent and/or a condition that induces axonal degeneration.

In some embodiments, the subject has a condition characterized by axonal degeneration. In some embodiments, the subject has been diagnosed with a condition characterized by axonal degeneration.

In some embodiments, a combination therapy provided herein is characterized such that, when administered to a population of subjects, the combination therapy reduces one or more symptoms or features of neurodegeneration. For example, in some embodiments, a relevant symptom or feature may be selected from the group consisting of extent, rate, and/or timing of neuronal disruption.

In some embodiments, the subject engages in an activity identified as a risk factor for neuronal degeneration, e.g., a subject that engages in contact sports or occupations with a high chance for traumatic neuronal injury. In some embodiments, the contact sport includes but is not limited to American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, and/or windsurfing.

In some embodiments, provided methods comprise administering a combination therapy as described herein to a subject population in need thereof. In some embodiments the subject and/or subject population is elderly.

In some embodiments, provided combination therapies are useful, for example, in treating a population at risk of developing a condition characterized by axonal and/or neuronal degeneration. In some embodiments, the population is drawn from individuals who engage in activities where the potential for traumatic neuronal injury is high. In some embodiments, the population is drawn from athletes who engage in contact sports or other high-risk activities. In some embodiments, the subject population is drawn from those who have been a member of the armed forces or a military contractor.

In some embodiments, the subject and/or subject population is known to have a genetic risk factor for neurodegeneration. In some embodiments, the subject and/or subject population has a family history of neurodegenerative disease. In some embodiments, the subject and/or subject population expresses one or more copies of a known genetic risk factor for neurodegeneration. In some embodiments, the subject and/or subject population is drawn from a population with a high incidence of neurodegeneration. In some embodiments, the subject and/or subject population has a hexanucleotide repeat expansion in chromosome 9 open reading frame 72. In some embodiments, the subject and/or subject population has one or more copies of the ApoE4 allele.

In some embodiments, a subject to whom a provided combination therapy is administered exhibits one or more signs or symptoms associated with axonal degeneration. In some embodiments, the subject does not exhibit any signs or symptoms of neurodegeneration.

In some embodiments, the neurodegenerative disease, disorder or condition is selected from the group consisting of neuropathies or axonopathies. In some embodiments, the present disclosure provides a combination therapy comprising a SARM1 inhibitor and a DLK inhibitor or a NAMPT inhibitor to treat one or more neurodegenerative diseases, disorders or conditions selected from the group consisting of neuropathies or axonopathies. In some embodiments, the present disclosure provides a combination therapy comprising a SARM1 inhibitor and a DLK inhibitor or a NAMPT inhibitor, for example to treat a neuropathy or axonopathy associated with axonal degeneration. In some embodiments, a neuropathy associated with axonal degeneration is a hereditary or congenital neuropathy or axonopathy. In some embodiments, a neuropathy associated with axonal degeneration results from a de novo or somatic mutation. In some embodiments, a neuropathy associated with axonal degeneration results from idiopathic conditions. In some embodiments, a neuropathy associated with axonal degeneration is selected from a list contained herein.

In some embodiments, provided methods reduce one or more symptoms or features of neurodegeneration. For example, in some embodiments, a relevant symptom or feature may be selected from the group consisting of extent, rate, and/or timing of neuronal disruption. In some embodiments, neuronal disruption may be or comprise axonal degeneration, loss of synapses, loss of dendrites, loss of synaptic density, loss of dendritic arborization, loss of axonal branching, loss of neuronal density, loss of myelination, loss of neuronal cell bodies, loss of synaptic potentiation, loss of action-potential potentiation, loss of cytoskeletal stability, loss of axonal transport, loss of ion channel synthesis and turnover, loss of neurotransmitter synthesis, loss of neurotransmitter release and reuptake capabilities, loss of axon-potential propagation, neuronal hyperexitability, and/or neuronal hypoexcitability. In some embodiments, neuronal disruption is characterized by an inability to maintain an appropriate resting neuronal membrane potential. In some embodiments, neuronal disruption is characterized by the appearance of inclusion bodies, plaques, and/or neurofibrillary tangles. In some embodiments, neuronal disruption is characterized by the appearance of stress granules. In some embodiments, neuronal disruption is characterized by the intracellular activation of one or more members of the cysteine-aspartic protease (Caspase) family. In some embodiments, neuronal disruption is characterized by a neuron undergoing programed cell death (e.g. apoptosis, pyroptosis, ferroapoptosis, and/or necrosis) and/or inflammation.

In certain embodiments, a combination comprising a SARM1 inhibitor and a DLK inhibitor or a NAMPT inhibitor is useful, for example, as an analytical tool, as a probe in biological assays, or as a therapeutic agent in accordance with the present disclosure.

Such combinations provided by this disclosure are also useful for the study of SARM1 NADase function in biological and pathological phenomena and the comparative evaluation of new SARM1 activity inhibitors in vitro or in vivo. In some embodiments, a combination comprising a SARM1 inhibitor and a DLK inhibitor or a NAMPT inhibitor is useful for studying axonal integrity. In some embodiments, such combinations are useful for studying apoptosis.

In some embodiments, provided combinations are useful for inhibiting the degeneration of a neuron, or a portion thereof. In some embodiments, provided combinations are useful to treat neurons whose axons are injured. In some embodiments, provided combinations are useful for inhibiting the degeneration of a neuron, or a portion thereof in vivo. In some embodiments, provided combinations are useful as stabilizing agents to promote in vitro neuronal survival.

In some embodiments, the present disclosure provides a method for inhibiting the degeneration of neurons derived from a subject comprising administering to the subject a SARM1 inhibitor in combination with a DLK inhibitor or a NAMPT inhibitor.

In some embodiments, provided combinations are useful to treat neurons whose axons are injured.

In some embodiments, the present disclosure relates to a method of increasing intracellular concentrations of NAD+ comprising: contacting a biological sample with a SARM1 inhibitor and a DLK inhibitor or a NAMPT inhibitor. In some embodiments, the present disclosure relates to a method of preventing an increase in intracellular cADPR comprising: contacting a cell with a SARM1 inhibitor and a DLK inhibitor or a NAMPT inhibitor.

In some embodiments, the present disclosure provides a combination therapy comprising a SARM1 inhibitor and a DLK inhibitor or a NAMPT inhibitor that is useful, for example in affecting biomarkers associated with neurodegeneration. In some embodiments, changes in biomarkers can be detected systemically or with a sample of cerebral spinal fluid (CSF), blood, plasma, serum, and/or tissue from a subject. In some embodiments, provided methods described herein can be used to affect a change in the concentration of neurofilament light chain protein (NF-L) and/or neurofilament heavy chain protein (NF-H) contained in the CSF, blood, plasma, serum, and/or tissue of a subject. In some embodiments, provide methods described herein can affect constitutive NAD+ and/or cADPR levels in neurons and/or axons.

In some embodiments, provided methods comprise administering a combination therapy as described herein to a subject or subject population based on the presence or absence of one or more biomarkers. In some embodiments, provided methods further comprise monitoring the level of a biomarker in the subject and/or subject population and adjusting the dosing regimen accordingly.

In some embodiments, provided methods as described herein can affect a detectable change in the levels of one or more neurodegeneration-associated proteins in a subject. Such proteins include, but are not limited to, albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, and/or total-tau. In some embodiments, one or more compounds and/or compositions as described herein can affect a change in cytokines and/or chemokines, including, but not limited to, Ccl2, Ccl7, Ccl12, Csf1, and/or Il6.

In some embodiments, provided SARM1 inhibitors reduce or inhibit binding of NAD+ by SARM1. In some embodiments, provided SARM1 inhibitors bind to SARM1 within a pocket comprising one or more catalytic residues (e.g., a catalytic cleft of SARM1). In some embodiments, provided SARM1 inhibitors bind to non-catalytic residues. In some embodiments, provided SARM1 inhibitors are allosteric modulators of SARM1 activity. In some embodiments, provided SARM1 inhibitors reduce SARM1 NADase activity. Accordingly, in some embodiments, the present disclosure provides a method of reducing or inhibiting binding of SARM1 by NAD+ comprising administering to a subject in need thereof a combination of a SARM1 inhibitor and a DLK inhibitor or a NAMPT inhibitor.

In some embodiments, a SARM1 inhibitor and a DLK inhibitor or a NAMPT inhibitor are co-administered to a subject. In some embodiments, a SARM1 inhibitor is administered to a subject exposed to a DLK inhibitor or a NAMPT inhibitor. In some embodiments, a SARM1 inhibitor and a DLK inhibitor or a NAMPT inhibitor are each administered sequentially. In some embodiments a subject is first administered a SARM1 inhibitor followed by administration of a DLK inhibitor or a NAMPT inhibitor. In some embodiments a DLK inhibitor or a NAMPT inhibitor is administered prior to the SARM1 inhibitor. In some embodiments, a SARM1 inhibitor is administered to a subject who is or has been administered a DLK inhibitor or a NAMPT inhibitor.

In some embodiments, provided methods and/or combination therapies inhibit activity of SARM1. Alternatively or additionally, in some embodiments, provided methods and/or combination therapies alleviate one or more attributes of neurodegeneration. In some embodiments, the present disclosure provides methods of treating, preventing, and/or ameliorating a neurodegenerative disease, disorder or condition associated with axonal degeneration.

In some embodiments, the SARM1 inhibitor is a small molecule, a polypeptide, a peptide fragment, a nucleic acid (e.g., a siRNA, an antisense oligonucleotide, a micro-RNA, or an aptamer), an antibody, a dominant-negative inhibitor, or a ribozyme.

In some embodiments, the SARM1 inhibitor is a small molecule. In some embodiments, the SARM1 inhibitor is a siRNA. In some embodiments, the SARM1 inhibitor is an antisense oligonucleotide. In some embodiments, the SARM1 inhibitor is a polypeptide. In some embodiments, a SARM1 inhibitor is a peptide fragment. In some embodiments, a SARM1 inhibitor is a nucleic acid. In some embodiments, a SARM1 inhibitor is an antisense oligonucleotide.

In some embodiments, the DLK inhibitor is a small molecule, a polypeptide, a peptide fragment, a nucleic acid (e.g., a siRNA, an antisense oligonucleotide, a micro-RNA, or an aptamer), an antibody, a dominant-negative inhibitor, or a ribozyme.

In some embodiments, the DLK inhibitor is a small molecule. In some embodiments, the DLK inhibitor is a siRNA. In some embodiments, the DLK inhibitor is an antisense oligonucleotide. In some embodiments, the DLK inhibitor is a polypeptide. In some embodiments, a DLK inhibitor is a peptide fragment. In some embodiments, a DLK inhibitor is a nucleic acid. In some embodiments, a DLK inhibitor is an antisense oligonucleotide.

In some embodiments, the NAMPT inhibitor is a small molecule, a polypeptide, a peptide fragment, a nucleic acid (e.g., a siRNA, an antisense oligonucleotide, a micro-RNA, or an aptamer), an antibody, a dominant-negative inhibitor, or a ribozyme.

In some embodiments, the NAMPT inhibitor is a small molecule. In some embodiments, the NAMPT inhibitor is a siRNA. In some embodiments, the NAMPT inhibitor is an antisense oligonucleotide. In some embodiments, the NAMPT inhibitor is a polypeptide. In some embodiments, a NAMPT inhibitor is a peptide fragment. In some embodiments, a NAMPT inhibitor is a nucleic acid. In some embodiments, a NAMPT inhibitor is an antisense oligonucleotide.

In some embodiments, the present disclosure provides compositions that comprise and/or deliver a SARM1 inhibitor (e.g., in a form as described herein), a prodrug or active metabolite thereof. In certain embodiments, a composition comprising a SARM1 inhibitor is formulated for use in administering to a subject in combination with a DLK inhibitor or a NAMPT inhibitor.

In some embodiments, provided methods and/or combination therapies promote the increase of intracellular levels of nicotinamide adenine dinucleotide (NAD+) in cells and tissues for improving cell and tissue survival. In some embodiments, provided methods and/or combination therapies prevent a decrease in NAD+ levels in cells and/or tissues. In some embodiments, provided methods and/or combination therapies reduce NAD+ catabolism. In further embodiments, provided methods and/or combination therapies increase NAD+ levels in cells and tissues and for improving cell and tissue survival. In some embodiments, provided methods reduce or inhibit the ability of SARM1 to efficiently bind to NAD+. In some embodiments, provided methods inhibit SARM1 via a dominant-negative mechanism. In some embodiments, provided combination therapies and/or methods stabilize the neurons and/or cells until the external environment stabilizes following an acute event.

In some embodiments, the present disclosure provides compositions comprising a SARM1 inhibitor for use in combination with a DLK inhibitor or a NAMPT inhibitor. In some embodiments, such compositions are pharmaceutical compositions that include at least one pharmaceutically acceptable carrier, diluent or excipient. In some embodiments, the present disclosure provides compositions that comprise and/or deliver a compound including a SARM1 inhibitor with a DLK inhibitor or a NAMPT inhibitor. In some embodiments, such compositions are pharmaceutically acceptable compositions that include at least one pharmaceutically acceptable carrier.

SARM1 Inhibitors

In some embodiments, the SARM1 inhibitor is a small molecule, a polypeptide, a peptide fragment, a nucleic acid (e.g., a siRNA, an antisense oligonucleotide, a micro-RNA, or an aptamer), an antibody, a dominant-negative inhibitor, or a ribozyme.

In some embodiments, the SARM1 inhibitor is a small molecule. In some embodiments, the SARM1 inhibitor is a siRNA. In some embodiments, the SARM1 inhibitor is an antisense oligonucleotide. In some embodiments, the SARM1 inhibitor is a polypeptide. In some embodiments, a SARM1 inhibitor is a peptide fragment. In some embodiments, a SARM1 inhibitor is a nucleic acid. In some embodiments, a SARM1 inhibitor is an antisense oligonucleotide.

In some embodiments, provided SARM1 inhibitors bind to SARM1 within a pocket comprising one or more catalytic residues (e.g., a catalytic cleft of SARM1). In some embodiments, provided SARM1 inhibitors inhibit SARM1 activity by binding to an allosteric site.

i. Small Molecule SARM1 Inhibitors

In some embodiments, the SARM1 inhibitor is a small molecule.

In some embodiments, the SARM1 inhibitor is selected from a compound of formula I, II, or III:

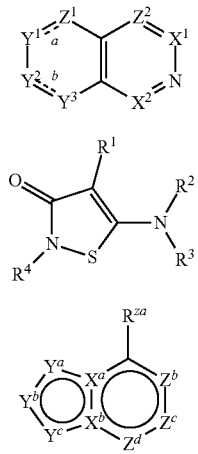

or a pharmaceutically acceptable salt thereof, wherein each of $X^1$, $X^2$, $Y^1$, $Y^2$, $Y^3$, $Z^1$, $Z^2$, $\overset{a}{=\!=\!=}$, $\overset{b}{=\!=\!=}$, $R^1$, $R^2$, $R^3$, $R^4$, $X^a$, $X^b$, $Y^a$, $Y^b$, $Y^c$, $Z^b$, $Z^c$, $Z^d$ and $R^{za}$ is as defined, infra.

In some embodiments, the SARM1 inhibitor is a compound of formula I:

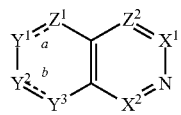
I or a pharmaceutically acceptable salt thereof, wherein:
each of $\overset{a}{=\!=\!=}$ and $\overset{b}{=\!=\!=}$ independently a single or double bond;
$X^1$ is selected from N and C—$R^{x1}$;
$R^{x1}$ is selected from halogen, —CN, —R', and —OR';
$X^2$ is selected from N and C—$R^{x2}$;
$R^{x2}$ is selected from halogen, —CN, —R', —OR', —N(R')$_2$, —SO$_2$R', —C(O)R', —N(R')SO$_2$R', —SO$_2$N(R')$_2$, —OC(O)R', —C(O)OR', —N(R')C(O)R', —C(O)N(R')$_2$, and N(R')C(O)N(R')$_2$;
$Y^1$ is selected from N and C—$R^{y1}$ when $\overset{a}{=\!=\!=}$ is a double bond or $Y^1$ is CH($R^{y1}$) or C($R^{y1}$)$_2$ when $\overset{a}{=\!=\!=}$ is a single bond;
$R^{y1}$ is selected from halogen, —CN, —R', —OR', and N(R')$_2$;
$Y^2$ is selected from N and C—$R^{y2}$ when $\overset{b}{=\!=\!=}$ is a double bond or $Y^2$ is selected from N—R' and C(O) when $\overset{b}{=\!=\!=}$ is a single bond;
$Y^3$ is selected from N and C—$R^{y3}$ when $\overset{b}{=\!=\!=}$ double bond or $Y^3$ is selected from N—R' and C(O) when $\overset{b}{=\!=\!=}$ is a single bond;
each $R^{y2}$ and $R^{y3}$ is independently selected from halogen, —CN, —R', —OR' and —N(R')$_2$; and $Z^1$ is selected from N and C—$R^{z1}$ when $\overset{a}{=\!=\!=}$ is a double bond or $Z^1$ is CH($R^{z1}$) or C($R^{z1}$)$_2$ when $\overset{a}{=\!=\!=}$ is a single bond;
$R^{z1}$ is selected from halogen, —CN, —NO$_2$, —R', —(C$_{1-6}$ alkylene)OR', —(C$_{1-6}$ alkylene)N(R')$_2$, —OR', —SR', —SF$_5$, —N(R')$_2$, —C(O)R', —C(O)OR', —OC(O)R', —C(O)N(R')$_2$, —N(R')C(O)R', —SOR', —SO$_2$R', —N(R)SO$_2$R', and —SO$_2$N(R')$_2$;
$Z^2$ is selected from N and C—$R^{z2}$;
$R^2$ is selected from halogen, —CN, —R', —OR', and —N(R')$_2$; and
each R' is independently selected from hydrogen, C$_{1-6}$ alkyl, C$_{2-6}$ alkenyl, and C$_{2-6}$ alkynyl, wherein each of C$_{1-6}$ alkyl, C$_{2-6}$ alkenyl, or C$_{2-6}$ alkynyl is optionally substituted with halogen; or:
two instances of R', together with the nitrogen atom to which they are attached, form a 3- to 6-membered saturated or partially unsaturated heterocyclic ring.

In some embodiments, the SARM1 inhibitor is a compound of formula I:

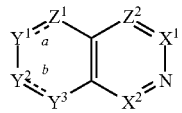
I or a pharmaceutically acceptable salt thereof, wherein:
each of $\overset{a}{=\!=\!=}$ and $\overset{b}{=\!=\!=}$ is independently a single or double bond;
$X^1$ is selected from N and C—$R^{x1}$;
$R^{x1}$ is selected from halogen, —CN, —R', and —OR';
$X^2$ is selected from N and C—$R^{x2}$;
$R^{x2}$ is selected from halogen, —CN, —R', —OR', —N(R')$_2$, —SO$_2$R', —C(O)R', —N(R')SO$_2$R', —SO$_2$N(R')$_2$, —OC(O)R', —C(O)OR', —N(R')C(O)R, —C(O)N(R')$_2$, and —N(R')C(O)N(R')$_2$;
$Y^1$ is selected from N and C—$R^{y1}$ when $\overset{a}{=\!=\!=}$ is a double bond or $Y^1$ is CH($R^{y1}$) or C($R^{y1}$)$_2$ when $\overset{a}{=\!=\!=}$ is a single bond;
$R^{y1}$ is selected from halogen, —CN, —R', —OR, and —N(R')$_2$;
$Y^2$ is selected from N and C—$R^{y2}$ when $\overset{b}{=\!=\!=}$ is a double bond or $Y^2$ is selected from N—R' and C(O) when $\overset{b}{=\!=\!=}$ is a single bond;
$Y^3$ is selected from N and C—$R^{y3}$ when $\overset{b}{=\!=\!=}$ is a double bond or $Y^3$ is selected from N—R' and C(O) when $\overset{b}{=\!=\!=}$ is a single bond;
each $R^{y2}$ and $R^{y3}$ is independently selected from halogen, —CN, —R', —OR' and —N(R')$_2$; and
$Z^1$ is selected from N and C—$R^{z1}$ when $\overset{a}{=\!=\!=}$ is a double bond or $Z^1$ is CH($R^{z1}$) or C($R^{z1}$)$_2$ when $\overset{a}{=\!=\!=}$ is a single bond;
$R^{z1}$ is selected from halogen, —CN, —NO$_2$, —R', —(C$_{1-6}$ alkylene)OR', —(C$_{1-6}$ alkylene)N(R')$_2$, —OR', —SR', —SF$_5$, —N(R')$_2$, —C(O)R', —C(O)OR', —OC(O)R', —C(O)N(R')$_2$, —N(R')C(O)R', —SOR', —SO$_2$R'', —N(R')SO$_2$R', and —SO$_2$N(R')$_2$;

$Z^2$ is selected from N and C—$R^{z2}$;
$R^{z2}$ is selected from halogen, —CN, —R', —OR', and —N(R')$_2$; and
each R' is independently selected from hydrogen, $C_{1-6}$ alkyl, $C_{2-6}$ alkenyl, and $C_{2-6}$ alkynyl, wherein each of $C_{1-6}$ alkyl, $C_{2-5}$ alkenyl, or $C_{2-6}$ alkynyl is optionally substituted with halogen; or:
two instances of R', together with the nitrogen atom to which they are attached, form a 3- to 6-membered saturated or partially unsaturated heterocyclic ring.

As defined generally above for formula I, each of $\stackrel{a}{===}$ and $\stackrel{b}{===}$ is independently a single or double bond. In some embodiments of formula I, each of $\stackrel{a}{===}$ and $\stackrel{b}{===}$ is a double bond. In some embodiments of formula I, each of $\stackrel{a}{===}$ and $\stackrel{b}{===}$ is a single bond. In some embodiments of formula I, $\stackrel{a}{===}$ is a single bond and $\stackrel{b}{===}$ is a double bond. In some embodiments of formula I, $\stackrel{a}{===}$ is a double bond and $\stackrel{b}{===}$ is a single bond.

It will be appreciated that compounds of formula I having the structure

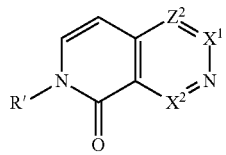

can exist in two tautomeric forms when R' is H:

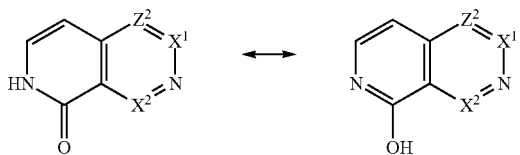

Accordingly, it will be appreciated that compounds of formula I wherein $Y^2$ is N—H and $Y^3$ is C(O) can be drawn in either tautomeric form.

Similarly, compounds of formula I having the structure

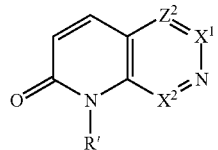

can exist in two tautomeric forms when R' is H:

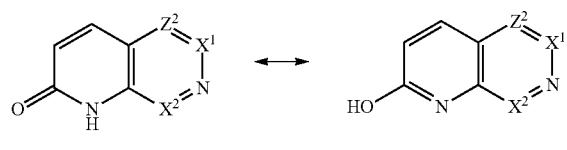

Accordingly, it will be appreciated that compounds of formula I wherein $Y^2$ is C(O) and $Y^3$ is N—H can be drawn in either tautomeric form.

As defined generally above for formula I, $X^1$ is selected from N and C—$R^{x1}$. In some embodiments of formula I, $X^1$ is N. In some embodiments of formula I, $X^1$ is C—$R^{x1}$.

As defined generally above for formula I, $R^{x1}$ is selected from halogen, —CN, —R', and —OR'. In some embodiments of formula I, $R^{x1}$ is —R'. In some such embodiments of formula I, R' is H. Accordingly, in some embodiments of formula I, $R^{x1}$ is H. In some embodiments of formula I, $R^{x1}$ is —R', wherein R' is —$C_{1-6}$ alkyl. In some embodiments of formula I, $R^{x1}$ is —R', wherein R' is —CH$_3$. Accordingly, in some embodiments of formula I, $R^{x1}$ is —CH$_3$.

In some embodiments of formula I, $R^{x1}$ is —OR'. In some embodiments of formula I, $R^{x1}$ is —OR, wherein R is H. Accordingly, in some embodiments of formula I, $R^{x1}$ is —OH.

As defined generally above for formula I, $X^2$ is selected from N and C—$R^{x2}$. In some embodiments of formula I, $X^2$ is N. In some embodiments of formula I, $X^2$ is C—$R^{x2}$.

As defined generally above for formula I, $R^2$ is selected from halogen, —CN, —R', —OR', —N(R')$_2$, —SO$_2$R', —C(O)R', —N(R')SO$_2$R', —SO$_2$N(R')$_2$, —OC(O)R', —C(O)OR', —N(R')C(O)R', —C(O)N(R')$_2$, and —N(R')C(O)N(R')$_2$. In some embodiments of formula I, $R^{x2}$ is —R'. In some such embodiments of formula I, R' is H. Accordingly, in some embodiments of formula I, $R^{x2}$ is H. In some embodiments of formula I, $R^{x2}$ is —R', wherein R' is —$C_{1-6}$ alkyl. In some embodiments of formula I, $R^{x2}$ is —R', wherein R' is —CH$_3$. Accordingly, in some embodiments of formula I, $R^{x2}$ is —CH$_3$.

In some embodiments of formula I, $R^{x2}$ is halogen. In some embodiments of formula I, $R^{x2}$ is chloro.

In some embodiments of formula I, $R^{x2}$ is —N(R')SO$_2$R'. In some embodiments of formula I, $R^{x2}$ is —NHSO$_2$R'. In some such embodiments of formula I, R' is —$C_{1-6}$ alkyl. In some embodiments of formula I, $R^{x2}$ is —NHSO$_2$R', wherein R' is —CH$_3$. In some embodiments of formula I, $R^{x2}$ is —NHSO$_2$R', wherein R' is —CH$_2$CH$_3$. In some embodiments of formula I, $R^{x2}$ is —NHSO$_2$R', wherein R' is cyclopropyl.

In some embodiments of formula I, $R^{x2}$ is —N(R')$_2$. In some such embodiments of formula I, each R' is H. Accordingly, in some embodiments of formula I, $R^{x2}$ is —NH$_2$. In some embodiments of formula I, $R^{x2}$ is —N(R')$_2$, wherein each R' is independently selected from H and —$C_{1-6}$ alkyl. In some embodiments of formula I, $R^{x2}$ is —N(R')$_2$, wherein each R' is independently selected from H and —CH$_3$. In some embodiments of formula I, $R^{x2}$ is —NHCH$_3$. In some embodiments, $R^{x2}$ is —N(CH$_3$)$_2$.

In some embodiments of formula I, $R^{x2}$ is —OR'. In some such embodiments of formula I, R' is H. Accordingly, in some embodiments of formula I, $R^{x2}$ is —OH. In some embodiments of formula I, $R^2$ is —OR', wherein R' is —$C_{1-6}$ alkyl. In some embodiments of formula I, $R^{x2}$ is —OR', wherein R' is —CH$_3$. Accordingly, in some embodiments of formula I, $R^{x2}$ is —OCH$_3$.

In some embodiments of formula I, $R^{x2}$ is —N(R')C(O)N(R')$_2$. In some such embodiments of formula I, each R' is independently selected from H and —$C_{1-6}$ alkyl. In some embodiments of formula I, $R^{x2}$ is —N(R')C(O)N(R')$_2$, wherein each R' is independently selected from H and —CH$_3$. In some embodiments of formula I, $R^{x2}$ is —NHC(O)NHCH$_3$.

As defined generally above for formula I, $Y^1$ is selected from N and C—$R^{y1}$ when $\overset{a}{=\!=\!=}$ is a double bond or $Y^1$ is CH($R^{y1}$) or C($R^{y1}$)$_2$ when $\overset{a}{=\!=\!=}$ is a single bond. In some embodiments of formula I, $\overset{a}{=\!=\!=}$ is a double bond and $Y^1$ is N. In some embodiments of formula I, $\overset{a}{=\!=\!=}$ is a double bond and $Y^1$ is C—$R^{y1}$. In some embodiments of formula I, $\overset{a}{=\!=\!=}$ is a single bond and $Y^1$ is CH($R^{y1}$). In some embodiments of formula I, $\overset{a}{=\!=\!=}$ is a single bond and $Y^1$ is C($R^{y1}$)$_2$.

As defined generally above for formula I, $R^{y1}$ is selected from halogen, —CN and —R'. In some embodiments of formula I, $R^{y1}$ is —R'. In some such embodiments of formula I, —R' is H. Accordingly, in some embodiments of formula I, $R^{y1}$ is H. In some embodiments of formula I, $R^{y1}$ is —N(R')$_2$. In some embodiments of formula I, $R^{y1}$ is —NH$_2$. In some embodiments of formula I, $R^{y1}$ is —OR'. In some embodiments of formula I, $R^{y1}$ is —OCH$_3$. In some embodiments of formula I, $R^{y1}$ is —OH. In some embodiments of formula I, $R^{y1}$ is halogen. In some such embodiments of formula I, $R^{y1}$ is fluoro or bromo.

As defined generally above for formula I, $Y^2$ is selected from N and C—$R^{y2}$ when $\overset{b}{=\!=\!=}$ is a double bond or $Y^2$ is selected from N—R' and C(O) when $\overset{b}{=\!=\!=}$ is a single bond. In some embodiments of formula I, $\overset{b}{=\!=\!=}$ is a double bond and $Y^2$ is N. In some embodiments of formula I, $\overset{b}{=\!=\!=}$ is a double bond and $Y^2$ is C—$R^{y2}$. In some embodiments of formula I, $\overset{b}{=\!=\!=}$ is a single bond and $Y^2$ is N—R'. In some embodiments of formula I, $\overset{b}{=\!=\!=}$ is a single bond and $Y^2$ is C(O).

As defined generally above for formula I, $Y^3$ is selected from N and C—$R^{y3}$ when $\overset{b}{=\!=\!=}$ is a double bond or $Y^3$ is selected from N—R' and C(O) when $\overset{b}{=\!=\!=}$ is a single bond. In some embodiments of formula I, $\overset{b}{=\!=\!=}$ is a double bond and $Y^3$ is N. In some embodiments of formula I, $\overset{b}{=\!=\!=}$ is a double bond and $Y^3$ is C—$R^{y3}$. In some embodiments of formula I, $\overset{b}{=\!=\!=}$ is a single bond and $Y^3$ is N—R'. In some embodiments of formula I, $\overset{b}{=\!=\!=}$ is a single bond and $Y^3$ is C(O).

As defined generally above for formula I, each $R^{y2}$ and $R^{y3}$ is independently selected from halogen, —CN, —R', —OR' and —N(R')$_2$. In some embodiments of formula I, $R^{y2}$ is —R'. In some such embodiments of formula I, —R' is H. Accordingly, in some embodiments of formula I, $R^{y2}$ is H. In some embodiments of formula I, $R^{y2}$ is halogen. In some such embodiments of formula I, $R^{y2}$ is fluoro or bromo. In some embodiments of formula I, $R^{y2}$ is —OR'. In some such embodiments of formula I, R' is H. Accordingly, in some embodiments of formula I, $R^{y2}$ is —OH. In some embodiments of formula I, $R^{y2}$ is —OR', wherein R' is —C$_{1-6}$ alkyl. In some embodiments of formula I, $R^{y2}$ is —OCH$_3$.

In some embodiments of formula I, $R^{y3}$ is —R'. In some such embodiments of formula I, —R' is H. Accordingly, in some embodiments of formula I, $R^{y3}$ is H. In some embodiments of formula I, $R^{y3}$ is —R', wherein R' is —C$_{1-6}$ alkyl. In some such embodiments of formula I, —R' is CH$_3$. Accordingly, in some embodiments of formula I, $R^{y3}$ is CH$_3$. In some embodiments of formula I, $R^{y3}$ is halogen. In some such embodiments of formula I, $R^{y3}$ is chloro or bromo. In some embodiments of formula I, $R^{y3}$ is —OR'. In some such embodiments of formula I, R' is H. Accordingly, in some embodiments of formula I, $R^{y3}$ is —OH. In some embodiments of formula I, $R^{y3}$ is —OR', wherein R' is —C$_{1-6}$ alkyl. In some embodiments of formula I, $R^{y3}$ is —OCH$_3$.

In some embodiments of formula I, $R^{y3}$ is —N(R')$_2$. In some such embodiments of formula I, each R' is H. Accordingly, in some embodiments of formula I, $R^{y3}$ is —NH$_2$. In some embodiments of formula I, $R^{y3}$ is —N(R')$_2$, wherein each R' is independently selected from H and —C$_{1-6}$ alkyl. In some such embodiments of formula I, $R^{y3}$ is —N(R')$_2$, wherein each R' is independently selected from H and —CH$_3$. In some embodiments of formula I, $R^{y3}$ is —NHCH$_3$. In some embodiments of formula I, $R^{y3}$ is —N(R')C(O)N(R')$_2$. In some such embodiments of formula I, each R' is independently selected from H and —C$_{1-6}$ alkyl. In some embodiments of formula I, $R^{y3}$ is —N(R')C(O)N(R')$_2$, wherein each R is independently selected from H and —CH$_3$. In some embodiments of formula I, $R^{y3}$ is —NHC(O)NHCH$_3$.

As defined generally above for formula I, $Z^1$ is selected from N and C—$R^{z1}$ when $\overset{a}{=\!=\!=}$ is a double bond or $Z^1$ is CH($R^{z1}$) or C($R^{z2}$)$_2$ when $\overset{a}{=\!=\!=}$ is a single bond. In some embodiments of formula I, $\overset{a}{=\!=\!=}$ is a double bond and $Z^1$ is N. In some embodiments of formula $\overset{a}{=\!=\!=}$I, $\overset{a}{=\!=\!=}$ is a double bond and $Z^1$ is C—$R^{z1}$. In some embodiments of formula I, $\overset{a}{=\!=\!=}$ is a single bond and $Z^1$ is CH($R^{z1}$). In some embodiments of formula I, $\overset{a}{=\!=\!=}$ is a single bond and $Z^1$ is C($R^{z1}$)$_2$.

As defined generally above for formula I, $R^{z1}$ is selected from halogen, —CN, —NO$_2$, —R', —(C$_{1-6}$ alkylene)OR', —(C$_{1-6}$ alkylene)N(R')$_2$, —OR', —SR', —SF$_5$, —N(R')$_2$, —C(O)R', —C(O)OR', —OC(O)R', —C(O)N(R')$_2$, —N(R')C(O)R', —SOR', —SO$_2$R', —N(R$^j$)SO$_2$R', and —SO$_2$N(R')$_2$. In some embodiments of formula I, $R^{z1}$ is —R'. In some such embodiments of formula I, R' is H. Accordingly, in some embodiments of formula I, $R^{z1}$ is H.

In some embodiments of formula I, $R^{z1}$ is halogen. In some such embodiments of formula I, $R^{z1}$ is bromo. In some embodiments of formula I, $R^{z1}$ is iodo. In some embodiments of formula I, $R^{z1}$ is chloro.

In some embodiments of formula I, $R^{z1}$ is —NO$_2$.

In some embodiments of formula I, $R^{z1}$ is —CF$_3$.

In some embodiments of formula I, $R^{z1}$ is —C(O)R'. In some such embodiments of formula I, R' is —C$_{1-6}$ alkyl. In some embodiments of formula I, $R^{z1}$ is —C(O)CH$_3$.

In some embodiments of formula I, $R^{z1}$ is —C(O)OR'. In some such embodiments of formula I, R' is selected from H and —C$_{1-6}$ alkyl. In some embodiments of formula I, $R^{z1}$ is —C(O)OH. In some embodiments of formula I, $R^{z1}$ is —C(O)OCH$_3$.

In some embodiments of formula I, $R^{z1}$ is —N(R')$_2$. In some such embodiments of formula I, each R' is H. Accordingly, in some embodiments of formula I, $R^{z1}$ is —NH$_2$.

In some embodiments of formula I, $R^{z1}$ is —R', wherein R' is —C$_{1-6}$ alkyl. In some embodiments of formula I, $R^{z1}$ is isopropyl. In some embodiments of formula I, $R^{z1}$ is cyclopropyl. In some embodiments of formula I, $R^{z1}$ is —R', wherein R' is —C$_{1-6}$ alkynyl. In some embodiments of formula I, $R^{z1}$ is —C≡CH.

In some embodiments of formula I, $R^{z1}$ is —OR'. In some such embodiments of formula I, R' is H. Accordingly, in some embodiments of formula I, $R^{z1}$ is —OH. In some embodiments of formula I, $R^{z1}$ is —OR, wherein R' is —$C_{1-6}$ alkyl. In some embodiments of formula I, $R^{z1}$ is —$OCH_3$. In some embodiments of formula I, $R^{z1}$ is —OCH$(CH_3)_2$.

In some embodiments of formula I, $R^{z1}$ is —SR', wherein R' is —$C_{1-6}$ alkyl. In some embodiments of formula I, $R^{z1}$ is —$SCH_3$.

In some embodiments of formula I, $R^{z1}$ is —($C_{1-6}$ alkylene)OR'. In some embodiments of formula I, $R^{z1}$ is —$CH_2$OR'. In some such embodiments of formula I, R' is H. Accordingly, in some embodiments of formula I, $R^{z1}$ is —$CH_2$OH. In some embodiments of formula I, $R^{z1}$ is —$C(CH_3)_2$OH.

In some embodiments of formula I, $R^{z1}$ is —($C_{1-6}$ alkylene)N(R')$_2$. In some embodiments of formula I, $R^{z1}$ is —$CH_2$N(R')$_2$. In some such embodiments of formula I, each R' is H. Accordingly, in some embodiments of formula I, $R^{z1}$ is —$CH_2NH_2$.

As defined generally above for formula I, $Z^2$ is selected from N and C—$R^{z2}$. In some embodiments of formula I, $Z^2$ is N. In some embodiments of formula I, $Z^2$ is C—$R^{z2}$.

As defined generally above for formula I, $R^{z2}$ is selected from halogen, —CN, —R', —OR', and —N(R')$_2$. In some embodiments of formula I, $R^{z2}$ is —R'. In some such embodiments of formula I, R' is H. Accordingly, in some embodiments, $R^{z2}$ is H. In some embodiments of formula I, $R^{z2}$ is —R', wherein R' is —$C_{1-6}$ alkyl. In some embodiments of formula I, $R^{z2}$ is —$CH_3$. In some embodiments of formula I, $R^{z2}$ is —$CH(CH_3)_2$. In some embodiments of formula I, $R^{z2}$ is cyclopropyl.

In some embodiments of formula I, $R^{z2}$ is halogen. In some embodiments of formula I, $R^{z2}$ is bromo. In some embodiments of formula I, $R^{z2}$ is iodo.

In some embodiments of formula I, $R^{z2}$ is —OR'. In some such embodiments of formula I, R' is H. Accordingly, in some embodiments of formula I, $R^{z2}$ is —OH. In some embodiments of formula I, $R^{z2}$ is —OR', wherein R' is —$C_{1-6}$ alkyl. Accordingly, in some embodiments of formula I, $R^z$ is —$OCH_3$.

In some embodiments, $R^{z2}$ is —N(R')$_2$. In some such embodiments, each R' is H. Accordingly, in some embodiments, $R^{z2}$ is —$NH_2$.

As defined generally above for formula I, each R' is independently selected from hydrogen, $C_{1-6}$ alkyl, $C_{2-6}$ alkenyl, and $C_{2-6}$ alkynyl, wherein each of $C_{1-6}$ alkyl, $C_{2-6}$ alkenyl, or $C_{2-6}$ alkynyl is optionally substituted with halogen; or two instances of R', together with the nitrogen atom to which they are attached, form a 3- to 6-membered saturated or partially unsaturated heterocyclic ring.

In some embodiments of formula I, $Z^1$ is C—$R^{z1}$ and $Z^2$ is C—$R^{z2}$. Accordingly, the present disclosure provides a compound of formula I-a:

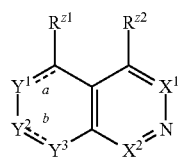

I-a or a pharmaceutically acceptable salt thereof.

In some embodiments of formula I, $Z^1$ is C—$R^{z1}$, $Z^2$ is C—$R^{z2}$, and each of $\stackrel{a}{=\!=\!=}$ and $\stackrel{b}{=\!=\!=}$ is a double bond. Accordingly, in some embodiments of formula I, the SARM1 inhibitor is a compound of formula I-b:

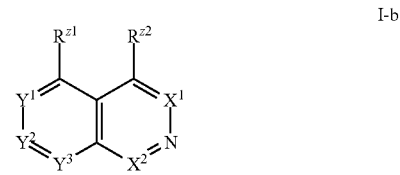

I-b or a pharmaceutically acceptable salt thereof.

In some embodiments of formula I, $\stackrel{a}{=\!=\!=}$ a double bond, $\stackrel{b}{=\!=\!=}$ is a single bond, $Y^2$ is N—R', and $Y^3$ is C(O). Accordingly, in some embodiments of formula I, the SARM1 inhibitor is a compound of formula I-c:

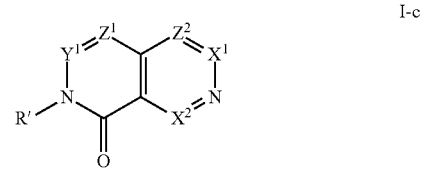

I-c or a pharmaceutically acceptable salt thereof.

In some embodiments of formula I of formula I $\stackrel{a}{=\!=\!=}$ is a single bond, $Y^2$ is N—R', and $Y^3$ is C(O). Accordingly, in some embodiments of formula I, the present disclosure provides a compound of formula I-d:

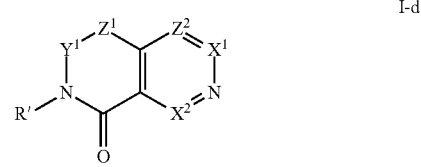

I-d or a pharmaceutically acceptable salt thereof.

In some embodiments of formula I, $\stackrel{a}{=\!=\!=}$ is a double bond, $Y^2$ is C(O), and $Y^3$ is N—R'. Accordingly, in some embodiments of formula I, the present disclosure provides a compound of formula I-e:

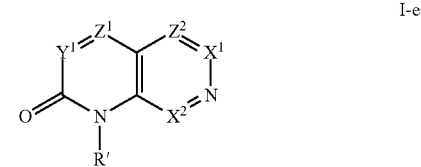

I-e or a pharmaceutically acceptable salt thereof.

In some embodiments of formula I, $\stackrel{a}{=\!=\!=}$ is a single bond, $Y^2$ is C(O), and $Y^3$ is N—R'. Accordingly, in some embodiments of formula I, the present disclosure provides a compound of formula I-f:

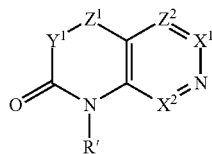

I-f or a pharmaceutically acceptable salt thereof.

In some embodiments of formula I, $X^2$ is $C-R^{x2}$, $Y^1$ is $C-R^{y1}$, $Y^2$ is $C-R^{y2}$, and $Y^3$ is $C-R^{y3}$. Accordingly, in some embodiments of formula I, the present disclosure provides a compound of formula I-g:

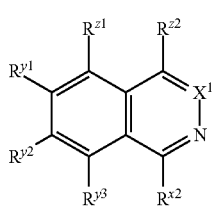

I-g or a pharmaceutically acceptable salt thereof.

In some embodiments of formula I, $R^{x2}$ is H. Accordingly, in some embodiments of formula I, the present disclosure provides a compound of formula I-h:

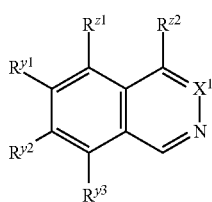

I-h or a pharmaceutically acceptable salt thereof.

In some embodiments of formula I, $R^{y1}$ is H. Accordingly, in some embodiments of formula I, the present disclosure provides a compound of formula I-i:

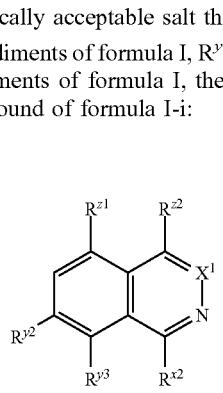

I-i or a pharmaceutically acceptable salt thereof.

In some embodiments of formula I, $R^{y2}$ is H. Accordingly, in some embodiments of formula I, the present disclosure provides a compound of formula I-j:

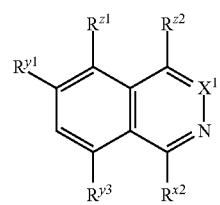

I-j or a pharmaceutically acceptable salt thereof.

In some embodiments of formula I, $R^{x1}$ is H. Accordingly, in some embodiments of formula I, the present disclosure provides a compound of formula I-k:

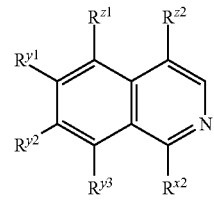

I-k or a pharmaceutically acceptable salt thereof.

In some embodiments of formula I, the present disclosure provides a compound of any one of formula I-b-i, I-b-ii, I-b-iii, I-b-iv, I-b-v, I-b-vi, I-b-vii, I-b-viii, I-b-ix, I-b-x, I-b-xi, I-b-xii, I-b-xiii, I-b-xiv, I-b-xv, I-b-xvi, and I-b-xvii:

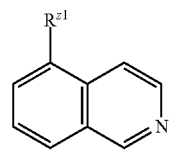

I-b-i

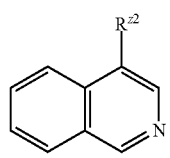

I-b-ii

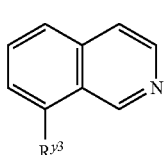

I-b-iii

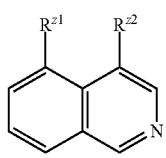

I-b-iv

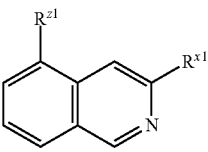

I-b-v

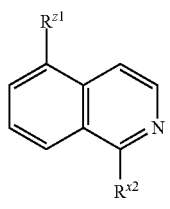
I-b-vi

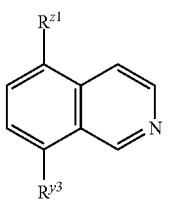
I-b-vii

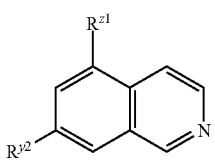
I-b-viii

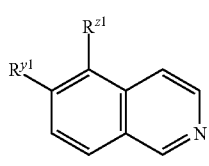
I-b-ix

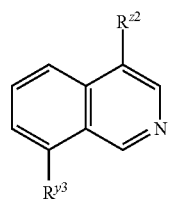
I-b-x

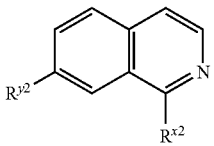
I-b-xi

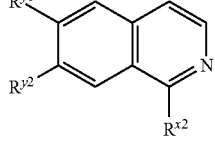
I-b-xii

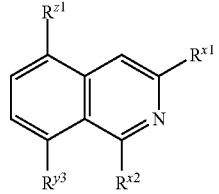
I-b-xiii

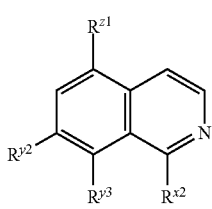
I-b-xiv

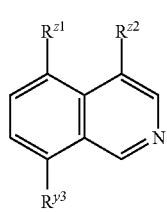
I-b-xv

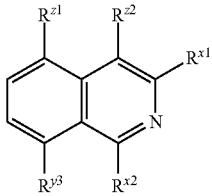
I-b-xvi

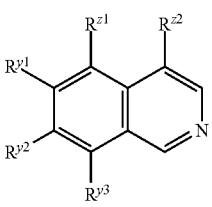
I-b-xvii or a pharmaceutically acceptable salt thereof, wherein each of $R^{x1}$, $R^{x2}$, $R^{y1}$, $R^{y2}$, $R^{y3}$, $R^{z1}$ and $R^{z2}$ is as defined above for formula I and described herein.

In some embodiments of formula I, the present disclosure provides a compound of any one of formula I-b-xviii, I-b-xix, I-b-xx, I-b-xxi, I-b-xxii, I-b-xxiii, I-b-xxiv, I-b-xxv, and I-b-xxvi:

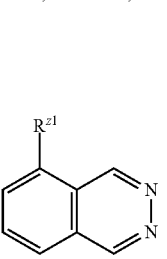
I-b-xviii

I-b-xix

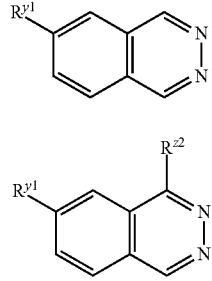
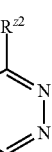
I-b-xx

I-b-xxi
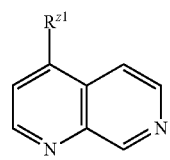

I-b-xxii
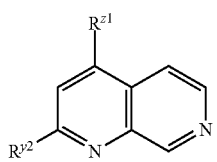

I-b-xxiii
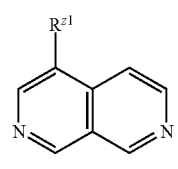

I-b-xxiv
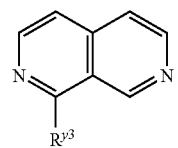

I-b-xxv
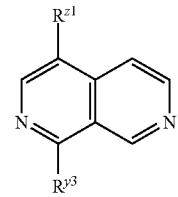

I-b-xxvi
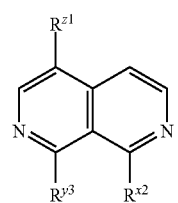

or a pharmaceutically acceptable salt thereof, wherein each of $R^{x1}$, $R^{x2}$, $R^{y1}$, $R^{y2}$, $R^{y3}$, $R^{z1}$ and $R^{z2}$ is as defined above for formula I and described herein.

In some embodiments of formula I, the present disclosure provides a compound of any one of formula I-a-i, I-a-ii, and I-a-iii, or a pharmaceutically acceptable salt thereof:

I-a-i
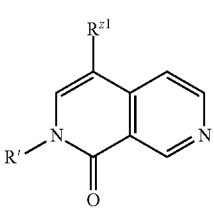

I-a-ii
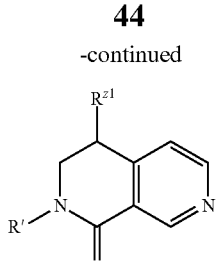

I-a-iii
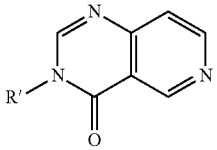

wherein each of $R^{z1}$ and R' is as defined above and described herein.

In some embodiments, a compound of formula I is selected from:

| Example | Structure |
| --- | --- |
| I-1 | 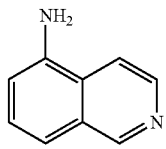 [SMILES: Nc1cccc2cnccc12] |
| I-2 | 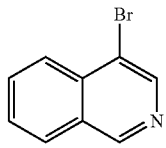 [SMILES: Brc1cncc2ccccc12] |
| I-3 | 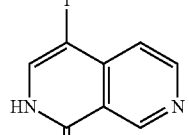 |
| I-4 | 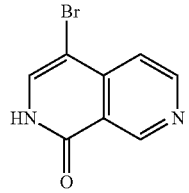 [SMILES: O=c1[nH]cc(Br)c2ccncc12] |
| I-5 | 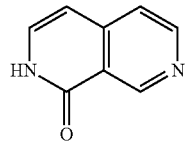 |
| I-6 | 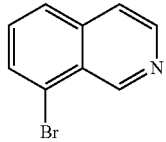 [SMILES: Brc1cccc2ccncc12] |

-continued

| Example | Structure |
|---------|-----------|
| I-7 | 7-fluorophthalazin-1(2H)-one |
| I-8 | 5-bromoisoquinoline |
| I-9 | 5-chloro-6-aminoisoquinoline |
| I-10 | 5-bromophthalazine |
| I-11 | 8-hydroxyisoquinoline |
| I-12 | 5-bromo-8-aminoisoquinoline |
| I-13 | 5-bromo-4-methylphthalazine |
| I-14 | 5-bromo-3-hydroxyisoquinoline |
| I-15 | 5-bromo-8-methoxyisoquinoline |

-continued

| Example | Structure |
|---------|-----------|
| I-16 | 6-bromophthalazine |
| I-17 | 4-methylisoquinoline |
| I-18 | 5-iodo-1-aminoisoquinoline |
| I-19 | 5-cyclopropylisoquinoline |
| I-20 | 4-bromo-2-ethyl-2,7-naphthyridin-1(2H)-one |
| I-21 | 4-bromo-8-methoxy-2,7-naphthyridine |
| I-22 | 4-isopropyl-2,7-naphthyridin-1(2H)-one |
| I-23 | 5-bromo-1-(dimethylamino)isoquinoline |

-continued

| Example | Structure |
|---|---|
| I-24 | (4-cyclopropyl-1-methoxy-2,7-naphthyridine) |
| I-25 | (5-isopropoxyisoquinoline) |
| I-26 | (5-iodoisoquinoline) |
| I-27 | (5-bromo-N-methylisoquinolin-1-amine) |
| I-28 | (4-methoxy-2,7-naphthyridin-1(2H)-one) |
| I-29 | (4-bromo-1,7-naphthyridin-2(1H)-one) |
| I-30 | (5-chloro-7-fluoroisoquinoline) |
| I-31 | (3,4-dihydroisoquinolin-1(2H)-one) |

-continued

| Example | Structure |
|---|---|
| I-32 | (5-chloroisoquinolin-8-amine) |
| I-33 | (5-bromoisoquinolin-1(2H)-one) |
| I-34 | (5-chloro-8-bromoisoquinoline) |
| I-35 | (4-bromoisoquinolin-5-amine) |
| I-36 | (2,7-naphthyridine) |
| I-37 | (phthalazin-5-amine) |
| I-38 | (2,7-naphthyridin-1-amine) |
| I-39 | (7-hydroxyisoquinolin-1(2H)-one) |
| I-40 | (7-fluoro-6-methoxyisoquinolin-1(2H)-one) |

| Example | Structure |
|---|---|
| I-41 | 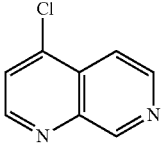 [SMILES: Clc1ccnc2cnccc12] |
| I-42 | 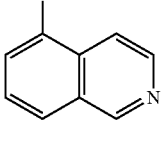 |
| I-43 | 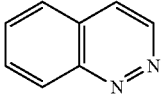 |
| I-44 | 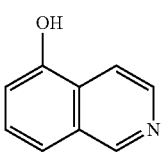 |
| I-45 | 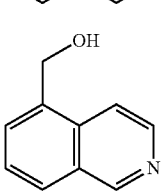 |
| I-46 | 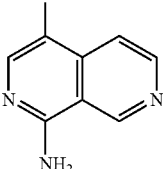 |
| I-47 | 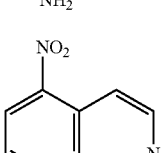 |
| I-48 | 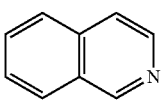 |
| I-49 | 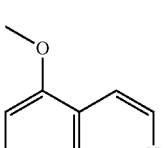 |
| I-50 | 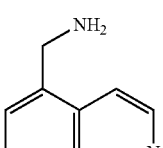 |
| I-51 | 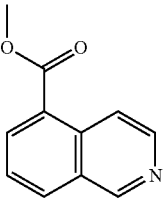 |
| I-52 | 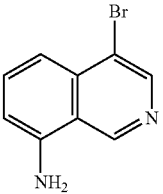 [SMILES: Nc1cccc2c(Br)cncc12] |
| I-53 |  |
| I-54 | 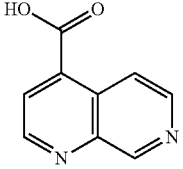 |
| I-55 | 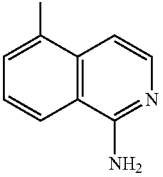 |
| I-56 | 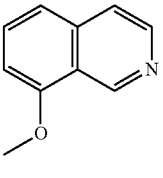 |
| I-57 | 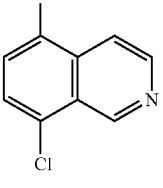 |
| I-58 | 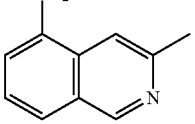 |

-continued
| Example | Structure |
|---|---|
| I-59 | 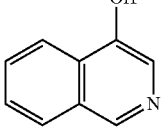 |
| I-60 | 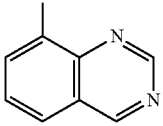 |
| I-61 | 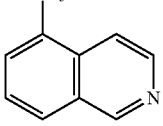 |
| I-62 | 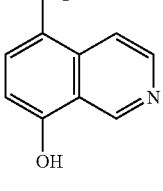 |
| I-63 | 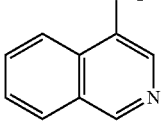 |
| I-64 | 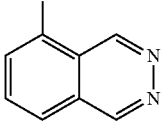 |
| I-65 | 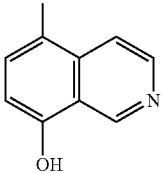 |
| I-66 | 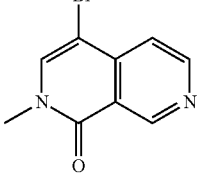 |
| I-67 | 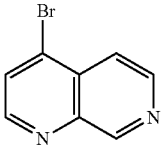 |
-continued
| Example | Structure |
|---|---|
| I-68 | 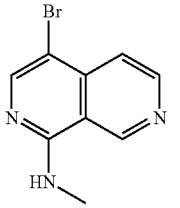 |
| I-69 | 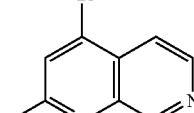 |
| I-70 | 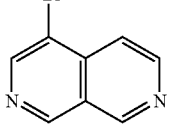 |
| I-71 | 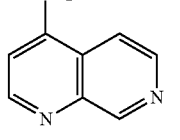 |
| I-72 | 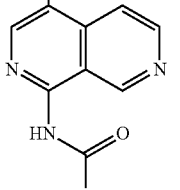 |
| I-73 | 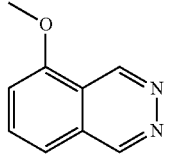 |
| I-74 | 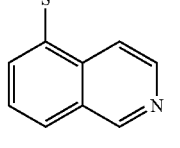 |
| I-75 | 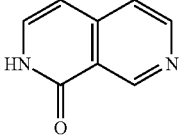 |

| Example | Structure |
|---|---|
| I-76 | 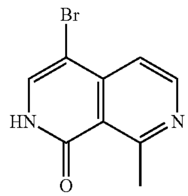 |
| I-77 | 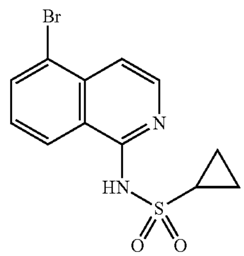 [SMILES: O=S(=O)(Nc1nccc2c(Br)cccc12)C1CC1] |
| I-78 | 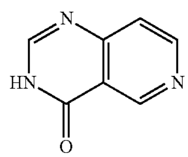 [SMILES: O=c1[nH]cnc2ccncc12] |
| I-79 | 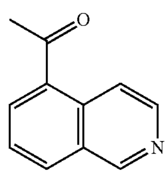 |
| I-80 | 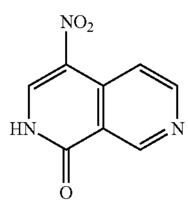 [SMILES: O=c1[nH]cc([N+](=O)[O-])c2ccncc12] |
| I-81 | 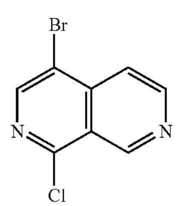 [SMILES: Clc1ncc(Br)c2ccncc12] |
| I-82 | 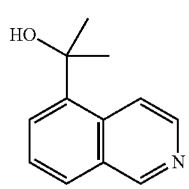 |
| I-83 | 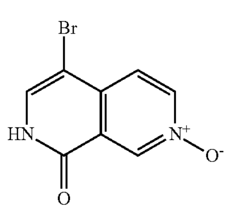 [SMILES: O=c1[nH]cc(Br)c2cc[n+]([O-])cc12] |

| Example | Structure |
|---|---|
| I-84 | 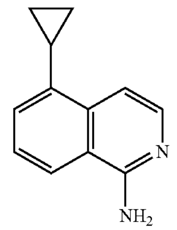 [SMILES: Nc1nccc2c(C3CC3)cccc12] |
| I-85 | 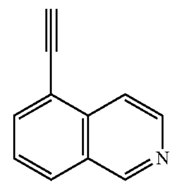 |
| I-86 | | or a pharmaceutically acceptable salt thereof.

In some embodiments, the SARM1 inhibitor is a compound of formula II:

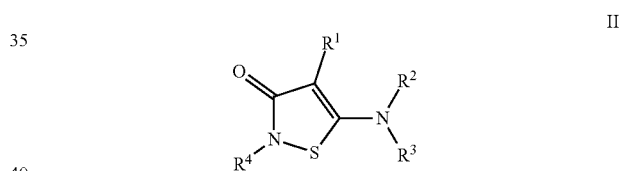

II or a pharmaceutically acceptable salt thereof, wherein
$R^1$ is selected from —CN, —NO$_2$, —C(O)R″, —S(O)$_2$R″, —CON(R″)$_2$, —S(O)$_2$N(R″)$_2$, and —CO$_2$R″;
$R^2$ is —R″;
$R^3$ is —(CH$_2$)$_{0-2}$Cy, or:
$R^2$ and $R^3$, together with the nitrogen atom to which they are attached, form a 4- to 7-membered saturated or partially unsaturated ring fused to Cy or a 4- to 7-membered saturated or partially unsaturated ring substituted with —Cy;
Cy is selected from phenyl, a 5- to 6-membered heteroaryl ring having 1-3 heteroatoms independently selected from nitrogen, oxygen, and sulfur, an 8- to 10-membered bicyclic heteroaryl ring having 1-3 heteroatoms independently selected from nitrogen, oxygen, and sulfur, and an 8- to 10-membered bicyclic aryl ring, wherein each phenyl, heteroaryl and aryl ring is substituted with 0-4 $R^x$;
each $R^x$ is independently selected from halogen, —CN, —NO$_2$, —OR″, —SR″, —N(R″)$_2$, —SO$_2$R″, —SO$_2$N(R″)$_2$, —CO$_2$R″, —CON(R″)$_2$, —N(R″)SO$_2$R″, —N(R″)C(O)R″, and optionally substituted C$_{1-6}$ aliphatic;
$R^4$ is —R″;
each R″ is independently hydrogen or optionally substituted C$_{1-6}$ aliphatic, or:

two instances of R″, together with the atom to which they are attached, form a 3- to 6-membered saturated or partially unsaturated heterocyclic ring.

As defined generally above for formula II, $R^1$ is selected from —CN, —NO$_2$, —C(O)R″, —S(O)$_2$R″, —CON(R″)$_2$, —S(O)$_2$N(R″)$_2$, and —CO$_2$R″. In some embodiments of formula II, $R^1$ is selected from —CN, —C(O)N(R″)$_2$ and —CO$_2$R″. In some embodiments of formula II, $R^1$ is —CN. In some embodiments, $R^1$ is —CON(R″)$_2$. In some such embodiments of formula II, each R″ is independently selected from hydrogen and $C_{1-6}$ aliphatic. In some embodiments of formula II, $R^1$ is —CON(R″)$_2$, wherein each R is independently selected from hydrogen and $C_{1-6}$ alkyl. In some embodiments of formula II, $R^1$ is —CON(R″)$_2$, wherein each R″ is independently selected from hydrogen and —CH$_3$. In some embodiments of formula II, $R^1$ is —CONH$_2$. In some embodiments of formula II, $R^1$ is —CO$_2$R″. In some such embodiments of formula II, R″ is selected from hydrogen and $C_{1-6}$ aliphatic. In some embodiments of formula II, $R^1$ is —CO$_2$R″, wherein R″ is selected from hydrogen and $C_{1-6}$ alkyl. In some embodiments of formula II, $R^1$ is —CO$_2$R″, wherein R″ is selected from hydrogen and —CH$_3$. In some embodiments of formula II, $R^1$ is —CO$_2$H. In some embodiments, $R^1$ is —NO$_2$. In some embodiments of formula II, $R^1$ is —C(O)R″. In some embodiments of formula II, $R^1$ is —S(O)$_2$R″. In some embodiments of formula II, $R^1$ is —S(O)$_2$N(R″)$_2$.

As defined generally above for formula II, $R^2$ is —R″. In some such embodiments of formula II, —R″ is hydrogen. Accordingly, in some embodiments of formula II, $R^2$ is —H. In some embodiments of formula II, $R^2$ is —R″, wherein —R″ is optionally substituted $C_{1-6}$ aliphatic. In some embodiments of formula II, $R^2$ is —R″, wherein —R″ is $C_{1-6}$ aliphatic. In some embodiments of formula II, $R^2$ is —$C_{1-6}$ alkyl. In some such embodiments of formula II, $R^2$ is —CH$_3$.

As defined generally above for formula II, $R^3$ is —(CH$_2$)$_{0-2}$Cy. In some embodiments of formula II, $R^3$ is —Cy. In some embodiments of formula II, $R^3$ is —CH$_2$-Cy. In some embodiments of formula II, $R^3$ is —(CH$_2$)$_2$—Cy.

As defined generally above for formula II, Cy is selected from phenyl, a 5- to 6-membered heteroaryl ring having 1-3 heteroatoms independently selected from nitrogen, oxygen, and sulfur, an 8- to 10-membered bicyclic heteroaryl ring having 1-3 heteroatoms independently selected from nitrogen, oxygen, and sulfur, and an 8- to 10-membered bicyclic aryl ring, wherein each phenyl, heteroaryl and aryl ring is substituted with 0-4 $R^x$.

In some embodiments of formula II, Cy is phenyl. In some embodiments of formula II, Cy is phenyl substituted with 1 $R^x$. In some embodiments of formula II, Cy is phenyl substituted with 2 $R^x$. In some embodiments of formula II, Cy is selected from

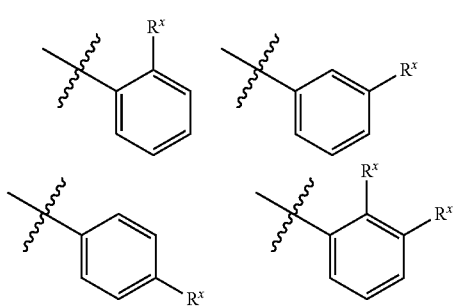

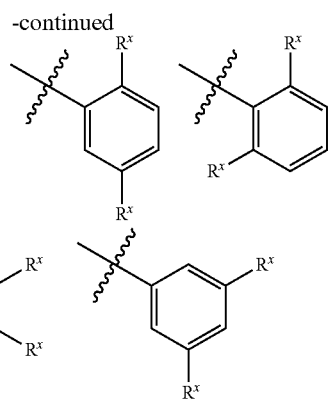

In some embodiments of formula II, Cy is a 5- to 6-membered heteroaryl ring having 1-3 heteroatoms independently selected from nitrogen, oxygen, and sulfur. In some embodiments of formula II, Cy is a 5-membered heteroaryl ring having 1-3 heteroatoms independently selected from nitrogen, oxygen, and sulfur. In some embodiments of formula II, Cy is a 6-membered heteroaryl ring having 1-3 nitrogen atoms. In some embodiments of formula II, Cy is a 6-membered heteroaryl ring having 1-2 nitrogen atoms. In some such embodiments of formula II, Cy is substituted with 1 Rx. In some embodiments of formula II, Cy is pyridinyl. In some such embodiments of formula II, Cy is pyrimidin-2-yl, pyrimidin-3-yl, or pyrimidin-4-yl. In some embodiments of formula II, Cy is pyridazinyl. In some embodiments of formula II, Cy is pyrazinyl. In some embodiments of formula II, Cy is pyrimidinyl. In some embodiments of formula II, Cy is selected from:

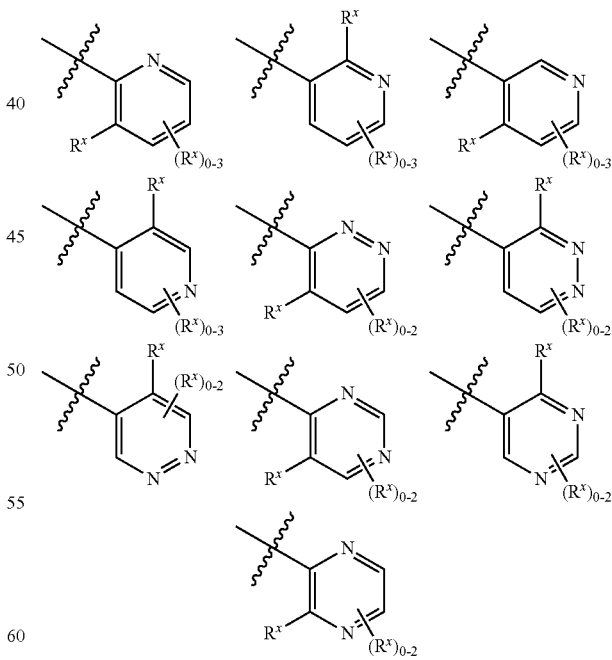

In some embodiments of formula II, Cy is an 8- to 10-membered bicyclic heteroaryl ring having 1-3 heteroatoms independently selected from nitrogen, oxygen, and sulfur. In some embodiments of formula II, Cy is an 8- to 10-membered bicyclic heteroaryl ring having 1-3 nitrogen atoms. In some embodiments of formula II, Cy is an 10-membered bicyclic heteroaryl ring having 1-3 nitrogen atoms. In some embodiments of formula II, Cy is an 10-membered bicyclic heteroaryl ring having 1 nitrogen atom. In some such embodiments of formula II, Cy is substituted with 1 $R^x$. In some embodiments of formula II, Cy is quinolin-2-yl, quinolin-3-yl, quinolin-4-yl, quinolin-5-yl, quinolin-6-yl, quinolin-7-yl, or quinolin-8-yl.

In some embodiments of formula II, Cy is an 8- to 10-membered bicyclic aryl ring. In some embodiments of formula II, Cy is a 10-membered bicyclic aryl ring. In some such embodiments of formula II, Cy is substituted with 1 Rx. In some embodiments, Cy is naphth-1-yl. In some embodiments of formula II, Cy is naphth-2-yl.

In some embodiments of formula II, $R^2$ and $R^3$, together with the nitrogen atom to which they are attached, form a 4- to 7-membered saturated or partially unsaturated ring fused to Cy or a 4- to 7-membered saturated or partially unsaturated ring substituted with —Cy. In some embodiments of formula II, $R^2$ and $R^3$, together with the nitrogen atom to which they are attached, form a ring selected from:

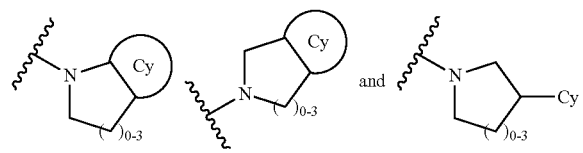

wherein Cy is substituted with 0-4 $R^x$.

As defined generally above for formula II, each $R^x$ is independently selected from halogen, —CN, —$NO_2$, —OR", —SR", —N(R")$_2$, —$SO_2$R", —$SO_2$N(R")$_2$, —$CO_2$R", —CON(R")$_2$, —N(R)$SO_2$R", and —N(R")C(O)R", or optionally substituted $C_{1-6}$ aliphatic.

In some embodiments of formula II, $R^x$ is halogen. In some such embodiments of formula II, $R^x$ is fluoro. In some embodiments of formula II, $R^x$ is chloro.

In some embodiments of formula II, $R^x$ is optionally substituted $C_{1-6}$ aliphatic. In some embodiments of formula II, $R^x$ is optionally substituted —$C_{1-6}$ alkyl. In some embodiments of formula II, $R^x$ is —$C_{1-6}$ alkyl optionally substituted with halogen. In some embodiments of formula II, $R^x$ is optionally substituted —$CH_3$. In some such embodiments of formula II, $R^x$ is —$CF_3$.

In some embodiments of formula II, $R^x$ is $C_{1-6}$ aliphatic. In some embodiments of formula II, $R^x$ is —$C_{1-6}$ alkyl. In some embodiments of formula II, $R^x$ is —$CH_3$. In some embodiments of formula II, $R^x$ is —$CH(CH_3)_2$.

In some embodiments of formula II, $R^x$ is —OR". In some such embodiments of formula II, R" is $C_{1-6}$ aliphatic. In some embodiments of formula II, $R^x$ is —OR", wherein R" is $C_{1-6}$ alkyl. In some embodiments of formula II, RX is —$OCH_3$.

In some embodiments of formula II, $R^x$ is —OR". In some such embodiments of formula II, R" is optionally substituted $C_{1-6}$ aliphatic. In some embodiments of formula II, $R^x$ is —OR", wherein R" is optionally substituted $C_{1-6}$ alkyl. In some embodiments of formula II, $R^x$ is —OR", wherein R" is optionally substituted —$CH_3$. In some embodiments of formula II, $R^x$ is —OR", wherein R" is —$CF_3$. Accordingly, in some embodiments of formula II, $R^x$ is —$OCF_3$.

In some embodiments of formula II, $R^x$ is —$SO_2$R". In some such embodiments of formula II, R" is optionally substituted $C_{1-6}$ aliphatic. In some embodiments of formula II, $R^x$ is —$SO_2$R", wherein R" is $C_{1-6}$ alkyl. In some embodiments of formula II, $R^x$ is —$SO_2$R", wherein R" is —$CH_3$. Accordingly, in some embodiments of formula II, $R^x$ is —$SO_2CH_3$.

In some embodiments of formula II, $R^x$ is —SR". In some such embodiments of formula II, R" is optionally substituted $C_{1-6}$ aliphatic. In some embodiments of formula II, $R^x$ is —SR", wherein R" is $C_{1-6}$ alkyl. In some embodiments of formula II, $R^x$ is —SR", wherein R" is —$CH_3$. Accordingly, in some embodiments of formula II, $R^x$ is —$SCH_3$.

As defined generally above for formula II, $R^4$ is —R". In some embodiments of formula II, $R^4$ is —R". In some such embodiments of formula II, —R" is hydrogen. Accordingly, in some embodiments of formula II, $R^4$ is hydrogen. In some embodiments of formula II, $R^4$ is —R", wherein R" is optionally substituted $C_{1-6}$ aliphatic. In some embodiments of formula II, $R^4$ is —R", wherein R" is $C_{1-6}$ aliphatic. In some embodiments of formula II, $R^4$ is —R", wherein R" is $C_{1-6}$ alkyl. In some embodiments, $R^4$ is —R", wherein R" is $CH_3$. Accordingly, in some embodiments of formula II, $R^4$ is —$CH_3$.

As defined generally above for formula II, each R" is independently hydrogen or optionally substituted $C_{1-6}$ aliphatic; or two instances of R", together with the atom to which they are attached, form a 3- to 6-membered saturated or partially unsaturated heterocyclic ring.

In some embodiments of formula II, R" is hydrogen. In some embodiments of formula II, R" is optionally substituted $C_{1-6}$ aliphatic. In some such embodiments of formula II, R" is —$C_{1-6}$ alkyl. In some embodiments, R" is —$CH_3$.

It will be appreciated that compounds of formula II having the structure

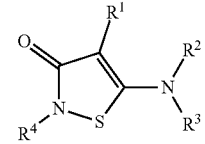

can exist in two tautomeric forms when $R^4$ is H:

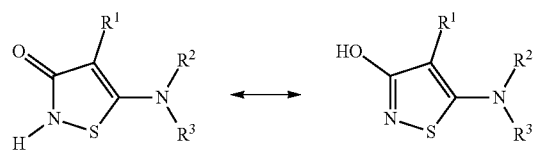

Accordingly, it will be appreciated that compounds of formula II wherein $R^4$ is H can be drawn in either tautomeric form.

In some embodiments of formula II, $R^1$ is —CN. Accordingly, in some embodiments of formula II, the SARM1 inhibitor is a compound of formula II-a:

II-a

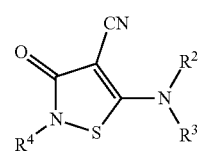

or a pharmaceutically acceptable salt thereof, wherein each of $R^2$, $R^3$ and $R^4$ is as defined above and described herein.

In some embodiments of formula II, $R^1$ is —CON(R")$_2$. Accordingly, in some embodiments of formula II, the SARM1 inhibitor is a compound of formula II-b:

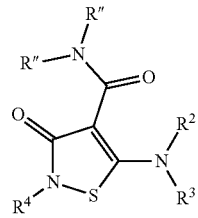

II-b or a pharmaceutically acceptable salt thereof, wherein each of $R^2$, $R^3$, $R^4$ and R" is as defined above and described herein.

In some embodiments of formula II-a or II-b, $R^2$ is H. Accordingly, in some embodiments, the SARM1 inhibitor is a compound of formula II-a-i or II-a-ii:

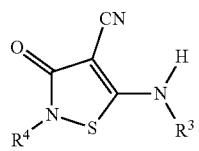

II-a-i

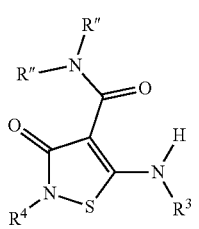

II-a-ii or a pharmaceutically acceptable salt thereof, wherein each of $R^3$, $R^4$ and R" is as defined above and described herein.

In some embodiments of formula II-a or II-b, $R^3$ is —Cy, wherein —Cy is phenyl. Accordingly, in some embodiments, the SARM1 inhibitor is a compound of formula II-b-i or II-b-ii:

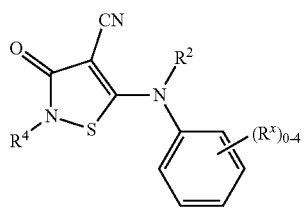

II-b-i

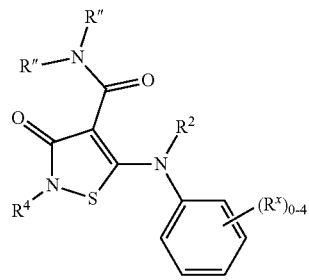

II-b-ii or a pharmaceutically acceptable salt thereof, wherein each of $R^2$, $R^4$, R" and $R^x$ is as defined above and described herein.

In some embodiments, the compound of formula II is selected from:

| Example | Structure |
|---|---|
| II-1 | 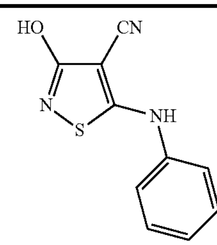 |
| II-2 | 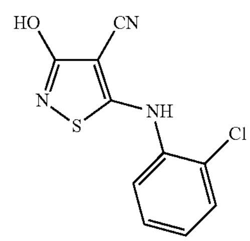 [SMILES: N#Cc1c(O)nsc1Nc1ccccc1Cl] |
| II-3 | 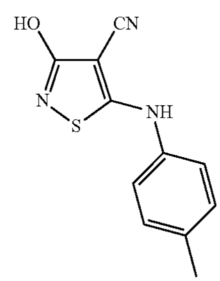 [SMILES: Cc1ccc(Nc2snc(O)c2C#N)cc1] |
| II-4 | 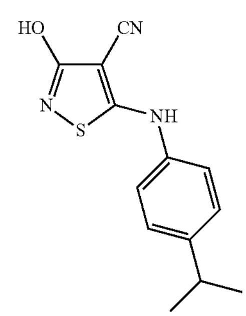 [SMILES: CC(C)c1ccc(Nc2snc(O)c2C#N)cc1] |

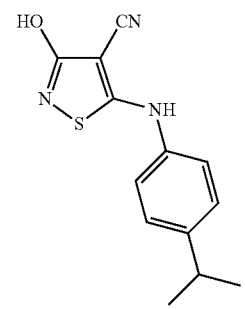

| Example | Structure |
|---|---|
| II-5 | 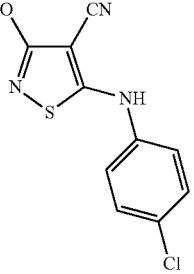 |
| II-6 | 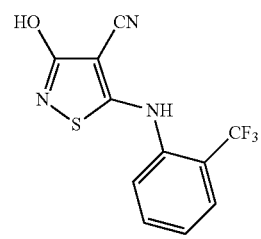 [SMILES: N#Cc1c(O)nsc1Nc1ccccc1C(F)(F)F] |
| II-7 | 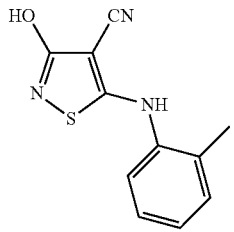 [SMILES: Cc1ccccc1Nc1snc(O)c1C#N] |
| II-8 | 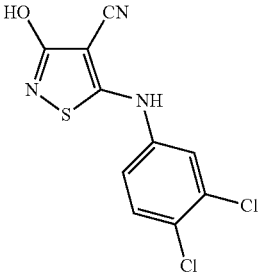 [SMILES: N#Cc1c(O)nsc1Nc1ccc(Cl)c(Cl)c1] |
| II-9 | 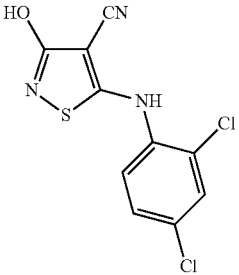 [SMILES: N#Cc1c(O)nsc1Nc1ccc(Cl)cc1Cl] |
| II-10 | 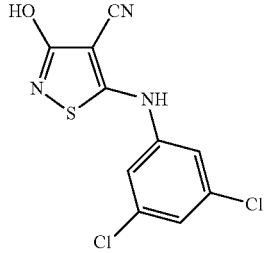 [SMILES: N#Cc1c(O)nsc1Nc1cc(Cl)cc(Cl)c1] |
| II-11 | 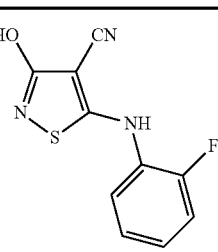 |
| II-12 | 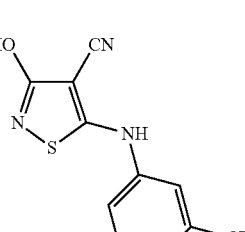 |
| II-13 | 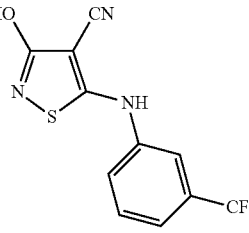 |
| II-14 | 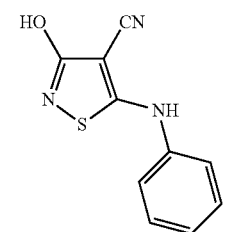 |
| II-15 | 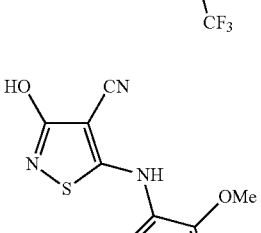 |
| II-16 | 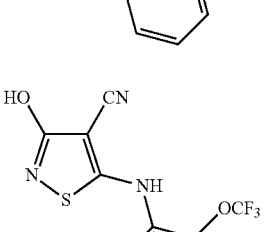 |

| Example | Structure |
|---|---|
| II-17 | 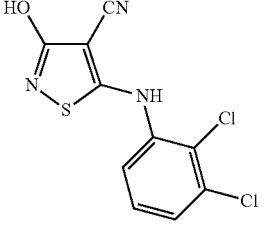 [SMILES: N#Cc1c(O)nsc1Nc1cccc(Cl)c1Cl] |
| II-18 | 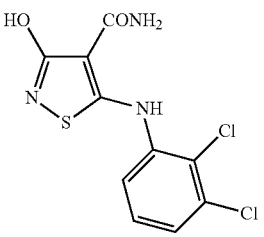 [SMILES: NC(=O)c1c(O)nsc1Nc1cccc(Cl)c1Cl] |
| II-19 | 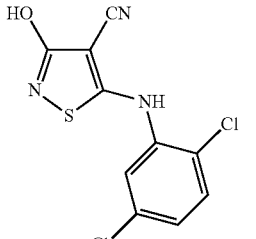 |
| II-20 | 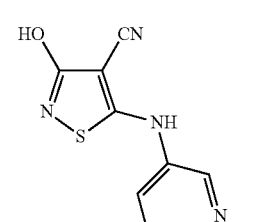 |
| II-21 | 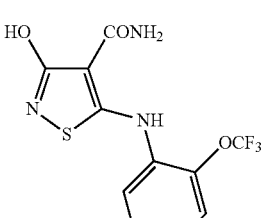 |
| II-22 | 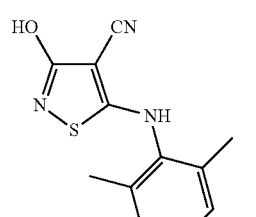 |
| II-23 | 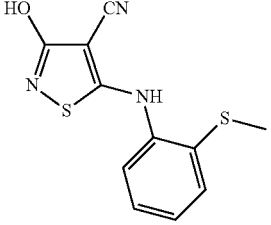 [SMILES: CSc1ccccc1Nc1snc(O)c1C#N] |
| II-24 | 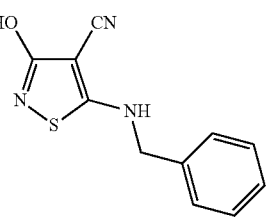 |
| II-25 | 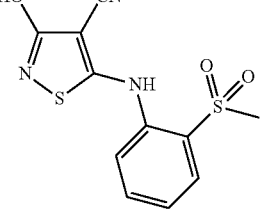 |
| II-26 | 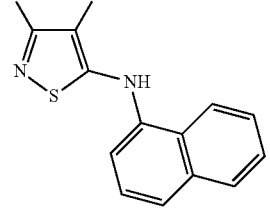 |
| II-27 | 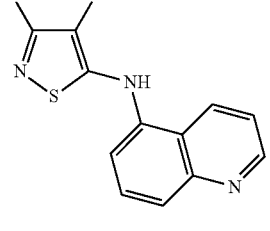 |
| II-28 | 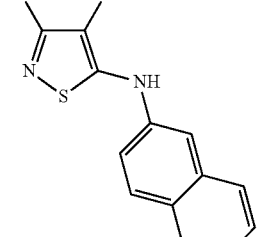 |

-continued

| Example | Structure |
|---|---|
| II-29 | HO, CN, isothiazole-quinoline NH structure |
| II-30 | HO, CN, isothiazole N-methyl-(2-CF3-phenyl) structure |
| II-31 | O, CN, N-methyl isothiazolone NH-(2-CF3-phenyl) structure |
| II-32 | O, CN, N-(2-methoxyethyl) isothiazolone NH-(2-CF3-phenyl) structure |

In some embodiments, one or more compounds of formula II covalently inhibit SARM1. In some embodiments, one or more compounds of formula II covalently modify a cysteine residue of SARM1. In some embodiments, one or more compounds of formula II covalently modify Cys635 of SARM1. In some embodiments, one or more compounds of formula II covalently modify Cys629 of SARM1. In some embodiments, one or more compounds of formula II covalently modify Cys649 of SARM1.

In some embodiments, the SARM1 inhibitor is a compound of formula III:

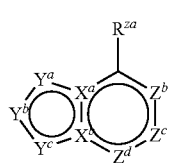

III or a pharmaceutically acceptable salt thereof, wherein:
one of $X^a$ and $X^b$ is selected from C and N and the other is C;

$Y^a$ is selected from N, N—$R^\dagger$ and C—$R^{ya}$;
$Y^b$ is selected from N and C—$R^{yb}$;
$Y^c$ is selected from N, N—$R^\dagger$, O, S, and S(O)$_2$;
$Z^b$ is selected from N and C—$R^{zb}$;
$Z^c$ is selected from N and C—$R^{zc}$;
$Z^d$ is selected from N and C—$R^{zd}$;
each $R^\dagger$ is independently selected from hydrogen and $C_{1-6}$ aliphatic optionally substituted with —OR''', —C(O)N(R''')$_2$, or —C(O)OR''';
each of $R^{ya}$, $R^{yb}$, $R^{za}$, $R^{zb}$, $R^{zc}$, and $R^{zd}$ is independently selected from hydrogen, halogen, —CN, —OR''', —C(O)OR''', and $C_{1-6}$ aliphatic optionally substituted with halogen, —CN, —OR''', —N(R''')$_2$, —C(O)OR''', or —C(O)N(R''')2; and
each R''' is independently selected from hydrogen and $C_{1-6}$ aliphatic;
or two instances of R''', together with the atom to which they are attached, form a 3- to 6-membered saturated or partially unsaturated heterocyclic ring.

As defined generally above for formula III, one of $X^a$ and $X^b$ is selected from C and N and the other is C. In some embodiments of formula III, $X^a$ is N and $X^b$ is C. In some embodiments of formula III, $X^a$ is C and $X^b$ is N.

It will be appreciated that compounds of formula III wherein one of $X^a$ and $X^b$ is N have the structures:

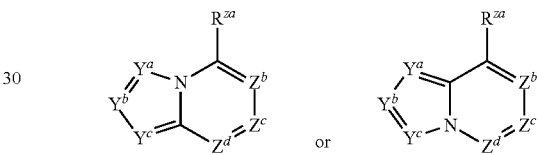

It is therefore understood that, due to the valence of $Y^a$ and $Y^c$ in such compounds of formula III, (i) $Y^a$ is selected from N and C—$R^{ya}$ and (ii) $Y^c$ is N.

As defined generally above for formula III, each $R^\dagger$ is independently selected from hydrogen and $C_{1-6}$ aliphatic optionally substituted with —OR''', —C(O)N(R''')$_2$, or —C(O)OR'''. In some embodiments of formula III, $R^\dagger$ is hydrogen. In some embodiments of formula III, $R^\dagger$ is $C_{1-6}$ aliphatic optionally substituted with —OR''', —C(O)N(R''')$_2$, or —C(O)OR'''. In some embodiments of formula III, $R^\dagger$ is $C_{1-6}$ aliphatic. In some such embodiments of formula III, $R^\dagger$ is $C_{1-6}$ alkyl. In some embodiments of formula III, $R^\dagger$ is —CH$_3$. In some embodiments of formula III, $R^\dagger$ is —CH$_2$CH$_3$. In some embodiments of formula III, $R^\dagger$ is —CH(CH$_3$)$_2$.

In some embodiments of formula III, $R^\dagger$ is $C_{1-6}$ aliphatic optionally substituted with —OR'''. In some embodiments of formula III, $R^\dagger$ is $C_{1-6}$ alkylene optionally substituted with —OR'''. In some embodiments of formula III, $R^\dagger$ is $C_{1-4}$ alkylene optionally substituted with —OR'''. In some embodiments of formula III, $R^\dagger$ is $C_{1-3}$ alkylene optionally substituted with —OR'''. In some embodiments of formula III, $R^\dagger$ is $C_{1-2}$ alkylene optionally substituted with —OR'''. In some embodiments, $R^\dagger$ is —(CH$_2$)$_{1-3}$OR'''. In some embodiments of formula III, $R^\dagger$ is —(CH$_2$)$_{2-3}$OR'''. In some embodiments of formula III, $R^\dagger$ is —(CH$_2$)$_2$OR'''. In some embodiments of formula III, $R^\dagger$ is —(CH$_2$)$_3$OR'''.

In some embodiments of formula III, $R^\dagger$ is $C_{1-6}$ aliphatic optionally substituted with —C(O)OR'''. In some embodiments of formula III, $R^\dagger$ is $C_{1-6}$ alkylene optionally substituted with —C(O)OR'''. In some embodiments of formula III, $R^\dagger$ is $C_{1-4}$ alkylene optionally substituted with —C(O)OR'''. In some embodiments of formula III, $R^\dagger$ is $C_{1-3}$ alkylene optionally substituted with —C(O)OR'''. In some embodiments of formula III, R† is $C_{1-2}$ alkylene optionally substituted with —C(O)OR'''. In some embodiments of formula III, R† is —(CH$_2$)$_{1-3}$C(O)OR'''. In some embodiments of formula III, R† is —(CH$_2$)$_{2-3}$C(O)OR'''. In some embodiments of formula III, R† is —CH$_2$C(O)OR'''. In some embodiments of formula III, R† is —(CH$_2$)$_2$C(O)OR'''.

In some embodiments of formula III, R† is $C_{1-6}$ aliphatic optionally substituted with —C(O)N(R)$_2$. In some embodiments of formula III, R† is $C_{1-6}$ alkylene optionally substituted with —C(O)N(R''')$_2$. In some embodiments of formula III, R† is $C_{1-4}$ alkylene optionally substituted with —C(O)N(R''')$_2$. In some embodiments of formula III, R† is $C_{1-3}$ alkylene optionally substituted with —C(O)N(R''')$_2$. In some embodiments of formula III, R† is $C_{1-2}$ alkylene optionally substituted with —C(O)N(R''')$_2$. In some embodiments of formula III, R† is —(CH$_2$)$_{1-3}$C(O)N(R''')$_2$. In some embodiments of formula III, R† is —(CH$_2$)$_{2-3}$C(O)N(R''')$_2$. In some embodiments of formula III, R† is —CH$_2$C(O)N(R''')$_2$. In some embodiments of formula III, R† is —(CH$_2$)$_2$C(O)N(R''')$_2$.

As defined generally above for formula III, each of $R^{ya}$, $R^{yb}$, $R^{za}$, $R^{zb}$, $R^{zc}$, and $R^{zd}$ is independently selected from hydrogen, halogen, —CN, —OR''', —C(O)OR''', and $C_{1-6}$ aliphatic optionally substituted with halogen, —CN, —OR''', —N(R''')$_2$, —C(O)OR''', or —C(O)N(R''')$_2$. In some embodiments of formula III, $R^{ya}$ is hydrogen. In some embodiments of formula III, $R^{ya}$ is halogen, —CN, —OR''', —C(O)OR''', or $C_{1-6}$ aliphatic optionally substituted with halogen, —CN, —OR''', —N(R''')$_2$, —C(O)OR''', or —C(O)N(R''')$_2$. In some embodiments of formula III, $R^{ya}$ is hydrogen, halogen or —OR'''. In some embodiments of formula III, $R^{ya}$ is halogen. In some such embodiments of formula III, $R^{ya}$ is chloro. In some embodiments of formula III, $R^{ya}$ is bromo. In some embodiments of formula III, $R^{ya}$ is iodo. In some embodiments of formula III, $R^{ya}$ is —OR'''. In some embodiments of formula III, $R^{ya}$ is —CN or —C(O)OR'''.

In some embodiments of formula III, $R^{yb}$ is hydrogen. In some embodiments of formula III, $R^{yb}$ is halogen, —CN, —OR''', —C(O)OR''', or $C_{1-6}$ aliphatic optionally substituted with halogen, —CN, —OR''', —N(R''')$_2$, —C(O)OR''', or —C(O)N(R''')$_2$. In some embodiments of formula III, $R^{yb}$ is hydrogen, —CN, —C(O)OR''' or $C_{1-6}$ aliphatic. In some embodiments of formula III, $R^{yb}$ is $C_{1-6}$ aliphatic. In some such embodiments of formula III, $R^{yb}$ is $C_{1-6}$ alkyl. In some embodiments of formula III, $R^{yb}$ is —CH$_3$. In some embodiments of formula III, $R^{yb}$ is —CN. In some embodiments of formula III, $R^{yb}$ is —C(O)OR'''. In some embodiments of formula III, $R^{yb}$ is —OR'''.

In some embodiments of formula III, $R^{za}$ is hydrogen. In some embodiments of formula III, $R^{za}$ is halogen, —CN, —OR''', —C(O)OR''', or $C_{1-6}$ aliphatic optionally substituted with halogen, —CN, —OR''', —N(R''')$_2$, —C(O)OR''', or —C(O)N(R''')$_2$. In some embodiments of formula III, $R^{za}$ is hydrogen or halogen. In some embodiments of formula III, $R^{za}$ is halogen. In some such embodiments of formula III, $R^{za}$ is bromo. In some embodiments of formula III, $R^{za}$ is —OR'''. In some embodiments of formula III, $R^{za}$ is —CN or —C(O)OR'''.

In some embodiments of formula III, $R^{zb}$ is hydrogen. In some embodiments of formula III, $R^{zb}$ is halogen, —CN, —OR''', —C(O)OR''', or $C_{1-6}$ aliphatic optionally substituted with halogen, —CN, —OR''', —N(R''')$_2$, —C(O)OR''', or —C(O)N(R''')$_2$. In some embodiments of formula III, $R^{zb}$ is $C_{1-6}$ aliphatic optionally substituted with halogen, —CN, —OR''', —N(R''')$_2$, —C(O)OR''', or —C(O)N(R''')$_2$. In some embodiments of formula III, $R^{zb}$ is hydrogen or $C_{1-6}$ aliphatic. In some embodiments of formula III, $R^{zb}$ is $C_{1-6}$ aliphatic. In some such embodiments of formula III, $R^{zb}$ is $C_{1-6}$ alkyl. In some embodiments of formula III, $R^{zb}$ is —CH$_3$. In some embodiments of formula III, $R^{zb}$ is —OR'''. In some embodiments of formula III, $R^{zb}$ is —CN or —C(O)OR'''.

In some embodiments of formula III, $R^{zc}$ is hydrogen. In some embodiments of formula III, $R^{zc}$ is halogen, —CN, —OR''', —C(O)OR''', or $C_{1-6}$ aliphatic optionally substituted with halogen, —CN, —OR''', —N(R''')$_2$, —C(O)OR''', or —C(O)N(R''')$_2$. In some embodiments of formula III, $R^{zc}$ is —OR'''. In some embodiments of formula III, $R^{zc}$ is —CN or —C(O)OR'''. In some embodiments of formula III, $R^{zc}$ is $C_{1-6}$ aliphatic optionally substituted with halogen, —CN, —OR''', —N(R''')$_2$, —C(O)OR''', or —C(O)N(R''')$_2$.

In some embodiments of formula III, Rd is hydrogen. In some embodiments of formula III, $R^{zd}$ is halogen, —CN, —OR''', —C(O)OR''', or $C_{1-6}$ aliphatic optionally substituted with halogen, —CN, —OR''', —N(R''')$_2$, —C(O)OR''', or —C(O)N(R''')$_2$. In some embodiments of formula III, $R^{zd}$ is halogen. In some such embodiments of formula III, $R^{zd}$ is chloro. In some embodiments of formula III, $R^{zd}$ is —OR'''. In some embodiments of formula III, $R^{zd}$ is $C_{1-6}$ aliphatic optionally substituted with halogen, —CN, —OR''', —N(R''')$_2$, —C(O)OR''', or —C(O)N(R''')$_2$. In some embodiments of formula III, $R^{zd}$ is —C(O)OR'''. In some embodiments of formula III, $R^{zd}$ is —CN.

As defined generally above for formula III, $Y^a$ is selected from N, N—R† and C—$R^{ya}$. In some embodiments of formula III, $Y^a$ is N. In some embodiments of formula III, $Y^a$ is N—R†. In some embodiments of formula III, $Y^a$ is C—$R^{ya}$.

As defined generally above for formula III, $Y^b$ is selected from N and C—$R^{yb}$. In some embodiments of formula III, $Y^b$ is N. In some embodiments of formula III, $Y^b$ is C—$R^{yb}$.

As defined generally above for formula III, $Y^c$ is selected from N, N—R†, O, S, and S(O)$_2$. In some embodiments of formula III, $Y^c$ is selected from N—R†, O, S, and S(O)$_2$. In some embodiments of formula III, $Y^c$ is selected from N—R†, O, and S. In some embodiments of formula III, $Y^c$ is N. In some embodiments of formula III, $Y^c$ is N—R†. In some embodiments of formula III, $Y^c$ is O. In some embodiments of formula III, $Y^c$ is S. In some embodiments of formula III, $Y^c$ is S(O)$_2$.

As defined generally above for formula III, $Z^b$ is selected from N and C—$R^{zb}$. In some embodiments of formula III, $Z^b$ is N. In some embodiments of formula III, $Z^b$ is C—$R^{zb}$.

As defined generally above for formula III, $Z^c$ is selected from N and C—$R^{zc}$. In some embodiments of formula III, $Z^c$ is N. In some embodiments of formula III, $Z^c$ is C—$R^{zc}$.

As defined generally above for formula III, $Z^d$ is selected from N and C—$R^{zd}$. In some embodiments of formula III, $Z^d$ is N. In some embodiments of formula III, $Z^d$ is C—$R^{zd}$.

As defined generally above for formula III, each R''' is independently selected from hydrogen and $C_{1-6}$ aliphatic, or two instances of R''', together with the atom to which they are attached, form a 3- to 6-membered saturated or partially unsaturated heterocyclic ring. In some embodiments of formula III, R''' is hydrogen. In some embodiments of formula III, R''' is $C_{1-6}$ aliphatic. In some such embodiments of formula III, R''' is $C_{1-6}$ alkyl. In some embodiments of formula III, R''' is —CH$_3$. In some embodiments of formula III, R''' is selected from hydrogen and —CH$_3$.

In some embodiments of formula III, $Z^c$ is N. Accordingly, in some embodiments, the SARM1 inhibitor is a compound of formula III-a:

III-a

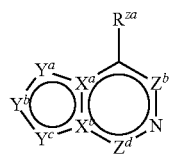

or a pharmaceutically acceptable salt thereof.

In some embodiments of formula III, $X^a$ is N and $X^b$ is C. Accordingly, in some embodiments, the SARM1 inhibitor is a compound of formula III-b:

III-b

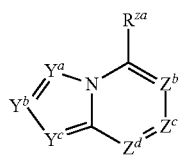

or a pharmaceutically acceptable salt thereof.

In some embodiments of Formula III, $X^a$ is C and $X^b$ is N. Accordingly, in some embodiments, the SARM1 inhibitor is a compound of formula III-c:

III-c

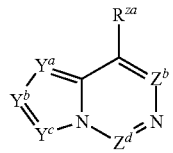

or a pharmaceutically acceptable salt thereof.

In some embodiments of formula III, the SARM1 inhibitor is a compound of any one of formula III-a-i, III-a-ii, III-a-iii, III-a-iv, III-a-v, III-b-i, III-b-ii, III-c-i, or III-c-ii:

III-a-i

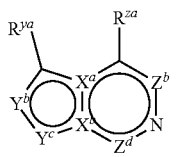

III-a-ii

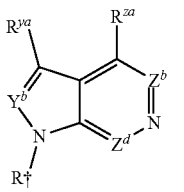

III-a-iii

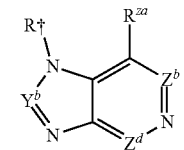

III-a-iv

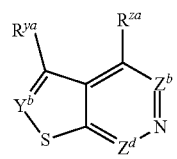

III-a-v

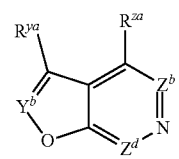

III-b-i

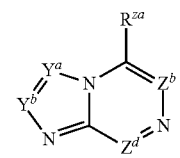

III-b-ii

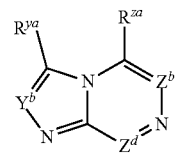

III-c-i

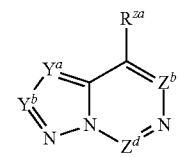

III-c-ii

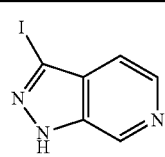

or a pharmaceutically acceptable salt thereof, wherein each of $X^a$, $X^b$, $Y^a$, $Y^b$, $Y^c$, $Z^b$, $Z^d$, $R^{ya}$, $R^{za}$, and $R^\dagger$ is as defined above and described herein.

In some embodiments, a compound of formula III is selected from:

| Example | Structure |
| --- | --- |
| III-1 | 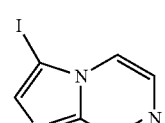 |
| III-2 | 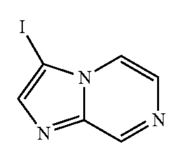 |

-continued
| Example | Structure |
|---|---|
| III-3 | 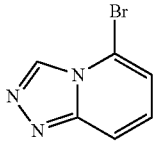 |
| III-4 | 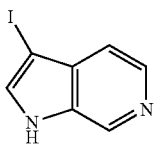 |
| III-5 | 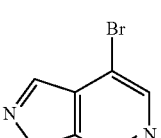 |
| III-6 | 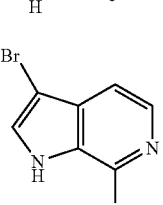 |
| III-7 | 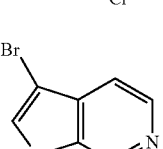 |
| III-8 | 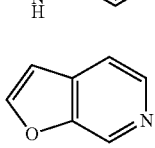 |
| III-9 | 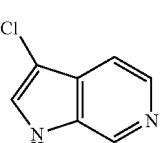 |
| III-10 | 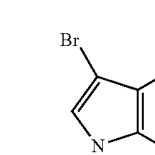 |
| III-11 | 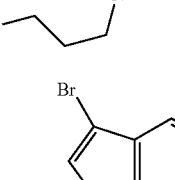 |
-continued
| Example | Structure |
|---|---|
| III-12 | 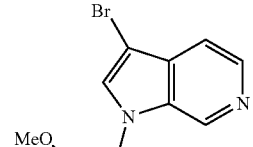 |
| III-13 | 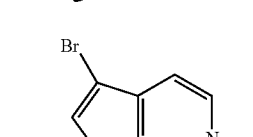 |
| III-14 | 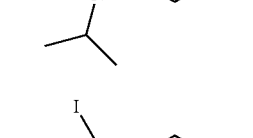 |
| III-15 | 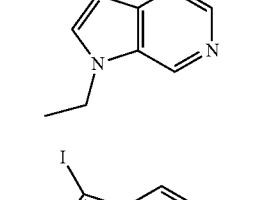 |
| III-16 | 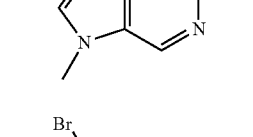 |
| III-17 | 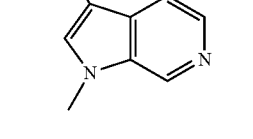 |
| III-18 | 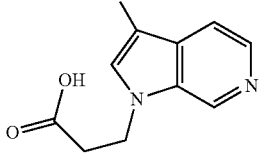 |
| III-19 | 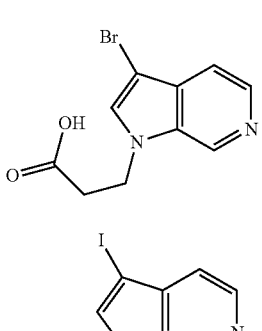 |

| Example | Structure |
|---|---|
| III-20 | 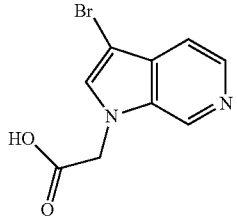 [SMILES: O=C(O)Cn1cc(Br)c2ccncc21] |
| III-21 | 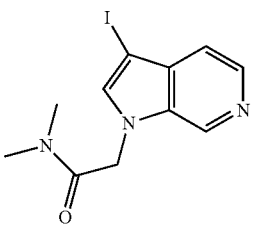 [SMILES: CN(C)C(=O)Cn1cc(I)c2ccncc21] |
| III-22 | 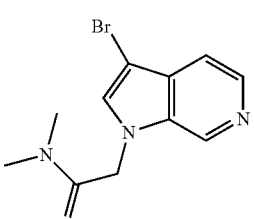 |
| III-23 | 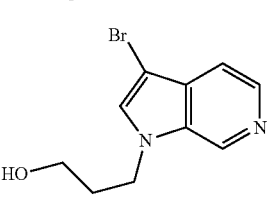 [SMILES: OCCCn1cc(Br)c2ccncc21] |
| III-24 | 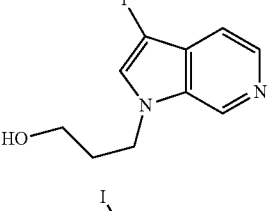 |
| III-25 | 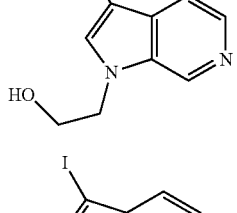 |
| III-26 | 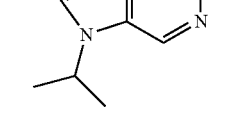 |
| III-27 | 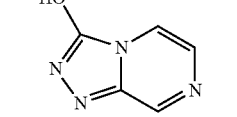 |
| III-28 | 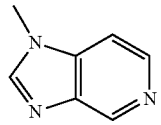 |
| III-29 | 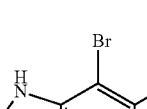 |
| III-30 | 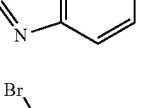 |
| III-31 | 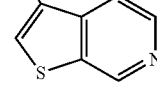 |
| III-32 | 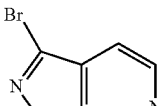 |
| III-33 | 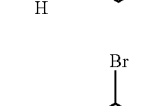 |
| III-34 | 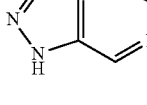 |
| III-35 | 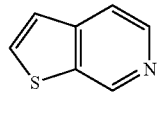 |
| III-36 | 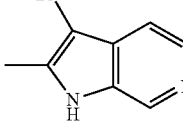 |
| III-37 | 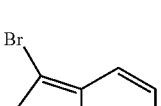 |

| Example | Structure |
|---------|-----------|
| III-38 | ethyl 3-bromo-1H-pyrrolo[2,3-c]pyridine-2-carboxylate |
| III-39 | ethyl 3-iodo-1H-pyrrolo[2,3-c]pyridine-2-carboxylate |
| III-40 | 3-bromo-thieno[2,3-c]pyridine 7,7-dioxide |
| III-41 | 7-iodo-thieno[2,3-d]pyridazine |
| III-42 | 4-iodo-1H-pyrrolo[2,3-d]pyridazine |
| III-43 | 7-bromo-thieno[2,3-d]pyridazine |
| III-44 | 4-bromo-1H-pyrrolo[2,3-c]pyridazine | or a pharmaceutically acceptable salt thereof.

DLK Inhibitors

In some embodiments, the DLK inhibitor is a small molecule, a polypeptide, a peptide fragment, a nucleic acid (e.g., a siRNA, an antisense oligonucleotide, a micro-RNA, or an aptamer), an antibody, a dominant-negative inhibitor, or a ribozyme.

In some embodiments, the DLK inhibitor is a small molecule. In some embodiments, the DLK inhibitor is a siRNA. In some embodiments, the DLK inhibitor is an antisense oligonucleotide. In some embodiments, the DLK inhibitor is a polypeptide. In some embodiments, a DLK inhibitor is a peptide fragment. In some embodiments, a DLK inhibitor is a nucleic acid. In some embodiments, a DLK inhibitor is an antisense oligonucleotide.

In some embodiments, an inhibitor of DLK inhibits downstream JNK-phosphorylation by reducing DLK expression.

In some embodiments, the DLK inhibitor is CGD-0134 (RG6000).

In some embodiments, the DLK inhibitor one is described in Patel et al. *J Med Chem.* 2015 Jan. 8; 58(1):401-18, hereby incorporated by reference in its entirety. For example, in some such embodiments, the DLK inhibitor is GNE-3511.

In some embodiments, the DLK inhibitor is a compound described in WO 2013/177367, hereby incorporated by reference in its entirety. For example, in some such embodiments, the DLK inhibitor is SR8165.

In some embodiments, the DLK inhibitor is described in WO 2005/021729, WO 2009/011546, U.S. Pat. No. 8,754,060, WO 2013/174780, WO 2011/050192, WO 2013/134766, WO 2014/111496, US 2016/0158234, WO 2014/177060, WO 2014/177524, US 2015/0175619, WO 2015/091889, WO 2016/142310, WO 2018/044808, and US 2018/0057507, each of which is hereby incorporated by reference in its entirety.

In some embodiments, the DLK inhibitor is a compound described in Shu, M. *J Med Chem.* 2018, Patel, S. *J Med Chem.* 2017, 60(19):8083-8102, Welsbie, D. S., *Neuron.* 2017, 94(6):1142-1154, Blondeau et al., *Neural Dev.* 2016, 11(1):13, Yin, C. et al., *Neuropharmacology.* 2016, 108:316-23, and Holland, S. M. et al., *Proc Natl Acad Sci USA.* 2016, 113(3):763-8, each of which is hereby incorporated by reference in its entirety.

In some embodiments, the DLK inhibitor is selected from:

| Structure | Name |
|-----------|------|
| (structure shown) | GNE-3511<br>2-((6-(3,3-difluoropyrrolidin-1-yl)-4-(1-(oxetan-3-yl)piperidin-4-yl)pyridin-2-yl)amino)isonicotinonitrile |

| Structure | Name |
|---|---|
| | (3-(6-((4-methoxypyridin-2-yl)amino)-2-methylpyrimidin-4-yl)piperidin-1-yl)(phenyl)methanone |
| | 2-((1-cyclopentyl-5-(1-(oxetan-3-yl)piperidin-4-yl)-1H-pyrazol-3-yl)amino)isonicotinonitrile |
| 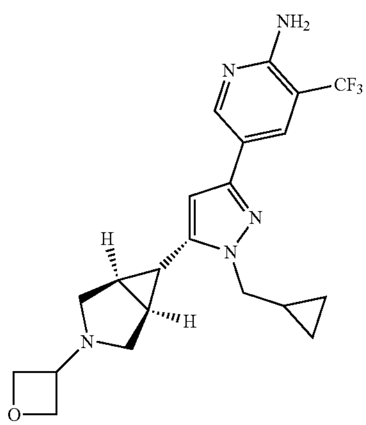 | 5-(1-(cyclopropylmethyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine |
| 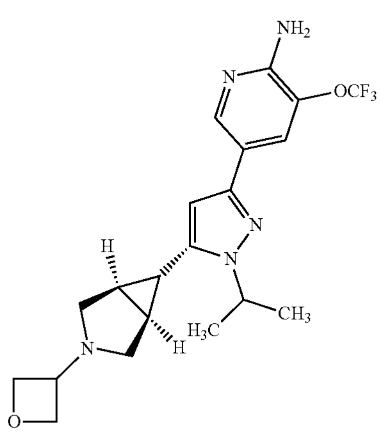 | 5-(1-isopropyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine |

-continued

| Structure | Name |
|---|---|
| | N-(4-chloropyridin-2-yl)-2-(3,3-difluoropyrrolidin-1-yl)-6-(piperidin-4-yl)pyrimidin-4-amine |
| | 5-(1-isobutyl-(1R,5S,6r)-3-(4-methylpiperazin-1-yl)bicyclo[3.1.0]hexan-6-yl)-1H-imidazol-4-yl)-3-(trifluoromethyl)pyridin-2-amine |
| | SR8165<br>(Z)-3-((4-((2-(diethylamino)ethyl)carbamoyl)-3,5-dimethyl-1H-pyrrol-2-yl)methylene)-N,N-dimethyl-2-oxoindoline-5-carboxamide |
| | 5-(5-((1R,3r,5S,6r)-3-(hexahydropyrrolo[1,2-a]pyrazin-2(1H)-yl)bicyclo[3.1.0]hexan-6-yl)-1-isopropyl-1H-pyrazol-3-yl)-3-(trifluoromethyl)pyridin-2-amine |

-continued

| Structure | Name |
|---|---|
| 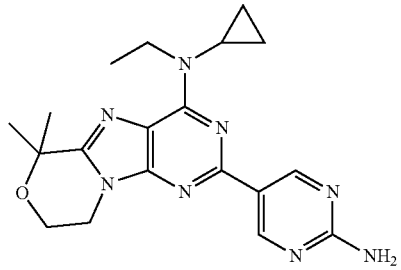 [SMILES: CCN(c1nc(-c2cnc(N)nc2)nc2c1nc1n2CCOC1(C)C)C1CC1] | 2-(2-aminopyrimidin-5-yl)-N-cyclopropyl-N-ethyl-6,6-dimethyl-8,9-dihydro-6H-[1,4]oxazino[4,3-e]purin-4-amine |

In some embodiments, a DLK inhibitor is a siRNA. In some embodiments, a DLK inhibitor is a siRNA inhibitor selected from:

```
(forward primer)
                                (SEQ ID NO: 1)
GCUCAGGCGAGAGCAAGCUUUAGAA (reverse primer)
                                (SEQ ID NO: 2)
UUCUAAAGCUUGCUCUCGCCUGAGC (forward primer)
                                (SEQ ID NO: 3)
CCCUCAUGUUGCAACUAGAACUCAA (reverse primer)
                                (SEQ ID NO: 4)
UUGAGUUCUAGUUGCAACAUGAGGG (forward primer)
                                (SEQ ID NO: 5)
CCAAUAGUGUCCUGCAGCUACAUGA (reverse primer)
                                (SEQ ID NO: 6)
UCAUGUAGCUGCAGGACACUAUUGG
```

In some embodiments, a siRNA that targets DLK is described in Yin, C., et al., *Neurobiol Dis.* 2017 July; 103:133-143.

In some embodiments, a method of DLK inhibition is described in WO 2014/134349, which is hereby incorporated by reference in its entirety. In some embodiments, a DLK inhibitor is described in Summers, D. W., *Proc Natl Acad Sci USA.* 2018, 115(37):E8746-E8754, which is hereby incorporated by reference in its entirety.

In some embodiments, a DLK inhibitor is a shRNA. In some embodiments, a DLK inhibitor is a shRNA with a targeting sequence selected from:

```
                                (SEQ ID NO: 7)
CATCATCTGGGTGTGGGAAG (SEQ ID NO: 8)
AAGTTGGCAGCACCAACACTGATGAGCGA (SEQ ID NO: 9)
AAGGAGGATGTCCTGGTCTACTGAAGTCAC (SEQ ID NO: 10)
CCTGTCTGGACAATGATTGGCAAAGCCTA (SEQ ID NO: 11)
GAGTAGCCTGGATGGCTCCTGAAGTGATC
```

In some embodiments, a DLK inhibitor is a shRNA sequence as described in Sheu, M. L., *Int J Mol Sci.* 2018, 19(8): E2421 or Simard-Bisson et al., *J Invest Dermatol.* 2017, (1):132-141, each of which is hereby incorporated by reference in its entirety.

NAMPT Inhibitors

In some embodiments, the NAMPT inhibitor is a small molecule, a polypeptide, a peptide fragment, a nucleic acid (e.g., a siRNA, an antisense oligonucleotide, a micro-RNA, or an aptamer), an antibody, a dominant-negative inhibitor, or a ribozyme.

In some embodiments, the NAMPT inhibitor is a small molecule. In some embodiments, the NAMPT inhibitor is a siRNA. In some embodiments, the NAMPT inhibitor is an antisense oligonucleotide. In some embodiments, the NAMPT inhibitor is a polypeptide. In some embodiments, a NAMPT inhibitor is a peptide fragment. In some embodiments, a NAMPT inhibitor is a nucleic acid. In some embodiments, a NAMPT inhibitor is an antisense oligonucleotide.

In some embodiments, a NAMPT inhibitor prevents the formation of nicotinamide mononucleotide (NMN). In some embodiments, inhibition of NAMPT inhibits the mammalian NAD+ salvage pathway.

In some embodiments, the NAMPT inhibitor is selected from:

| Structure | Name |
|---|---|
| 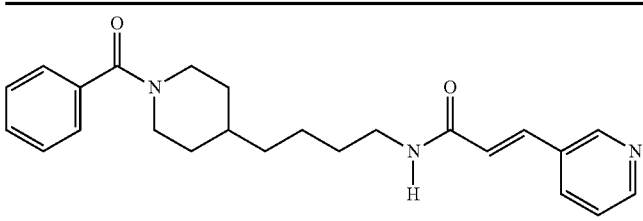  FK866 (MW = 391.5) | FK866  N-[4-(1-benzoylpiperidin-4-yl)butyl]-3-(pyridin-3-yl) acrylamide  CAS No. 658084-64-1 |

-continued

| Structure | Name |
|---|---|
| 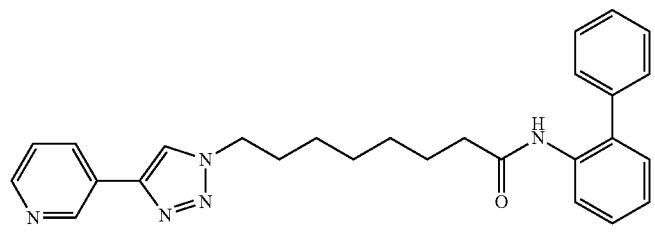 [SMILES: O=C(CCCCCCCn1cc(-c2cccnc2)nn1)Nc1ccccc1-c1ccccc1] | GPP78<br>N-([1,1'-biphenyl]-2-yl)-8-(4-(pyridin-3-yl)-1H-1,2,3-triazol-1-yl)octanamide<br>CAS No. 1202580-59-3 |
| 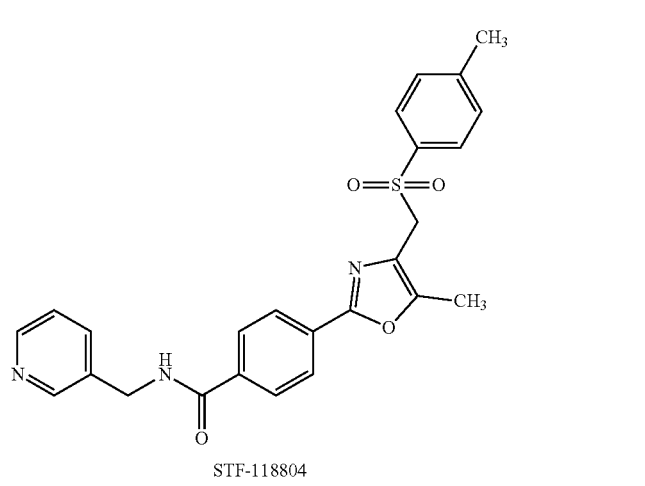 [SMILES: Cc1ccc(S(=O)(=O)Cc2nc(-c3ccc(C(=O)NCc4cccnc4)cc3)oc2C)cc1]STF-118804 | STF 118804<br>4-[5-Methyl-4-[[(4-methylphenyl)sulfonyl[methyl]-2-oxazolyl]-N-(3-pyridinylmethyl)benzamide<br>CAS No 894187-61-2 |
| 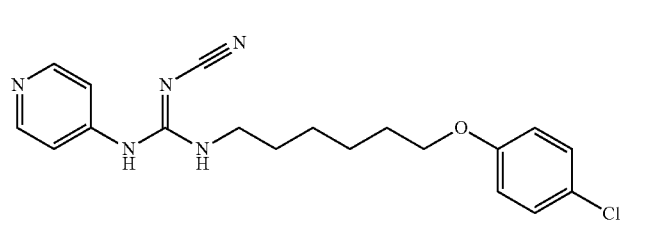 [SMILES: N#C/N=C(\NCCCCCCOc1ccc(Cl)cc1)Nc1ccncc1] | CHS-828<br>(E)-1-[6-(4-chlorophenoxy)hexyl]-2-cyano-3-(pyridin-4-yl)guanidine (Travelli et al., 2011)<br>CAS No. 200484-11-3 |
| 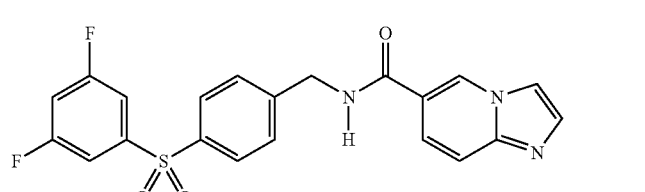 | GNE-617<br>N-[[4-[3,5-difluorophenyl)sulfonyl]phenyl]methyl]-imidazo[1,2-A]pyridine-6-carboxamide<br>CAS No. 1352154-70-8 |
| 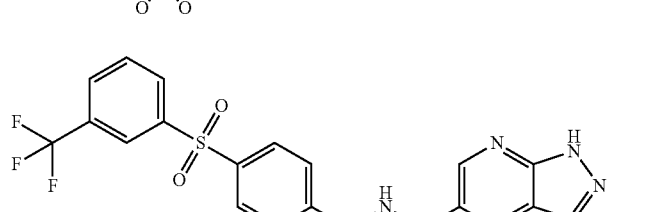 | GNE-618<br>N-[[4-[[3-(Trifluoromethyl)phenyl]sulfonyl]phenyl]methyl]-1H-pyrazolo[3,4-b]pyridine-5-carboxamide<br>CAS No. 1362151-42-5 |
| 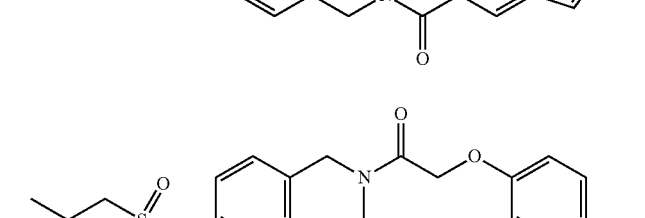 | LSN3154567 (Nampt-IN-1)<br>2-Hydroxy-2-methyl-N-[1,2,3,4-tetrahydro-2-[2-(3-pyridinyloxy)acetyl]-6-isoquinolinyl]-1-propanesulfonamide<br>CAS No.: 1698878-14-6 |

| Structure | Name |
|---|---|
| 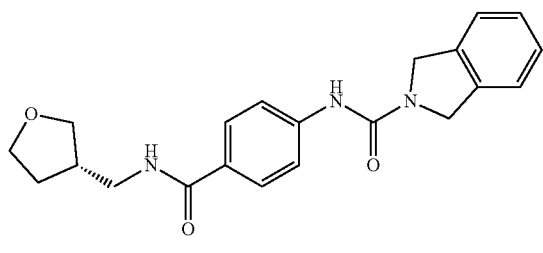 A-1293201 | A-1293201<br>Wilsbacher et al., 2017 |
| 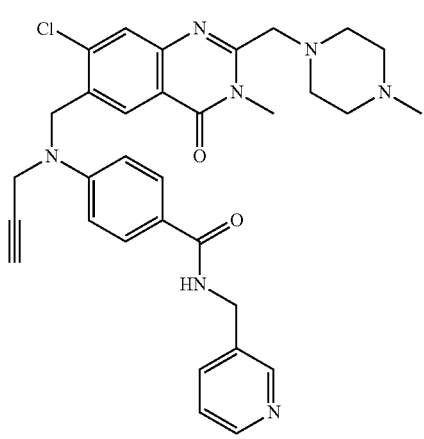 [SMILES: C#CCN(Cc1cc2c(=O)n(C)c(CN3CCN(C)CC3)nc2cc1Cl)c1ccc(C(=O)NCc2cccnc2)cc1] | CB-300919<br>4-(((7-chloro-3,4-dihydro-3-methyl-2-((4-methyl-1-piperazinyl)methyl)-4-oxo-6-quinazolinyl)methyl)-2-propyn-1-ylamino)-N-(3-pyridinylmethyl)-Benzamide<br>CAS No 289715-28-2 |
| 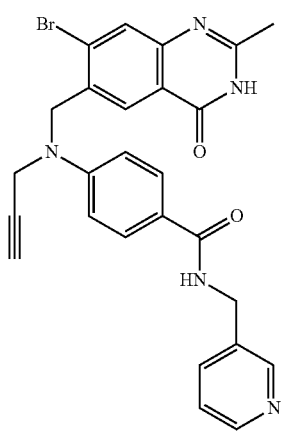 [SMILES: C#CCN(Cc1cc2c(=O)[nH]c(C)nc2cc1Br)c1ccc(C(=O)NCc2cccnc2)cc1] | CB-30865<br>4-(((7-bromo-2-methyl-4-oxo-1,4-dihydroquinazolin-6-yl)methyl)(prop-2-yn-1-yl)amino)-N-(pyridin-3-ylmethyl)benzamide<br>CAS No 206275-15-2 |
| 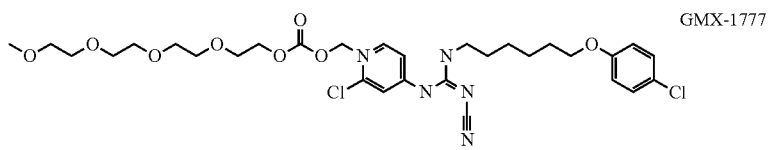 EB1627 | GMX-1777 |

In some embodiments, the NAMPT inhibitor is a compound described in Travelli, C. et al., *J. Pharmacol. Exp. Ther.* 2011, 388(3):829-40; Hasmann, M. and Schemainda, I. *Cancer Res.* 2003, 63(21):7436-42; Galli et al., *ChemMedChem.* 2008, 3(5):771-9; Colombano, G. et al., *J. Med Chem.* 2010, 53(2):616-23; Matheny, C. J. *Chem. Biol.* 2013, 20(11):1352-63; Chan, D. A., et al., *Sci. Trans. Med.* 2011, 3(94):94ra70; Adams, D. J., et al., *ACS Chem. Biol.* 2014, 9(10):2247-54; Kroop, E. M., et al., *Stem Cells Transl Med.* 2015, 4(5):483-93; von Heideman, A., et al., *Cancer Chemother Pharmacol.* 2010, 65(6):1165-72; Lovborg, H., et al., *BMC Res Notes.* 2009, 2:114; Olesen, U. H., et al., *Biochem Biophys Res Commun.,* 2008, 367(4):799-804; Hassan, S. B., et al., *Anticancer Res.,* 2006, 26(6B):4431-6; Johanson, V., et al., *Neuroendocrinology.* 2005, 82(3-4): 171-6, Friberg, L. E., et al., *Eur J Pharm Sci.,* 2005, 25(1):163-73; Ravaud, A., et al., *Eur J. Cancer.* 2005, 41(5):702-7; Olsen, L. S., et al., Int J. Cancer. 2004, 111(2): 198-205; Lovborg, H., et al., *Mol Cancer Ther.* 2004, 3(5):521-6; Zheng, X., *J. Med. Chem.* 2013, 56(16): 6413-

33; Wang, W. et al, *PLoS One,* 2014, 9(10) e109366; O'Brien, T. et al., *Neoplasia.* 2013, 15(12): 1314-29, Xiao, T. et al., *Neoplasia.* 2013, 15(10): 1151-60; Zhao, G. et al., *Cancer Ther.* 2017, 16(12): 2677-88; Guo, J. et al., *Biochem Biophys Res Commun.* 2017, 491(3):681-6; Lockman, J. W. et al., *J. Med. Chem.,* 2010, 53(24):8734-46; Fleischer, T. C. et al., *Chem. Biol.* 2010, 17(6): 659-64, Bavetsias, V. et al., *J. Med. Chem.,* 2002, 45(17): 3692-702; Hiorns, L. R. et al., *J Inorg Biochem.* 1999, 77(1-2):95-104; Preyat, N. and Leo, O. *Biochem Pharmacol.* 2016, 101:13-26; Chan. M. et al., *Cancer Res.* 2014, 74(21):5948-54; Olesen, U. H. et al., *BMC Cancer.* 2010, 10:677; Bi, T. Q. and Che, X. M. *Cancer Biol Ther.* 2010, 10(2):119-25; Fuchs, D. et al., *Int J Cancer.* 2010, 126(12):2773-89; Kato, H. et al., *Clin Cancer Res.* 2010, 16(3):898-911; Watson, M. et al., *Mol Cell Biol.* 2009, 29(21):5872-88; Beauparlant, P. et al., *Anticancer Drugs.* 2009, 20(5):346-54; Rane, C. et al., *Sci Rep.* 2017, 7:42555; Fulciniti, M. et al., *Blood.* 2017, pii: blood-2016-06-724831; Aboukameel, A. et al., *Mol Cancer Ther.* 2017, 16(1):76-87; and Abu Aboud, O. et al. *Mol Cancer Ther.* 2016, 15(9): 2119-29, each of which is hereby incorporated by reference in its entirety.

Compositions

In some embodiments, the present disclosure provides compositions that comprise and/or deliver a SARM1 inhibitor (e.g., in a form as described herein), a prodrug or active metabolite thereof. In certain embodiments, a composition comprising a SARM1 inhibitor is formulated for use in administering to a subject in combination with a DLK inhibitor.

In some embodiments, the present disclosure provides compositions comprising a SARM1 inhibitor for use in combination with a DLK inhibitor. In some embodiments, such compositions are pharmaceutical compositions that include at least one pharmaceutically acceptable carrier, diluent or excipient. In some embodiments, the present disclosure provides compositions that comprise and/or deliver a compound of Formula I, II, or III with a DLK inhibitor. In some embodiments, such compositions are pharmaceutically acceptable compositions that include at least one pharmaceutically acceptable carrier.

In some embodiments, provided methods comprise administering a composition comprising a SARM1 inhibitor and one or more pharmaceutically acceptable excipients. The amount of SARM1 inhibitor in provided compositions is such that is effective to measurably inhibit axonal degeneration and/or measurably affect a change in a biomarker of neurodegeneration in a biological sample or in a subject. In certain embodiments, a composition comprising a SARM1 inhibitor is formulated for administration to a subject in need of such composition. The compounds and compositions, according to the methods of the present disclosure, may be administered using any amount and any route of administration effective for treating or lessening the severity of any disease or disorder described herein. SARM1 inhibitors are preferably formulated in unit dosage form for ease of administration and uniformity of dosage. The expression "unit dosage form" as used herein refers to a physically discrete unit of agent appropriate for the subject to be treated. It will be understood, however, that the total daily usage of the SARM1 inhibitors will be decided by the attending physician within the scope of sound medical judgment. The specific effective dose level for any particular subject or organism will vary from subject to subject, depending on a variety of factors, including the disorder being treated and the severity of the disorder; the activity of the specific compound employed; the specific composition employed and its route of administration; the species, age, body weight, sex and diet of the subject; the general condition of the subject; the time of administration; the rate of excretion of the specific compound employed; the duration of the treatment; drugs used in combination or coincidental with the specific compound employed, and the like.

EXEMPLIFICATION

The present teachings including descriptions provided in the Examples that are not intended to limit the scope of any claim. Unless specifically presented in the past tense, inclusion in the Examples is not intended to imply that the experiments were actually performed. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Materials and Methods

Methods and compositions described herein utilize laboratory techniques well known to persons skilled in the art, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Methods In Molecular Biology, ed. Richard, Humana Press, N J, 1995; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999. Methods of administration of pharmaceuticals and dosage regimes, can be determined according to standard principles of pharmacology, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

Example 1

Activated SARM1 is a highly effective NADase that depletes local axonal NAD+ reserves within minutes to a few hours after activation, leading to a local bioenergetic crisis within this important neuronal compartment, followed by rapid axonal degeneration. The axon degeneration assay, as described herein, demonstrates the effect of treating injured axons with a SARM1 inhibitor in combination with a DLK inhibitor.

Mouse DRG Drop Culture

Primary embryonic dorsal root ganglia (DRG) cells were isolated from embryonic day (E) 12.5 CD1 mouse embryos. Mouse dorsal root ganglion neurons (DRGs) were dissected out of E12.5 CD1 mice (50 ganglia per embryo) and incubated with 0.5% Trypsin solution containing 0.02% EDTA (Gibco) at 37° C. for 15 min. The cells were then triturated by gentle pipetting and washed 3 times with DRG growth medium (Neurobasal medium (Gibco) containing 2% B27 (Invitrogen), 100 ng/ml 2.5S NGF (Harland Bioproducts), 1 mM 5-fluoro-2' deoxyuridine (Sigma), penicillin, and streptomycin). Cells were suspended in the DRG growth medium. DRG drop cultures were created by spotting 5000 cells/well into the center of each well of a 96-well tissue culture plate coated with poly-D-Lysine (0.1 mg/ml; Sigma) and laminin (3 mg/ml; Invitrogen). Cells were allowed to adhere to the plates in a humidified tissue culture incubator (5% $CO_2$) for 15 min and then DRG growth medium was gently added (100 ml well). DRG neurons were maintained in neurobasal medium supplemented with L-glutamine (Invitrogen), 2% (vol/vol) B27 (Invitrogen), 50 ng/mL NGF (Harlan Laboratories), and 1 µM 5-fluoro-2'deoxyuridine plus 1 µM uridine (Sigma) to induce death of mitotic cells. DRG neurons were then seeded on plates pre-coated with poly-D-lysine and laminin.

Axon Degeneration Assay

To study the axonal protective effects of combining a DLK inhibitor with a SARM1 inhibitor, 6 day-old mouse DRG drop cultures were preincubated with either 100 nM or 300 nM of DLK inhibitor (GNE-3511) for 24 hours before axotomy. 2 hours prior to axotomy, DRG cultures were treated with SARM1 inhibitors, in the continued presence of the DLK inhibitor. Potent SARM1 inhibitors were selected from two classes: isoquinoline and isothiazole SARM1 inhibitors. Isoquinoline SARM1 inhibitors tested included I-26 and I-86, while isothiazole SARM1 inhibitors tested included II-6 and II-32. The SARM1 inhibitors were tested using concentrations ranging from 0.1 to 30 µM.

A manual axotomy was performed at time 0 by transecting the axons of the DRG neurons with a blade. After the axotomy, DRG cultures remained exposed to the SARM1 inhibitor alone, DLK inhibitor alone, or the combination of SARM1 inhibitor and DLK inhibitor. At 16 hours, DRG cultures were fixed in a buffered solution containing 1% PFA and sucrose and stored at 4° C. prior to imaging. Bright-field images of DRG axons and cell bodies were collected using the 20× water immersion lens of a Phenix automated confocal microscope (PerkinElmer) and quantitation of axonal damage was performed using in-house developed scripts (Acapella, PerkinElmer). The effect of DLK inhibitor alone in protecting distal axons from fragmentation was determined at concentrations of 100 nM and 300 nM. The effect of combining the DLK inhibitor with varying concentrations of a SARM1 inhibitor was compared to the individual protective effects of either 100 nM or 300 nM of DLK inhibitor alone or an equivalent concentration of a SARM1 inhibitor alone.

Results

Figure 1B:
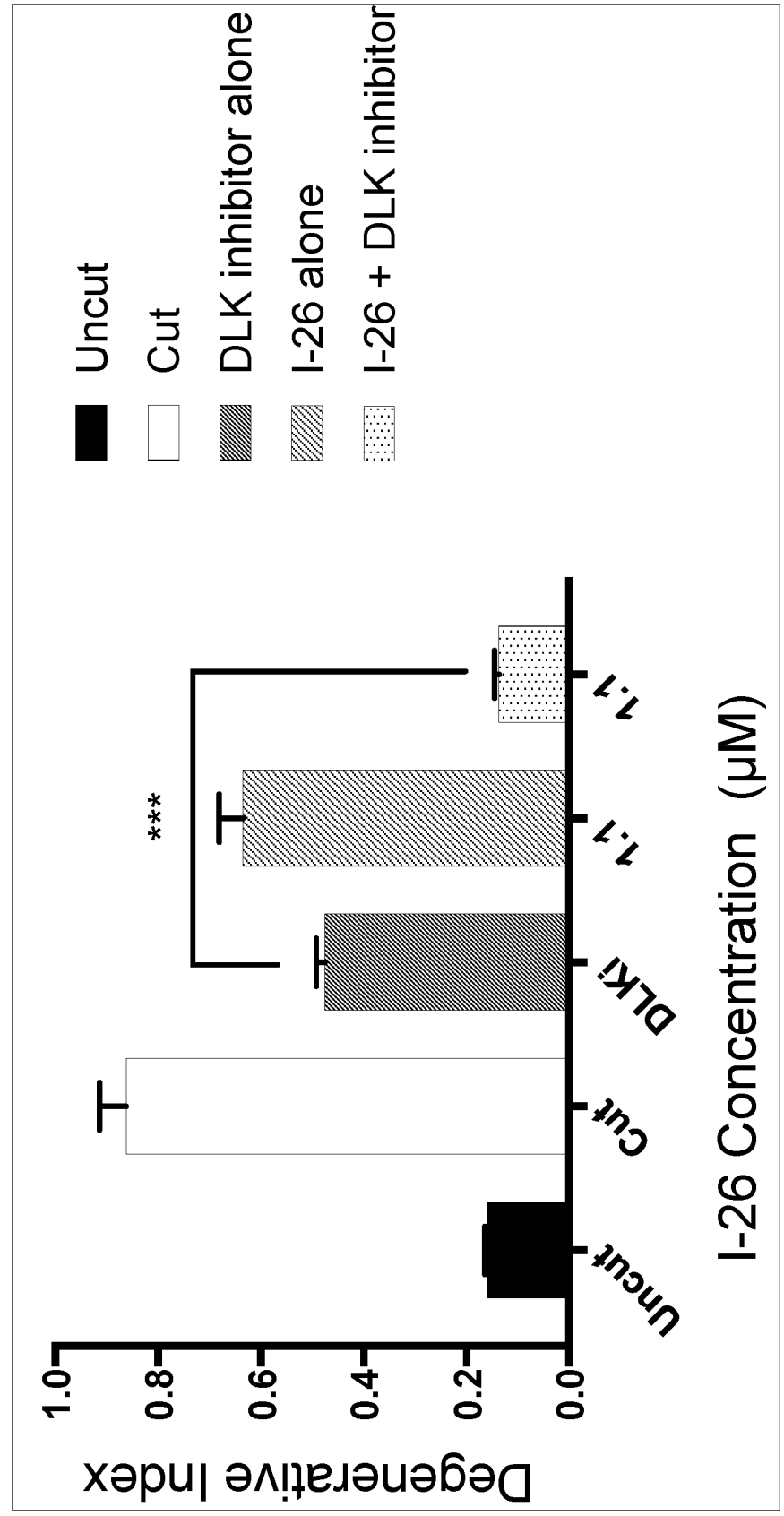

A potent SARM1 inhibitor, I-26, was used to evaluate the axonal protective effect of SARM1 inhibition when administered with a DLK inhibitor, GNE-3551, on the axon degeneration assay described herein. As shown in FIG. 1, the combination of compound I-26 with a DLK inhibitor increases neuroprotection post-axotomy as compared to single agent therapy. For each concentration of compound I-26 tested, the extent of axonal protection of a combination of compound I-26+DLK inhibitor was always compared to the amount of protection produced by the agent in the combination that, individually, had the greater protective effect. FIGS. 1A and 1B show the degeneration index of DRG axons 16 hours post-axotomy. In FIG. 1A, 100 nM DLK inhibitor provided no axonal protection, whereas compound I-26 demonstrated significant axonal protection over all tested concentrations. The addition of 100 nM DLK inhibitor to the concentration of compound I-26 being tested provided a further, though not significant, reduction in axonal degeneration. In FIG. 1B, 300 nM DLK inhibitor alone or 1.1 µM of compound I-26 alone, provided a modest level of protection. Surprisingly, the combination of 1.1 µM compound I-26+300 nM DLK inhibitor provided robust and statistically significant protection. Furthermore, the magnitude of the combined effect of 1.1 µM compound I-26 and 300 nM DLK inhibitor is greater than the sum of the individual effects of either agent alone, indicating that the effect of combining these agents is not simply additive but in fact synergistic and could not have been predicted from the individual effect of each agent in isolation.

Figure 2A:
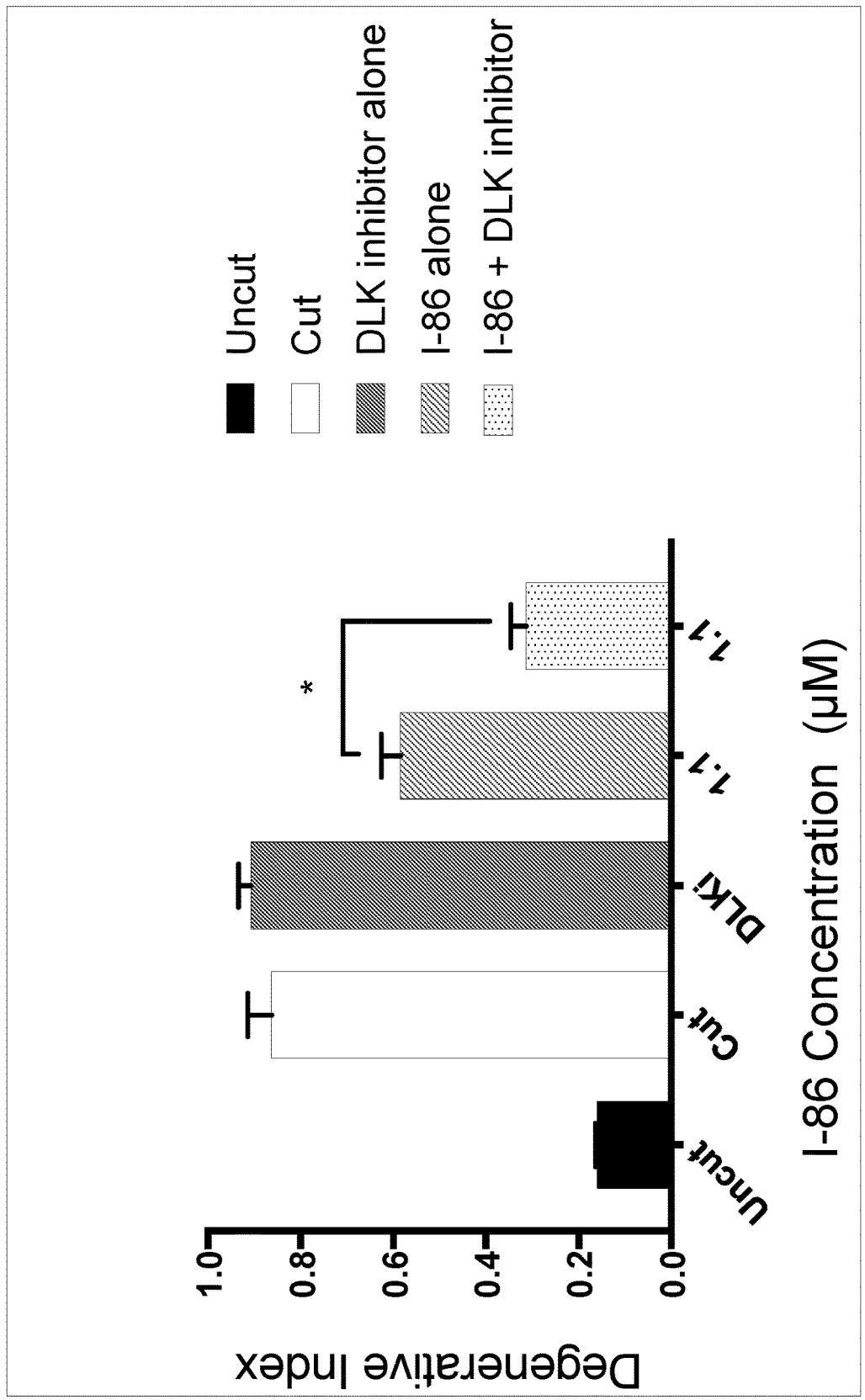
FIG. 2A and FIG. 2B illustrate that the combination of compound I-86, a SARM1 inhibitor, with the DLK inhibitor (GNE-3511) increases neuroprotection post-axotomy as compared to single agent therapy. For the concentration of compound I-86 tested, the extent of axonal protection of a combination of compound I-86+DLK inhibitor was compared to the amount of protection produced by the agent in that combination that, individually, had the greater protective effect.
Figure 2B:
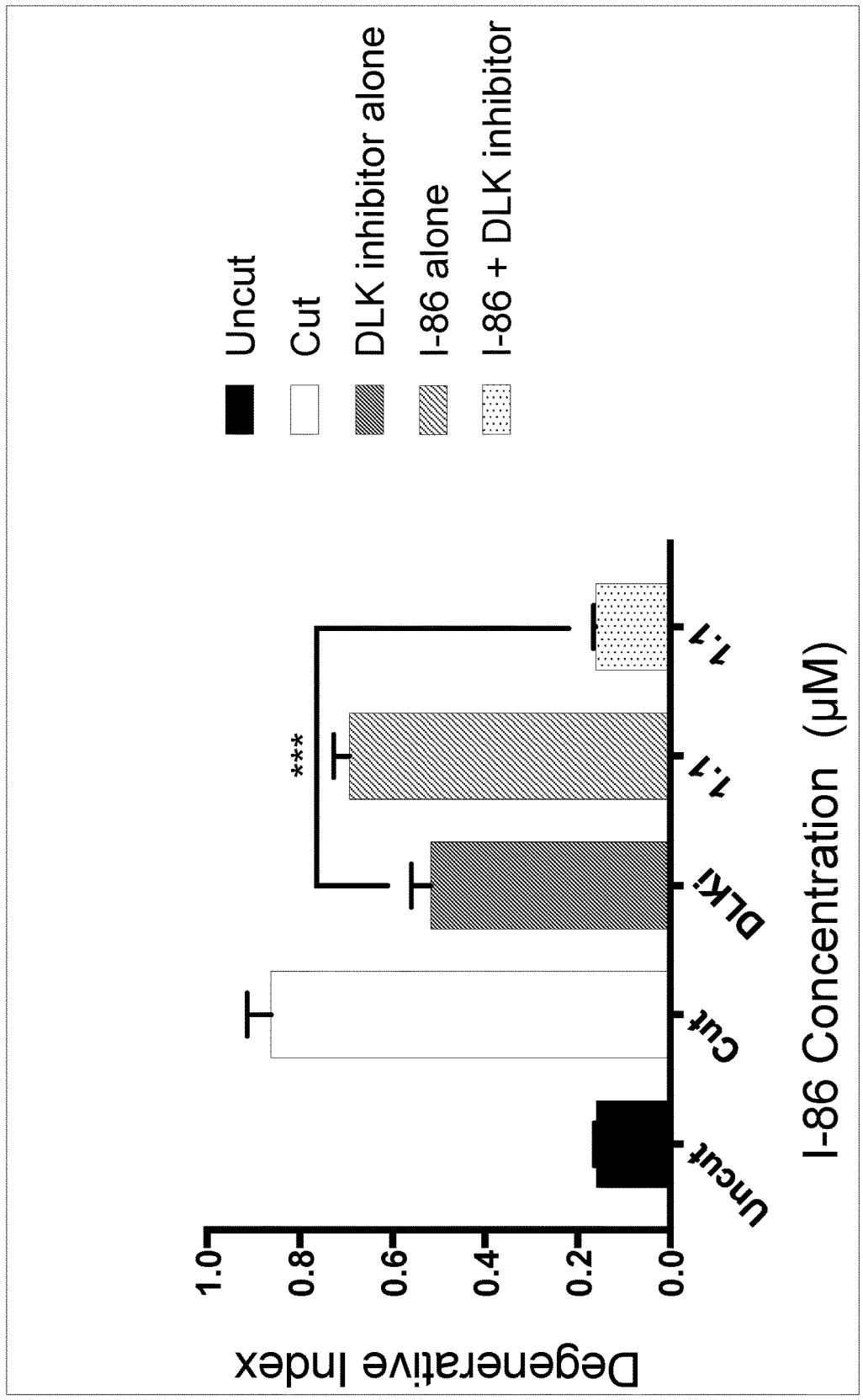

A potent SARM1 inhibitor, I-86, was used to further assess the axonal protection conferred when applied in combination with DLK inhibitor GNE-3511, on the axon degeneration assay described herein. In FIG. 2A, 100 nM DLK inhibitor provided no axonal protection, whereas at 1.1 compound I-86 demonstrated a small, but statistically significant amount of axonal protection. Surprisingly, the combination of 1.1 µM compound I-86+100 nM DLK inhibitor provided robust and statistically significant axonal protection that was greater than the sum of the individual effects of either agent alone. In FIG. 2B, 300 nM DLK inhibitor alone or 1.1 µM of compound I-86 alone provided a modest level of protection. Surprisingly, the combination of 1.1 µM compound I-86+300 nM DLK inhibitor provided robust and statistically significant protection. Furthermore, the magnitude of the combined effect of 1.1 µM compound I-86 and 300 nM DLK inhibitor is greater than the sum of the individual effects of either agent alone, indicating that the effect of combining these agents is not simply additive but in fact synergistic and could not have been predicted from the individual effect of each agent in isolation.

Figure 3A:
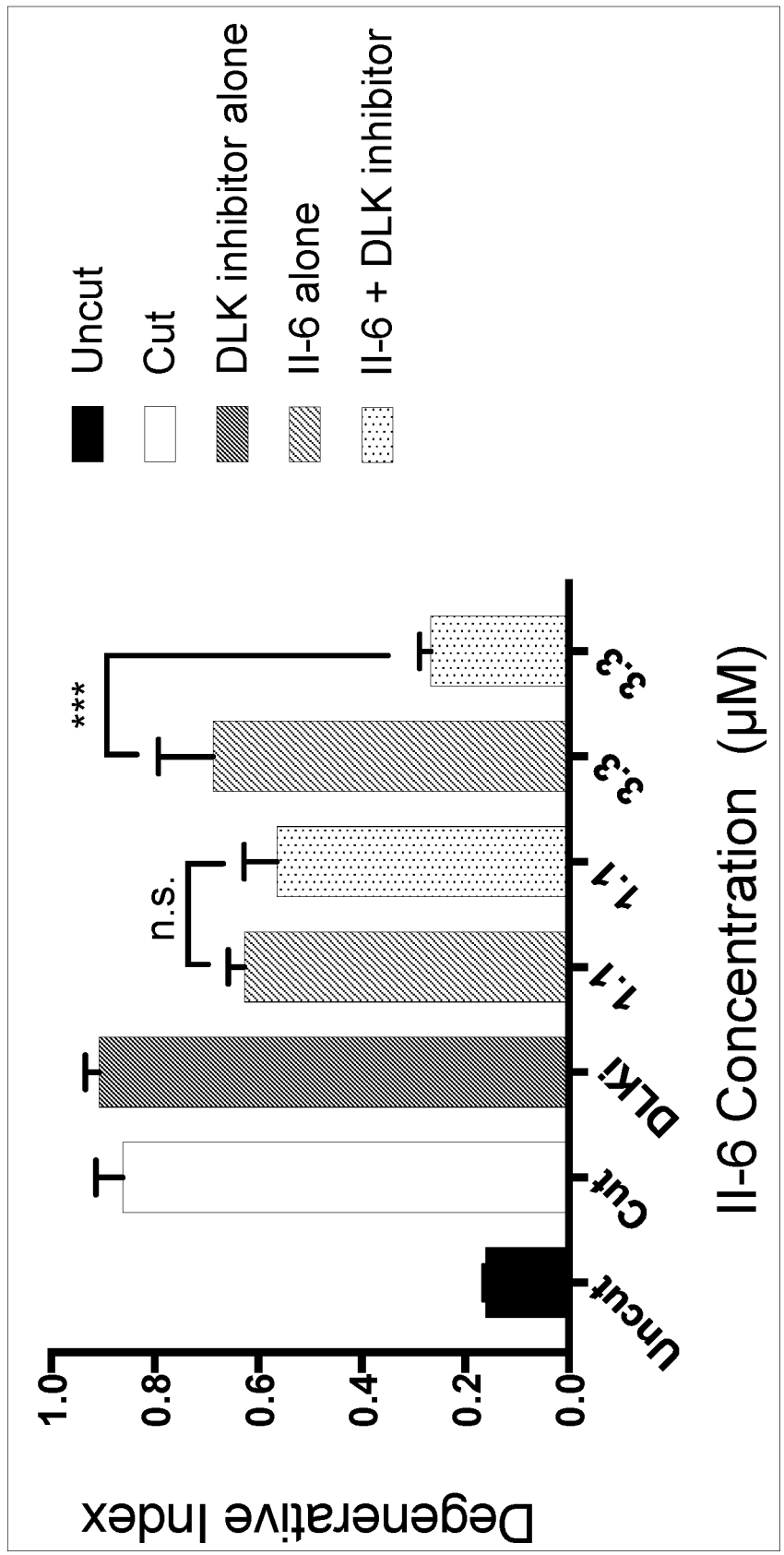
FIG. 3A and FIG. 3B illustrate that the combination of compound II-6, a SARM1 inhibitor, with DLK inhibitor (GNE-3511) increases neuroprotection post-axotomy as compared to single agent therapy. For each concentration of compound II-6 tested, the extent of axonal protection of a combination of compound II-6+DLK inhibitor was compared to the amount of protection produced by the agent in that combination that, individually, had the greater protective effect.
Figure 3B:
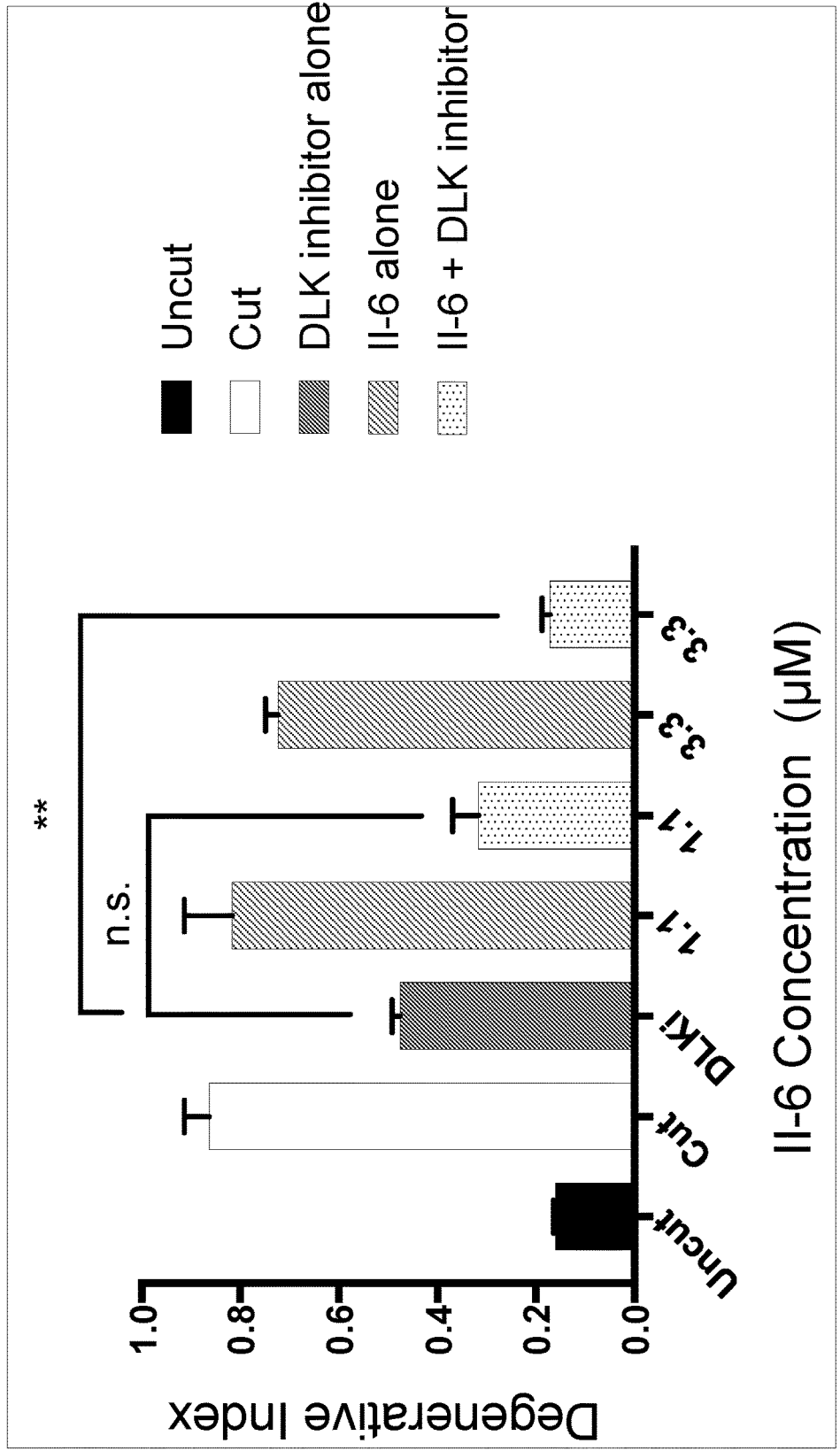

The efficacy SARM1 inhibitors when applied in combination with a DLK inhibitor on the axon degeneration assay described herein was also tested with two isothiazole compounds. The SARM1 inhibitor II-6 was tested on the axon degeneration assay in combination with DLK inhibitor GNE-3511. FIGS. 3A and 3B show the degeneration index of DRG axons 16 hours post-axotomy. In FIG. 3A, 100 nM DLK inhibitor provided no axonal protection, whereas 1.1 or 3.3 µM compound II-6 demonstrated modest, but statistically significant axonal protection. Surprisingly, the combination of 3.3 µM compound II-6+100 nM DLK inhibitor provided robust and statistically significant protection. Furthermore, the magnitude of the combined effect of 3.3 µM compound II-6 and 100 nM DLK inhibitor is greater than the sum of the individual effects of either agent alone, and shows almost complete protection from injury, indicating that the effect of combining these agents is not simply additive but in fact synergistic and could not have been predicted from the individual effect of each agent in isolation. In FIG. 3B, 300 nM DLK inhibitor alone or 3.3 µM of compound II-6 alone provided a modest level of protection. The combination of 3.3 µM of compound II-6+300 nM DLK inhibitor provided robust and statistically significant protection as compared to 300 nM DLK inhibitor alone. Furthermore, the magnitude of the combined effect of 3.3 µM compound II-6 and 300 nM DLK inhibitor is greater than the sum of the individual effects of either agent alone, and shows complete protection from injury, indicating that the effect of combining these agents is not simply additive but in fact synergistic and could not have been predicted from the individual effect of each agent in isolation.

Figure 4A:
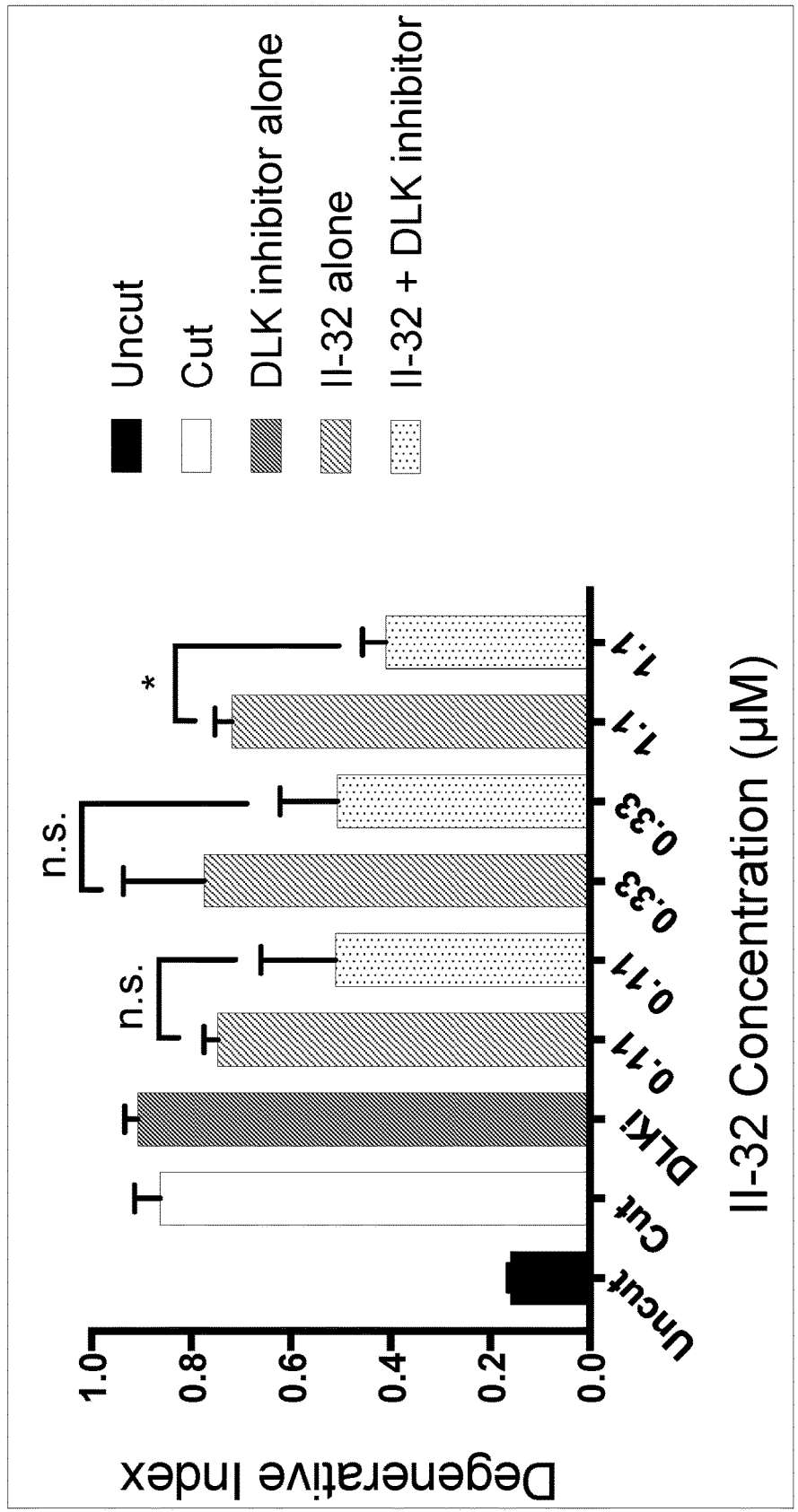
FIG. 4A and FIG. 4B illustrate that the combination of compound II-32, a SARM1 inhibitor, with DLK inhibitor (GNE-3511) extends neuroprotection post-axotomy as compared to single agent therapy. For each concentration of compound II-32 tested, the extent of axonal protection of a combination of compound II-32+DLK inhibitor was compared to the amount of protection produced by the agent in that combination that, individually, had the greater protective effect.
Figure 4B:
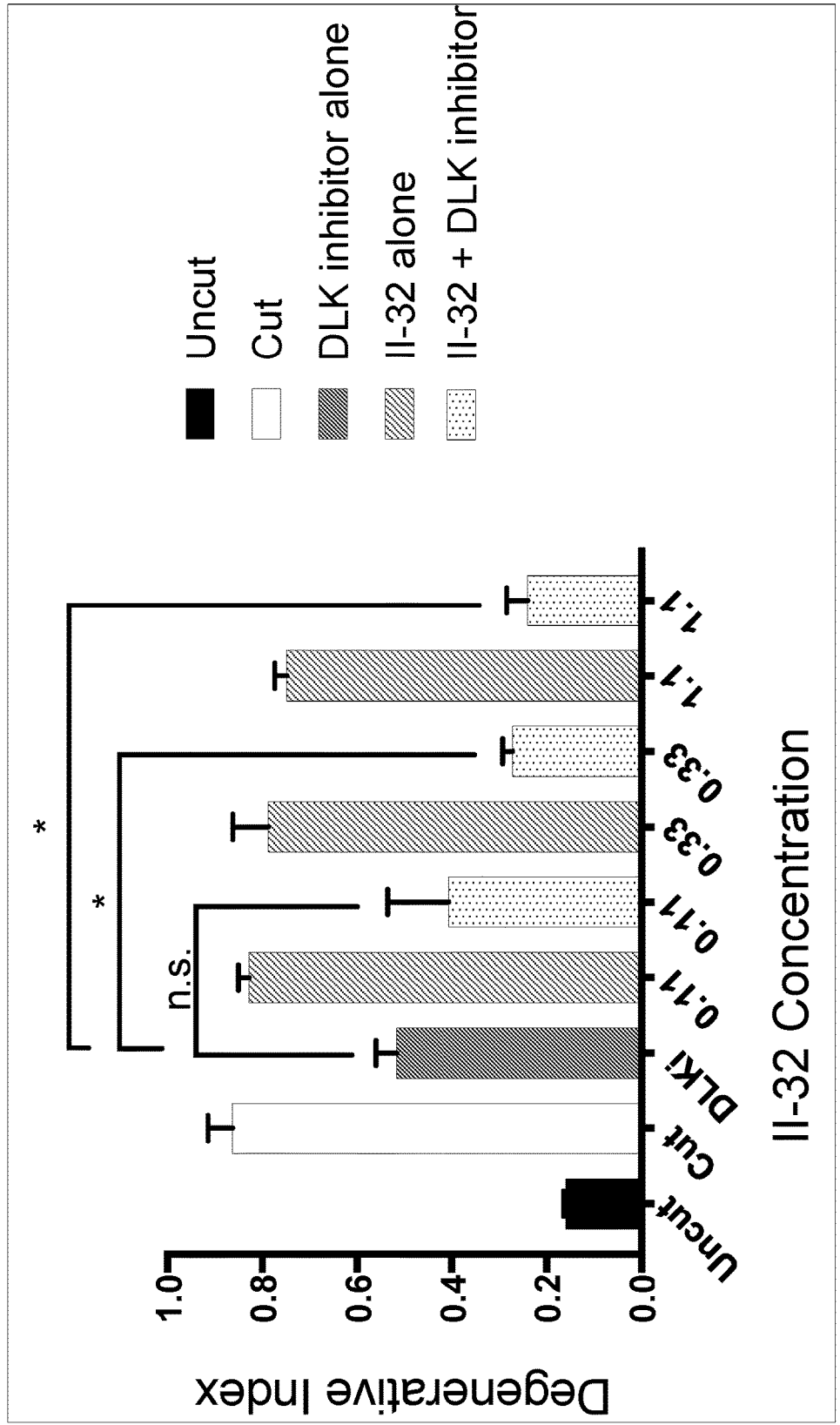

The effect of combining a SARM1 inhibitor with a DLK inhibitor was further tested with the SARM1 inhibitor II-32 in combination with DLK inhibitor GNE-3511 on the axon degeneration assay described herein. The combination of compound II-32+DLK inhibitor increases neuroprotection post-axotomy as compared to single agent therapy. FIGS. 4A and 4B show the degeneration index of DRG axons 16 hours post-axotomy. In FIG. 4A, 100 nM DLK inhibitor provided no axonal protection, whereas 0.11, 0.33 or 1.1 µM compound II-32 demonstrated a modest but not statistically significant axonal protection at these concentrations. The combination of 0.11, 0.33 or 1.1 µM compound II-32+100 nM DLK inhibitor provided greater protection than either agent alone, reaching statistical significance at 1.1 µM of compound II-32. Furthermore, the magnitude of the combined effect of 1.1 µM compound II-32 and 100 nM DLK inhibitor is greater than the sum of the individual effects of either agent alone, indicating that the effect of combining these agents is not simply additive but in fact synergistic and could not have been predicted from the individual effect of each agent in isolation. In FIG. 4B, 300 nM DLK inhibitor alone provided a modest but statistically significant level of axonal protection, whereas 0.11, 0.33 or 1.1 µM compound II-32 alone provided only slight and not statistically significant protection at these concentrations. However, the combination of 0.33 or 1.1 µM compound II-32+300 nM DLK inhibitor provided robust and statistically significant protection as compared to 300 nM DLK inhibitor alone. Furthermore, the magnitude of the combined effect of 0.33 or 1.1 µM compound II-32 and 300 nM DLK inhibitor is greater than the sum of the individual effects of either agent alone, indicating that the effect of combining these agents is not simply additive but in fact synergistic and could not have been predicted from the individual effect of each agent in isolation.

Taken together, these results demonstrate the neuroprotective efficacy of SARM1 inhibitors when provided in combination with a DLK inhibitor on the axon degeneration assay described herein.

Example 2

In this example, as described herein, the ability of SARM1 inhibitors in combination with NAMPT inhibitors to prevent axonal degeneration is demonstrated with the axonal degeneration assay.
Mouse DRG Drop Culture Primary embryonic dorsal root ganglia (DRG) cells are isolated from embryonic day (E) 12.5 CD1 mouse embryos. DRG cells are isolated from wild-type embryos at 12.5. Mouse (DRG) are dissected out (50 ganglia per embryo) and incubated with 0.5% Trypsin solution containing 0.02% EDTA (Gibco) at 37° C. for 15 minutes. The cells are then triturated by gentle pipetting and washed 3 times with DRG growth medium (Neurobasal medium (Gibco) containing 2% B27 (Invitrogen), 100 ng/ml 2.5S NGF (Harland Bioproducts), 1 mM 5-fluoro-2'deoxyuridine (Sigma), penicillin, and streptomycin). Cells are suspended in the DRG growth medium. DRG drop cultures are created by spotting 5000 cells/well into the center of each well of a 96-well tissue culture plate coated with poly-D-Lysine (0.1 mg/ml; Sigma) and laminin (3 mg/ml; Invitrogen). Cells are allowed to adhere to the plates in a humidified tissue culture incubator (5% $CO_2$) for 15 minutes and then DRG growth medium is gently added (100 ml well). DRG neurons are maintained in neurobasal medium supplemented with L-glutamine (Invitrogen), 2% (vol/vol) B27 (Invitrogen), 50 ng/mL NGF (Harlan Laboratories), and 1 µM 5-fluoro-2'deoxyuridine plus 1 µM uridine (Sigma) to induce death of mitotic cells. DRG neurons are seeded on plates pre-coated with poly-D-lysine and laminin.
Axon Degeneration Assay The axonal protective the effect of combining a NAMPT inhibitor with a SARM1 inhibitor are demonstrated with an axonal degeneration assay. 6 day-old mouse DRG drop cultures are preincubated with a NAMPT inhibitor 24 hours prior to axotomy. Then, 2 hours prior to axotomy, DRG cultures are treated with SARM1 inhibitors, in the continued presence of the NAMPT inhibitors. Isoquinoline SARM1 inhibitors include I-26 and I-86, while isothiazole SARM1 inhibitors tested include II-6 and II-32. The SARM1 inhibitors are tested using concentrations ranging from 0.1 to 33 µM. NAMPT inhibitors are selected from the list of NAMPT inhibitors contained herein, including FK866.

A manual axotomy is performed at time 0 by transecting the axons of the DRG neurons with a blade. After the axotomy is performed, DRG cultures remain exposed to the SARM1 inhibitor alone, NAMPT inhibitor alone, or the combination of SARM1 inhibitor and NAMPT inhibitor. At either 16 or 24 hours, DRG cultures are fixed in a buffered solution containing 1% PFA and sucrose and stored at 4° C. prior to imaging. Bright-field images of DRG axons and cell bodies are collected using the 20× water immersion lens of a Phenix automated confocal microscope (PerkinElmer) and quantitation of axonal damage is performed using in-house developed scripts (Acapella, PerkinElmer). The effects of combining the NAMPT inhibitors with varying concentrations of a SARM1 inhibitor are compared to the individual protective effects of NAMPT inhibitors alone or an equivalent concentration of a SARM1 inhibitor alone.
Results The neuroprotection conferred by the combination of SARM1 inhibitors with NAMPT inhibitors is tested on the acute axotomy assay.

Isoquinoline SARM1 inhibitors I-26 and I-86 are tested on the axon degeneration assay alone or in combination with NAMPT inhibitor FK866. When I-26 is tested on the acute axotomy assay in combination with FK866, neuroprotection and axonal protection is increased over the protection achieved by either agent alone at their corresponding single-agent concentrations. Similarly, when I-86 is tested on the acute axotomy assay in combination with FK866, the degree of neuroprotection and axonal protection is increased over the protection achieved by either agent alone at their corresponding single-agent concentrations.

Isothiazole SARM1 inhibitors II-6 and II-32 are tested on the axon degeneration assay alone or in combination with NAMPT inhibitor When II-6 is tested on the acute axotomy assay in combination with FK866, neuroprotection and axonal protection is increased over the protection achieved by either agent alone at their corresponding single-agent concentrations. Similarly, when II-32 is tested on the acute axotomy assay in combination with FK866, the degree of neuroprotection and axonal protection is increased over the protection achieved by either agent alone at their corresponding single-agent concentrations.

Taken together, these results demonstrate the neuroprotective efficacy of SARM1 inhibitors provided in combination with the NAMPT inhibitor FK866 on the axon degeneration assay described herein. Both SARM1 inhibitors and NAMPT inhibitors provided neuroprotection following acute axotomy. The combination of SARM1 inhibitors with NAMPT inhibitors provided neuroprotection greater than either compound alone.

OTHER EMBODIMENTS

The recitation of a listing of elements in any definition of a variable herein includes definitions of that variable as any single element or combinations (or subcombinations) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A combination therapy comprising a SARM1 inhibitor selected from the group consisting of:

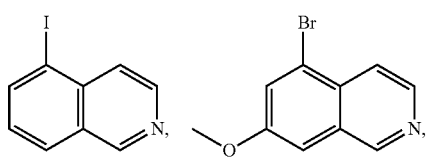

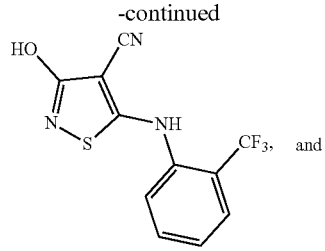

and

-continued

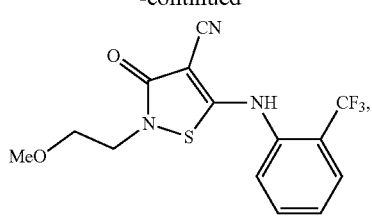

or a pharmaceutically acceptable salt thereof,
and a DLK inhibitor of the structure

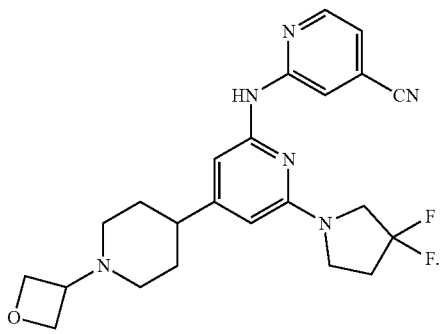 [SMILES: N#Cc1ccnc(Nc2cc(C3CCN(C4COC4)CC3)cc(N3CCC(F)(F)C3)n2)c1]

3. A method comprising administering to a patient at risk for developing a neurodegenerative disease or disorder a SARM1 inhibitor selected from the group consisting of:

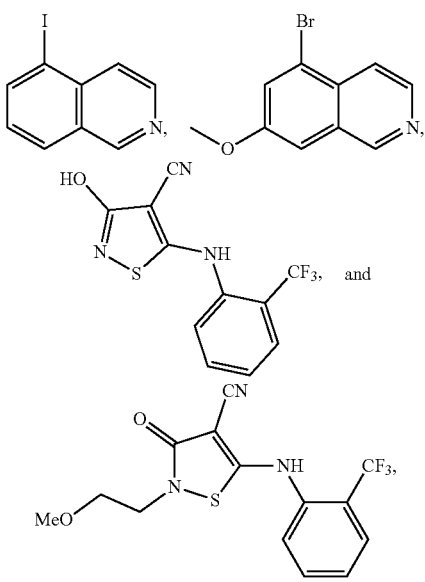

2. A method for treating and/or preventing axonal degeneration comprising administering to a patient in need thereof a SARM1 inhibitor selected from the group consisting of:

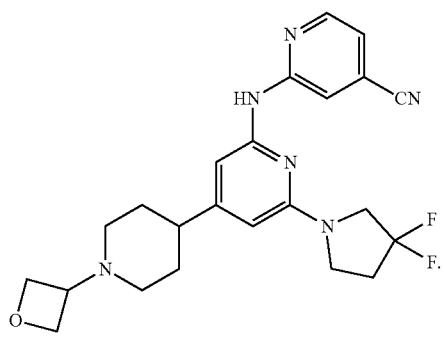 [SMILES: N#Cc1ccnc(Nc2cc(C3CCN(C4COC4)CC3)cc(N3CCC(F)(F)C3)n2)c1]

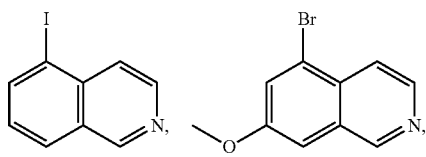

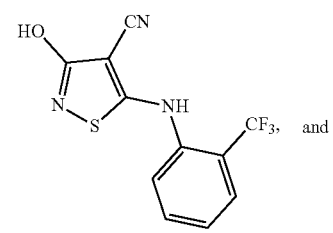

or a pharmaceutically acceptable salt thereof, in combination with a DLK inhibitor of the structure

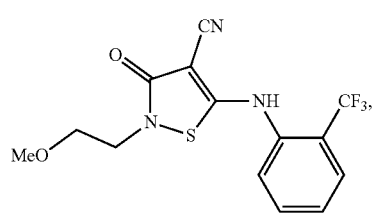

or a pharmaceutically acceptable salt thereof, in combination with a DLK inhibitor of the structure

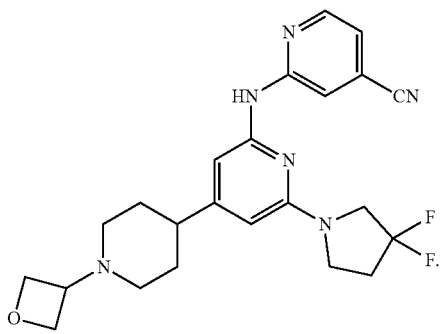 [SMILES: N#Cc1ccnc(Nc2cc(C3CCN(C4COC4)CC3)cc(N3CCC(F)(F)C3)n2)c1]

4. The method according to claim 2, wherein the axonal degeneration causes a neurodegenerative disease or disorder selected from an acute or chronic peripheral nervous system disease or disorder, an acute or chronic central nervous system disease or disorder, or a disease associated with neurodegeneration.

5. The method according to claim 4, wherein the neurodegenerative disease is a chronic disease or disorder of the peripheral nervous system selected from a systemic disorder, a pain disorder, or a metabolic disease or disorder, wherein the systemic disorder is selected from diabetes, uremia, an infectious disease, AIDS, leprosy, nutritional deficiencies, a vascular disorder, a collagen disorder, atherosclerosis, enteric neuropathies and axonopathies, Guillain-Barre syndrome, severe acute motor axonal neuropathy (AMAN), an autoimmune disease, systemic lupus erythematosus, scleroderma, sarcoidosis, rheumatoid arthritis, and polyarteritis nodosa;

wherein the pain disorder is selected from chronic pain, fibromyalgia, spinal pain, carpal tunnel syndrome, pain from cancer, arthritis, sciatica, headaches, pain from surgery, muscle spasms, back pain, visceral pain, pain from injury, dental pain, neuralgia, neurogenic pain, neuropathic pain, nerve inflammation or damage, shingles, herniated disc, torn ligament, and diabetes;

wherein the metabolic disease or disorder is selected from diabetes mellitus, hypoglycemia, uremia, hypothyroidism, hepatic failure, polycythemia, amyloidosis, acromegaly, porphyria, disorders of lipid-/glycolipid-metabolism, nutritional-/vitamin-deficiencies, and mitochondrial disorders.

6. The method according to claim 4, wherein the neurodegenerative disease is an acute disease or disorder of the peripheral nervous system selected from mechanical injuries, thermal injury, and chemical injury or chemotherapy induced neuropathy (CIPN), wherein mechanical injuries are selected from compression or entrapment injuries, carpal tunnel syndrome, direct trauma, penetrating injuries, contusions, fractures or dislocated bones; pressure involving superficial nerves or from a tumor; and a traumatic neuronal injury resulting from increased intraocular pressure;

wherein agents that induce chemical injury or chemotherapy induced neuropathy (CIPN) are selected from cytotoxic anticancer agents, thalidomide, epothilones, ixabepilone, taxanes, paclitaxel, docetaxel, vinca alkaloids, vinblastine, vinorelbine, vincristine, vindesine, proteasome inhibitors, bortezomib, platinum-based drugs, cisplatin, oxaliplatin, carboplatin, auristatins, and conjugated monomethyl auristatin E.

7. The method according to claim 4, wherein the neurodegenerative disease is a central nervous system disease or disorder, an optic nerve disorder, a traumatic brain injury, or metabolic disease or disorder;

wherein a chronic central nervous system disorder is selected from Alzheimer's disease, Parkinson's disease, amyotrophic lateral sclerosis (ALS, Lou Gehrig's disease), multiple sclerosis, Huntington's disease, senile dementia, Pick's disease, Gaucher's disease, Hurler Syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, hereditary ataxias, noise induced hearing loss, Creutzfeldt-Jakob disease, transmissible spongiform encephalopathy, congenital hearing loss, age-related hearing loss, Lewy Body Dementia, frontotemporal dementia, amyloidosis, diabetic neuropathy, globoid cell leukodystrophy (Krabbe's disease), Bassen-Kornzweig syndrome, transverse myelitis, Charcot-Marie-Tooth disease, motor neuron disease, spinocerebellar ataxias, preeclampsia, hereditary spastic paraplegias, spastic paraparesis, familial spastic paraplegia, French settlement disease, Strumpell-Lorrain disease, non-alcoholic steatohepatitis (NASH), hereditary sensory and autonomic neuropathy (HSAN), adrenomyeloneuropathy, progressive supra nuclear palsy (PSP), Friedrich's ataxia, or caused by a somatic mutation or idiopathic condition;

wherein the optic nerve disorder is selected from an acute optic neuropathy (AON), a genetic or idiopathic retinal condition, Leber's congenital amaurosis, Leber's hereditary optic neuropathy, primary open angle glaucoma, acute angle closure glaucoma, autosomal dominant optic atrophy, retinal ganglion degeneration, retinitis pigmentosa and outer retinal neuropathies, optic nerve neuritis and/or degeneration, optic nerve neuritis and/or degeneration associated with multiple sclerosis, Kjer's disease, ischemic optic neuropathies, deficiencies in vitamins B12 or folic acid, isolated vitamin E deficiency syndrome, non-arteritic anterior ischemic optic neuropathy, and exposure to ethambutol or cyanide;

wherein the traumatic brain injury is selected from chronic injury to the central nervous system, spinal cord injury, traumatic axonal injury and chronic traumatic encephalopathy (CTE); and wherein the metabolic disease or disorder is selected from diabetes mellitus, hypoglycemia, Bassen-Kornzweig syndrome, uremia, hypothyroidism, hepatic failure, polycythemia, amyloidosis, acromegaly, porphyria, disorders of lipid-/glycolipid-metabolism, nutritional-/vitamin-deficiencies, and mitochondrial disorders.

8. The method according to claim 4, wherein the neurodegenerative disease is an acute disease or disorder of the central nervous system selected from ischemia or stroke, traumatic brain injury, chemical injury, thermal injury, and viral encephalitides;

wherein ischemia or stroke includes acute ischemia, cerebral ischemia, hypoxic demyelination, ischemic demyelination, ischemic optic neuropathies, non-arteritic anterior ischemic optic neuropathy;

wherein the traumatic brain injuries are selected from injuries to the spinal cord and/or traumatic brain injury, mechanical injuries or traumatic injuries to the head and spine, blunt force trauma, closed-head injury, open head injury, exposure to a concussive and/or explosive force, a penetrating injury in or to the brain cavity or innervated region of the body, a force which causes axons to deform, stretch, crush or sheer, or increased intraocular pressure; and wherein viral encephalitidies include enteroviruses, arboviruses, herpes simplex virus, West Nile virus encephalitis, La Crosse virus encephalitis, Bunyavirus encephalitis, pediatric viral encephalitis, and AIDS dementia complex.

9. The method according to claim 4, wherein the neurodegenerative disease or disorder results from blood clotting, inflammation, flushing, obesity, aging, stress, cancer, diabetes, - or-pair.

* * * * *

UNITED STATES PATENT AND TRADEMARK OFFICE
CERTIFICATE OF CORRECTION

PATENT NO. : 12,083,114 B2  
APPLICATION NO. : 17/413689  
DATED : September 10, 2024  
INVENTOR(S) : Todd Bosanac et al.

Page 1 of 1

It is certified that error appears in the above-identified patent and that said Letters Patent is hereby corrected as shown below:

In the Claims

In Column 99, Line 58, In Claim 7, delete "myelolysis," and insert -- myelinolysis, --.

In Column 100, Line 57, In Claim 8, delete "encephalitidies" and insert -- encephalitides --.

In Column 100, Line 65, In Claim 9, delete "- or-pair." and insert -- -or-pain. --.

Signed and Sealed this  
Seventh Day of January, 2025

Derrick Brent  
*Acting Director of the United States Patent and Trademark Office*

```
                       SEQUENCE LISTING

<160> NUMBER OF SEQ ID NOS: 11

<210> SEQ ID NO 1
<211> LENGTH: 25
<212> TYPE: RNA
<213> ORGANISM: Artificial Sequence
<220> FEATURE:
<223> OTHER INFORMATION: Chemically synthesized nucleotide

<400> SEQUENCE: 1
gcucaggcga gagcaagcuu uagaa                                              25

<210> SEQ ID NO 2
<211> LENGTH: 25
<212> TYPE: RNA
<213> ORGANISM: Artificial Sequence
<220> FEATURE:
<223> OTHER INFORMATION: Chemically synthesized nucleotide

<400> SEQUENCE: 2
uucuaaagcu ugcucucgcc ugagc                                              25

<210> SEQ ID NO 3
<211> LENGTH: 25
<212> TYPE: RNA
<213> ORGANISM: Artificial Sequence
<220> FEATURE:
<223> OTHER INFORMATION: Chemically synthesized nucleotide

<400> SEQUENCE: 3
cccucauguu gcaacuagaa cucaa                                              25

<210> SEQ ID NO 4
<211> LENGTH: 25
<212> TYPE: RNA
<213> ORGANISM: Artificial Sequence
<220> FEATURE:
<223> OTHER INFORMATION: Chemically synthesized nucleotide

<400> SEQUENCE: 4
uugaguucua guugcaacau gaggg                                              25

<210> SEQ ID NO 5
<211> LENGTH: 25
<212> TYPE: RNA
<213> ORGANISM: Artificial Sequence
<220> FEATURE:
<223> OTHER INFORMATION: Chemically synthesized nucleotide

<400> SEQUENCE: 5
ccaauagugu ccugcagcua cauga                                              25

<210> SEQ ID NO 6
<211> LENGTH: 25
<212> TYPE: RNA
<213> ORGANISM: Artificial Sequence
<220> FEATURE:
<223> OTHER INFORMATION: Chemically synthesized nucleotide

<400> SEQUENCE: 6
```

```
ucauguagcu gcaggacacu auugg                                    25

<210> SEQ ID NO 7
<211> LENGTH: 20
<212> TYPE: DNA
<213> ORGANISM: Artificial Sequence
<220> FEATURE:
<223> OTHER INFORMATION: Chemically synthesized nucleotide

<400> SEQUENCE: 7
catcatctgg gtgtgggaag                                          20

<210> SEQ ID NO 8
<211> LENGTH: 29
<212> TYPE: DNA
<213> ORGANISM: Artificial Sequence
<220> FEATURE:
<223> OTHER INFORMATION: Chemically synthesized nucleotide

<400> SEQUENCE: 8
aagttggcag caccaacact gatgagcga                                29

<210> SEQ ID NO 9
<211> LENGTH: 30
<212> TYPE: DNA
<213> ORGANISM: Artificial Sequence
<220> FEATURE:
<223> OTHER INFORMATION: Chemically synthesized nucleotide

<400> SEQUENCE: 9
aaggaggatg tcctggtcta ctgaagtcac                               30

<210> SEQ ID NO 10
<211> LENGTH: 29
<212> TYPE: DNA
<213> ORGANISM: Artificial Sequence
<220> FEATURE:
<223> OTHER INFORMATION: Chemically synthesized nucleotide

<400> SEQUENCE: 10
cctgtctgga caatgattgg caaagccta                                29

<210> SEQ ID NO 11
<211> LENGTH: 29
<212> TYPE: DNA
<213> ORGANISM: Artificial Sequence
<220> FEATURE:
<223> OTHER INFORMATION: Chemically synthesized nucleotide

<400> SEQUENCE: 11
gagtagcctg gatggctcct gaagtgatc                                29
```